(12) United States Patent
Finlay

(10) Patent No.: US 10,975,165 B2
(45) Date of Patent: Apr. 13, 2021

(54) DE-IMMUNISED ANTI-ERBB3 ANTIBODIES

(71) Applicant: ULTRAHUMAN THIRTEEN LIMITED, Sandwich (GB)

(72) Inventor: William James Jonathan Finlay, Sandwich (GB)

(73) Assignee: ULTRAHUMAN THIRTEEN LIMITED, Sandwich (GB)

( * ) Notice: Subject to any disclaimer, the term of this patent is extended or adjusted under 35 U.S.C. 154(b) by 0 days.

(21) Appl. No.: 16/925,570

(22) Filed: Jul. 10, 2020

(65) Prior Publication Data
US 2020/0339702 A1 Oct. 29, 2020

Related U.S. Application Data

(63) Continuation of application No. PCT/EP2019/056506, filed on Mar. 14, 2019.

(30) Foreign Application Priority Data
Mar. 14, 2018 (GB) ...................................... 1804094

(51) Int. Cl.
| C07K 16/32 | (2006.01) |
| C07K 16/28 | (2006.01) |
| C07K 16/30 | (2006.01) |
| A61K 47/68 | (2017.01) |

(52) U.S. Cl.
CPC .......... *C07K 16/32* (2013.01); *A61K 47/6801* (2017.08); *A61K 47/6843* (2017.08); *C07K 2317/24* (2013.01); *C07K 2317/52* (2013.01); *C07K 2317/565* (2013.01)

(58) Field of Classification Search
CPC ................ C07K 16/32; C07K 2317/24; C07K 2317/52; C07K 2317/565; C07K 2317/76; C07K 2317/90; C07K 2317/92; A61K 39/395; A61K 47/6843; A61K 47/6801; A61K 2039/505
See application file for complete search history.

(56) References Cited

U.S. PATENT DOCUMENTS

2017/0073395 A1   3/2017   Finlay et al.

FOREIGN PATENT DOCUMENTS

| WO | WO 2011/136911 A2 | 11/2011 |
| WO | WO 2014/159915 A1 | 10/2014 |

OTHER PUBLICATIONS

International Search Report and Written Opinion dated Jun. 12, 2019 for International Application No. PCT/EP2019/056506, 13 pages.
Griswold, K. E. & Bailey-Kellogg, C., "Design and Engineering of Deimmunized Biotherapeutics," Curr Opin Struct Biol, 39:79-88 (2016); doi:10.1016/j.sbi.2016.06.003.
Townsend, S. et al., "Augmented Binary Substitution: Single-pass CDR germlining and stabilization of therapeutic antibodies," PNAS, 112(50):15354-15359 (2015).

*Primary Examiner* — Hong Sang
(74) *Attorney, Agent, or Firm* — Cooley LLP; Ivor Elrifi

(57) ABSTRACT

Provided herein are antibody molecules that bind specifically to ERBB3 and related nucleic acid molecules, vectors and host cells. Also provided herein are medical uses of such antibody molecules.

19 Claims, 21 Drawing Sheets
Specification includes a Sequence Listing.

DE-IMMUNISED ANTI-ERBB3 ANTIBODIES

CROSS-REFERENCE TO RELATED APPLICATIONS

This application is a continuation of International Patent Application No. PCT/EP2019/056506, filed on Mar. 14, 2019, which claims the benefit of GB Patent Application No. 1804094.9, filed on Mar. 14, 2018, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ULTH_001_01US_SeqList_ST25.txt, date recorded: Jul. 10, 2020, file size ~141,282 bytes).

FIELD OF THE INVENTION

The invention relates to antibody molecules binding specifically to ERBB3 (also known as ErbB-3, HER3, LCCS2, MDA-BF-1, c-erbB-3, c-erbB3, erbB3-S, p180-ErbB3, p45-sErbB3, p85-sErbB3, erb-b2 receptor tyrosine kinase 3) and medical uses thereof.

BACKGROUND OF THE INVENTION

ERBB3 (also known as ErbB-3, HER3, LCCS2, MDA-BF-1, c-erbB-3, c-erbB3, erbB3-S, p180-ErbB3, p45-sErbB3, p85-sErbB3, and erb-b2 receptor tyrosine kinase 3) is a transmembrane receptor tyrosine kinase (RTK) protein that belongs to the immunoglobulin superfamily. ERBB3 lacks significant tyrosine kinase activity of its own, and is activated via heterodimerization with other related RTKs such as HER2, EGFR, and MET. This heterodimerization is primarily driven by the predominant ligand for ERBB3, which is Heregulin (HRG), also known as Neuregulin 1 (NRG1). ERBB3-HRG interaction triggers the tyrosine phosphorylation of ERBB3 by heterodimer partners and the activation of diverse intracellular signaling networks. Importantly, ERBB3 is the most potent activator of the PI3K/AKT signaling pathway in the EGFR family.

The ERBB3 receptor is often overexpressed in tumours of the head and neck, lung, breast, ovary, prostate, colon, pancreas, and gastrointestinal tract. The overexpression of ERBB3 is strongly linked with poor prognosis, and ERBB3 is believed to be influential in resistance mechanisms to radiotherapy and various chemotherapeutic and biotherapeutic drugs. As the preferred dimerization partner of HER2, amplified ERBB3 signaling in HER2+ breast tumours is believed to be partly responsible for resistance to trastuzumab therapy. Therapeutic antibodies that antagonise ERBB3 signalling by blocking its ability to dimerise with other key receptors have the potential to mediate anti-tumour effects, via two mechanisms: 1. Potent inhibition of the ERBB3 signalling pathway by locking the receptors into a monomeric form. 2. Antibody effector-function mediated engagement of immune cells.

The majority of currently approved antibody therapeutics are derived from immunized rodents. Many of those antibodies have undergone a process known as "humanization", via the "grafting" of murine Complementarity-Determining Regions (CDRs) into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. Antibodies such as anti-ERBB3, which potentially engage immune effector functions as part of their mechanism of action, are at particularly high risk of immunogenicity as they can encourage phagocytosis of ERBB3+ target cells, leading to antigen processing of the antibody along with the target cell. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized antagonistic anti-ERBB3 antibody would therefore have as many residues as possible in the v-domains that are identical to those found in both the frameworks and CDRs of well-characterized human germline sequences. This high level of identity to high-stability germlines that are highly expressed in the maximum number of potential patients minimises the risk of a therapeutic antibody having unwanted immunogenicity in the clinic, or unusually high 'cost of goods' in manufacturing.

Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, in the absence of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently inefficient, requiring an extra stage of modification of the starting antibody sequence. In addition, it cannot currently be accurately predicted what modifications in distal positions of the protein sequence of an individual v-domain, or even on the partner v-domain, might facilitate the removal of risk motifs while maintaining antigen binding affinity and specificity.

CDR germ-lining and development quality optimisation is thus a complex, multifactorial problem, as multiple functional properties of the molecule should preferably be maintained, including in this instance: target binding specificity, affinity to ERBB3 from both human and animal test species (e.g. rhesus monkey, also known as the rhesus macaque, i.e. *Macaca mulatta*), v-domain biophysical stability and/or IgG yield from protein expression platforms used in research, clinical and commercial supply. Antibody engineering studies have shown that mutation of even single residue positions in key CDRs can have dramatic effects on all of these desired molecular properties.

WO2011136911A2 describes an antagonistic murine anti-ERBB3 IgG molecule termed "24C05", and also the preparation of humanized forms (h24C05). Those humanized forms of 24C05 were produced using classical humanization techniques, i.e. by grafting of Kabat-defined murine CDRs into human heavy and light chain framework sequences, with some of the human framework residues being potentially back-mutated to the correspondingly positioned 24C05 murine residues. For reasons noted above, such humanized forms of 24C05 described in WO2011136911A2 are not ideal.

SUMMARY OF THE INVENTION

The present invention provides a number of anti-ERBB3 antibodies and medical uses thereof.

According to one aspect of the invention, there is provided an antibody molecule which specifically binds to human ERBB3, and optionally also to rhesus monkey ERBB3, or an antigen-binding portion thereof, wherein the antibody molecule or antigen-binding portion comprises a heavy chain variable region with:
  an HCDR1 having amino acids in sequence in the following order: G-F-T-F-S-D-Y-G or any amino acid (such as S)-M-S (SEQ ID NO:1);
  an HCDR2 having amino acids in sequence in the following order: V-S-T-I-S-D-G or any amino acid (such as S, D)-G-T or a conservative substitution of T (such as S)-Y or any amino acid (such as T)-T or any amino acid (such as I)-Y-Y-P or any amino acid (such as A)-D-N or a conservative substitution of N (such as S)-V-K-G (SEQ ID NO:2); and an HCDR3 having amino acids in sequence in the following order: E or any amino acid (such as M)-W or any amino acid (such as F, L, M, Q or Y)-G-D-Y or any amino acid (such as A, D, E, H, L, M, N, Q, S, T or W)-D-G-F or any amino acid (such as I, L, W, Y)-D-Y or any amino acid (such as A, D, E, F, H, I, K, L, M, N, Q, R, S, V, W) (SEQ ID NO:3).

In aspects of the invention, the HCDR1 of the antibody molecule or antigen-binding portion may exclude the sequence GFTFSDYAMS (SEQ ID NO:4; 24C05 murine/humanized antibody HCDR1 disclosed in WO2011136911A2; US20110256154A1), the HCDR2 of the antibody molecule or antigen-binding portion may exclude the sequence VSTISDGGTYTYYPDNVKG (SEQ ID NO:5; 24C05 murine/humanized antibody HCDR2 disclosed in WO2011136911A2; US20110256154A1), and/or the HCDR3 of the antibody molecule or antigen-binding portion may exclude the sequence EWGDYDGFDY (SEQ ID NO:6; 24C05 murine/humanized antibody HCDR3 disclosed in WO2011136911A2; US20110256154A1).

The antibody molecule or antigen-binding portion may further comprise a light chain variable region with:
  an LCDR1 having amino acids in sequence in the following order: R-A-S-Q-E or any amino acid (such as S, I, N)-I-S-G or a conservative substitution of G (such as S, T)-Y-L-S or a conservative substitution of S (such as N) (SEQ ID NO:7);
  an LCDR2 having amino acids in sequence in the following order: A or any amino acid (such as E)-A-S-T or a conservative substitution of T (such as S, N)-L-D or any amino acid (such as H, K, Q)-S or T (SEQ ID NO:8); and
  an LCDR3 having amino acids in sequence in the following order: L or any amino acid (such as Q)-Q-Y or any amino acid (such as S)-D or any amino acid (such as Y)-S-Y or any amino acid (such as T, S)-P or any amino acid (such as H)-Y or any amino acid (such as L)-T (SEQ ID NO:9).

In aspects of the invention, the LCDR1 of the antibody molecule or antigen-binding portion may exclude the sequence RASQEISGYLS (SEQ ID NO:10; 24C05 murine/humanized antibody LCDR1 disclosed in WO2011136911A2; US20110256154A1), and/or the LCDR2 of the antibody molecule or antigen-binding portion may exclude the sequence AASTLDS (SEQ ID NO:11; 24C05 murine/humanized antibody LCDR2 disclosed in WO2011136911A2; US20110256154A1), and/or the LCDR3 of the antibody molecule or antigen-binding portion may exclude the sequence LQYDSYPYT (SEQ ID NO:12; 24C05 murine/humanized antibody LCDR3 disclosed in WO2011136911A2; US20110256154A1).

In some aspects, disclosed herein is an anti-ERBB3 antibody or an antigen-binding portion thereof, wherein the antibody comprises a heavy chain variable (VH) region and a light chain variable (VL) region, wherein
  (a) the HCDR1 comprises the amino acid sequence G-F-T-F-S-D-Y-$X_1$-M-S, wherein $X_1$ is G or any other amino acid (SEQ ID NO:1);
  (b) the HCDR2 comprises V-S-T-I-S-D-$X_1$-G-$X_2$-$X_3$-$X_4$-Y-Y-$X_5$-D-$X_6$-V-K-G, wherein $X_1$ is G or any other amino acid, $X_2$ is T or a conservative substitution of T, $X_3$ is Y or any other amino acid, $X_4$ is T or any other amino acid, $X_5$ is P or any other amino acid, and $X_6$ is N or a conservative substitution of N (SEQ ID NO:2);
  (c) the HCDR3 comprises $X_1$-$X_2$-G-D-$X_3$-D-G-$X_4$-D-$X_5$, wherein $X_1$ is E or any other amino acid, $X_2$ is W or any other amino acid, $X_3$ is Y or any other amino acid, $X_4$ is F or any other amino acid, and $X_5$ is Y or any other amino acid (SEQ ID NO:3);
  (d) the LCDR1 comprises R-A-S-Q-$X_1$-I-S-$X_2$-Y-L-$X_3$, wherein $X_1$ is E or any other amino acid, $X_2$ is G or a conservative substitution of G, and $X_3$ is S or a conservative substitution of S (SEQ ID NO:7);
  (e) the LCDR2 comprises $X_1$-A-S-$X_2$-L-$X_3$-S, wherein $X_1$ is A or any other amino acid, $X_2$ is T or a conservative substitution of T, and $X_3$ is or D any other amino acid (SEQ ID NO:8); and
  (f) the LCDR3 comprises $X_1$-Q-$X_2$-$X_3$-S-$X_4$-$X_5$-$X_6$-T, wherein $X_1$ is L or any other amino acid, $X_2$ is Y or any other amino acid, $X_3$ is D or any other amino acid, $X_4$ is Y or any other amino acid, $X_5$ is P or any other amino acid, and $X_6$ is Y or any other amino acid (SEQ ID NO:9). In some aspects, the LCDR2 comprises $X_1$-A-S-$X_2$-L-$X_3$-S (SEQ ID NO:8), wherein the seventh residue in the sequence is a conservative substitution of S (for example, T).

In some aspects, the invention provides an anti-ERBB3 antibody or an antigen-binding portion thereof, wherein the antibody comprises a heavy chain variable (VH) region and a light chain variable (VL) region, wherein
  (a) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); and the VL region amino acid sequence comprises LCDR1 of RASQEISTYLS (SEQ ID NO: 261), LCDR2 of AASTLQS (SEQ ID NO:26) and LCDR3 of LQYDSSPLT (SEQ ID NO: 262);
  (b) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); and the VL region amino acid sequence comprises LCDR1 of RASQEISSYLS (SEQ ID NO: 21), LCDR2 of AASSLDT (SEQ ID NO: 263) and LCDR3 of LQYD-STPYT (SEQ ID NO: 23);

(c) the VH region amino acid sequence comprises HCDR1 of GFTFSDYGMS (SEQ ID NO:13), HCDR2 of VSTISDSGSYTYYPDSVKG (SEQ ID NO:19) and HCDR3 of ELGDYDGFDY (SEQ ID NO:20); and the VL region amino acid sequence comprises LCDR1 of RASQEISSYLS (SEQ ID NO:21), LCDR2 of AASSLDS (SEQ ID NO:22) and LCDR3 of LQYD-STPYT (SEQ ID NO:23);

(d) the VH region amino acid sequence comprises HCDR1 of GFTFSDYSMS (SEQ ID NO:24), HCDR2 of VSTISDSGTYTYYPDSVKG (SEQ ID NO:25) and HCDR3 of EWGDYDGFDF (SEQ ID NO:15); and the VL region amino acid sequence comprises LCDR1 of RASQEISSYLS (SEQ ID NO:21), LCDR2 of AASTLQS (SEQ ID NO:26) and LCDR3 of LQYD-STPLT (SEQ ID NO:18);

(e) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDF (SEQ ID NO:15); and the VL region amino acid sequence comprises LCDR1 of RASQSISSYLS (SEQ ID NO:16), LCDR2 of AASSLQS (SEQ ID NO:17) and LCDR3 of LQYD-STPLT (SEQ ID NO:18);

(f) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDH (SEQ ID NO:27); and the VL region amino acid sequence comprises LCDR1 of RASQEISSYLS (SEQ ID NO:21), LCDR2 of AASSLQS (SEQ ID NO:17) and LCDR3 of LQYD-STPLT (SEQ ID NO:18);

(g) the VH region amino acid sequence comprises HCDR1 of GFTFSDYGMS (SEQ ID NO:13), HCDR2 of VSTISDGGSYTYYADSVKG (SEQ ID NO:28) and HCDR3 of EWGDYDGFDE (SEQ ID NO:29); and the VL region amino acid sequence comprises LCDR1 of RASQSISGYLS (SEQ ID NO:30), LCDR2 of AASTLQS (SEQ ID NO:26) and LCDR3 of LQYD-STPYT (SEQ ID NO:23);

(h) the VH region amino acid sequence comprises HCDR1 of GFTFSDYGMS (SEQ ID NO:13), HCDR2 of VSTISDGGSYTYYADNVKG (SEQ ID NO:31) and HCDR3 of EWGDYDGFDF (SEQ ID NO:15); and the VL region amino acid sequence comprises LCDR1 of RASQSISSYLS (SEQ ID NO:16), LCDR2 of AASTLQS (SEQ ID NO:26) and LCDR3 of LQYD-STPLT (SEQ ID NO:18); or (i) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDE (SEQ ID NO:29); and the VL region amino acid sequence comprises LCDR1 of RASQSISSYLS (SEQ ID NO:16), LCDR2 of AASSLQS (SEQ ID NO:17) and LCDR3 of LQYD-STPLT (SEQ ID NO:18).

In some aspects, disclosed herein is an anti-ERBB3 antibody or an antigen-binding portion thereof, wherein the antibody comprises a heavy chain variable (VH) region and a light chain variable (VL) region, wherein
the VH region amino acid sequence comprises:
(a) HCDR1 of SEQ ID NO: 13 or 24;
(b) HCDR2 of SEQ ID NO: 14, 19, 25, 28 or 31; and
(c) HCDR3 of SEQ ID NO: 15, 20, 27 or 29; and the VL region amino acid sequence comprises:
(a') LCDR1 of SEQ ID NO: 16, 21, 30 or 261;
(b') LCDR2 of SEQ ID NO: 17, 22, 26 or 263; and
(c') LCDR3 of SEQ ID NO: 18, 23 or 262.

In some aspects, disclosed herein is an anti-ERBB3 antibody or an antigen-binding portion thereof, wherein the antibody comprises a heavy chain variable (VH) region and a light chain variable (VL) region, wherein
(a) the VH region amino acid sequence comprises SEQ ID NO:236 and the VL region amino acid sequence comprises SEQ ID NO:225;
(b) the VH region amino acid sequence comprises SEQ ID NO:232 and the VL region amino acid sequence comprises SEQ ID NO:221;
(c) the VH region amino acid sequence comprises SEQ ID NO:253 and the VL region amino acid sequence comprises SEQ ID NO:254; or
(d) the VH region amino acid sequence comprises SEQ ID NO:255 and the VL region amino acid sequence comprises SEQ ID NO:256.

Also provided according to the invention is an immunoconjugate comprising the antibody molecule or antigen-binding portion thereof as defined herein linked, fused or conjugated to a therapeutic agent.

In another aspect the invention provides a nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-ERBB3 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

Further provided herein is an antibody molecule or antigen-binding portion thereof as defined herein, or the immunoconjugate as defined herein, or the nucleic acid molecule as defined herein, or the vector as defined herein, or the pharmaceutical composition as defined herein, for use as a medicament. The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an an autoimmune disease or an inflammatory disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The autoimmune disease or inflammatory disease may be selected in all aspects from the group consisting of: arthritis, asthma, multiple sclerosis, psoriasis, Crohn's disease, inflammatory bowel disease, lupus, Grave's disease and Hashimoto's thyroiditis, and ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease, an inflammatory disease or a fibrotic disease.

The cardiovascular disease in any aspect of the invention may for example be coronary heart disease or atherosclerosis.

The fibrotic disease in any aspect of the invention may be selected from the group consisting of myocardial infarction, angina, osteoarthritis, pulmonary fibrosis, cystic fibrosis, bronchitis and asthma.

The invention also provides a method of producing an antibody molecule which specifically binds to human ERBB3 and optionally also to rhesus monkey ERBB3, or an antigen-binding portion thereof, comprising the steps of:

(1) grafting anti-ERBB3 CDRs from a non-human source into a human v-domain framework to produce a humanized anti-ERBB3 antibody molecule or antigen-binding portion thereof;

(2) generating a phage library of clones of the humanized anti-ERBB3 antibody molecule or antigen-binding portion thereof comprising one or more mutations in the CDRs;

(3) screening the phage library for binding to human ERBB3 and optionally also to rhesus monkey ERBB3;

(4) selecting clones from the screening step (3) having binding specificity to human ERBB3 and optionally also to rhesus monkey ERBB3; and (5) producing an antibody molecule which specifically binds to human ERBB3 and optionally also to rhesus monkey ERBB3, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Figure 1A:
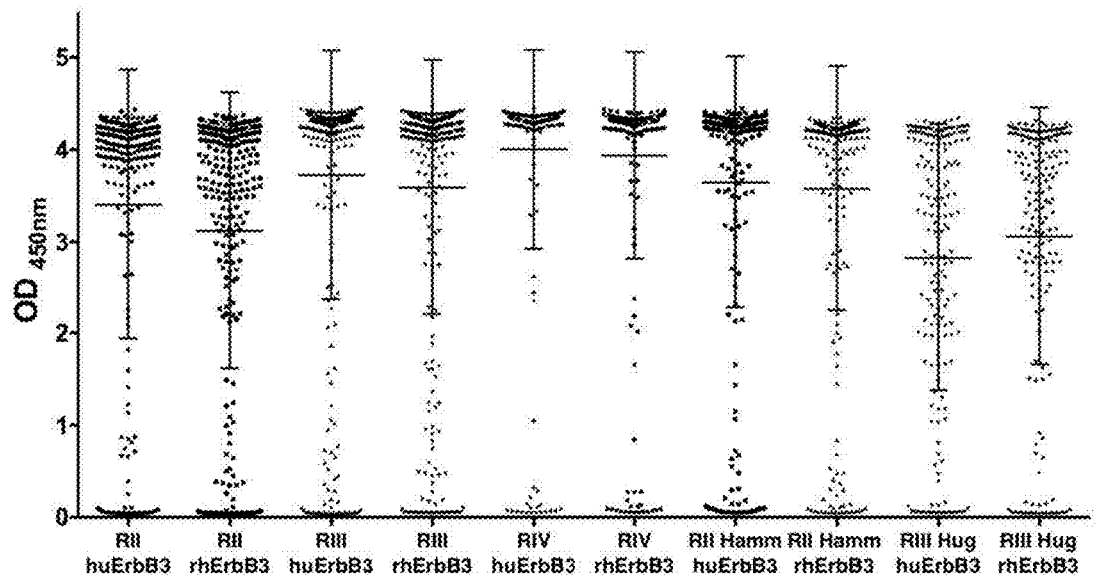
FIG. 1A-FIG. 1B. Direct binding ELISA and Alphascreen competition screening of library-derived anti-ERBB3 Fabs against human and rhesus ERBB3-Fc proteins.
Figure 1B:
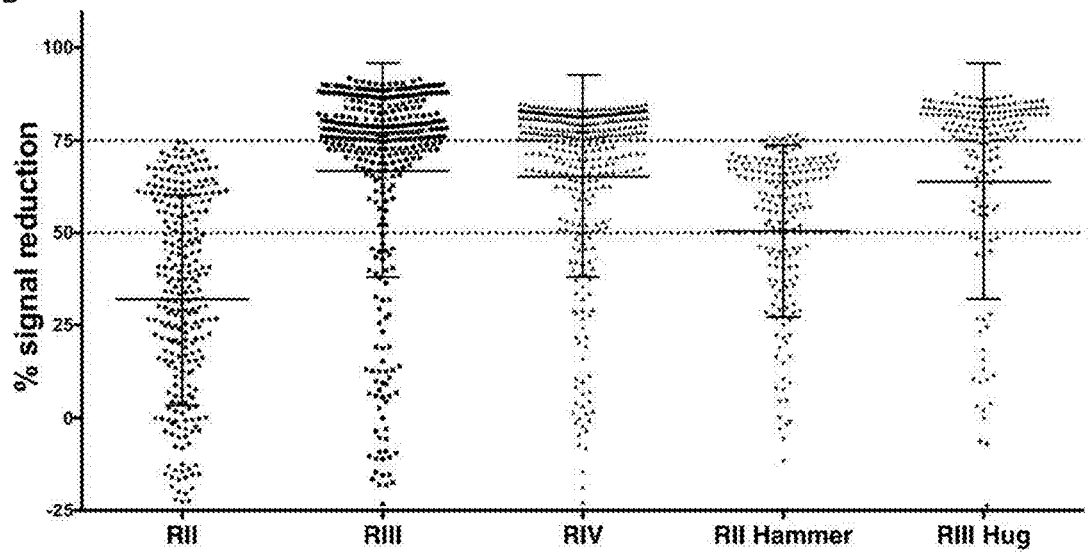

Clones were derived from multiple phage selection branches where phage populations were selected on biotinylated human, or rhesus monkey ERBB3 proteins in each of rounds II-IV. 'Hammer-Hug' rounds were also performed in separate rounds II and III. After each round of selection, library-derived clones were screened as periplasmically-expressed Fab proteins, against both human (huERBB3) and rhesus (rhERBB3) in ELISA (FIG. 1A), and in blocking the binding of 24C05 IgG in binding to huERBB3 by Alphascreen (FIG. 1B). Mean±SD values in each round are represented in grey bars.

Figure 2A:
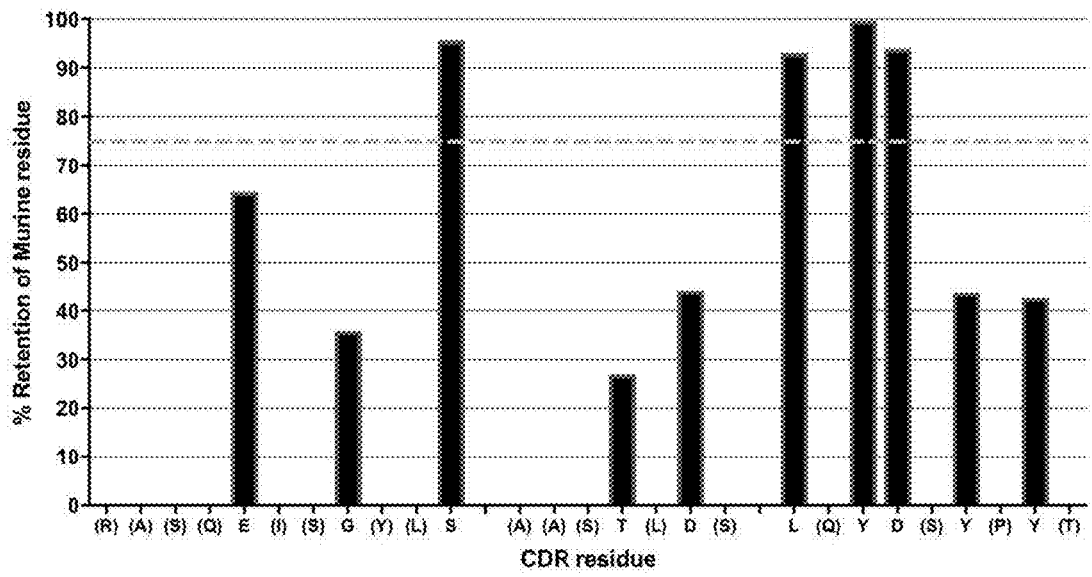
Figure 2B:
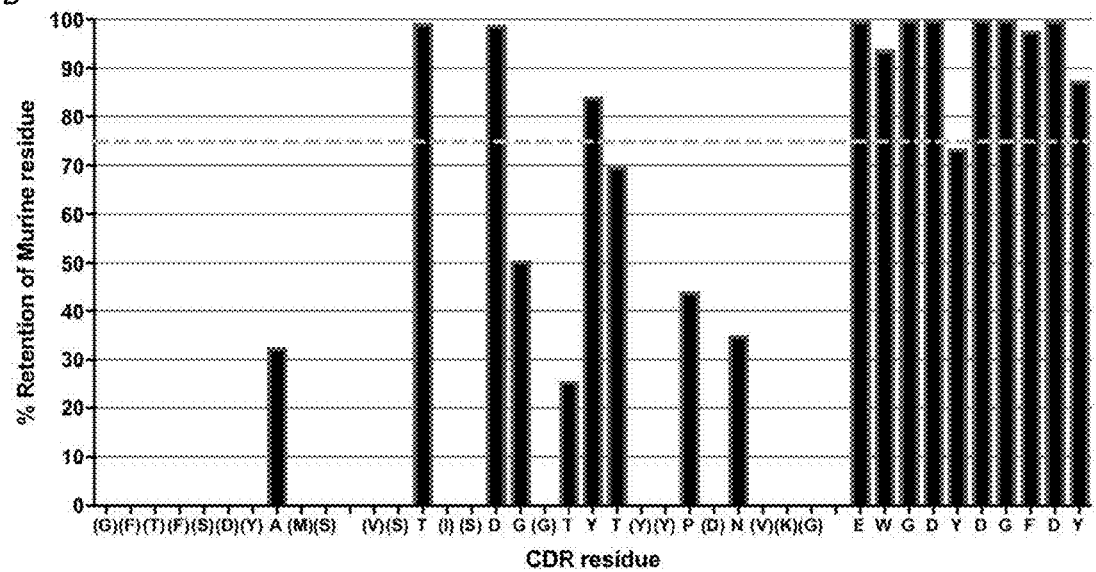

FIG. 2A-FIG. 2B. Analysis of CDR residue tolerance for mutation to germline. A plot of murine amino acid retention frequencies in the CDRs of the ELISA-positive population of 658 unique Fab clones that demonstrated human and rhesus ERBB3 cross-reactivity is shown for $V_L$ (SEQ ID NOs:32-34) (FIG. 2A) and $V_H$ (SEQ ID NOs:35-37) (FIG. 2B) domains, respectively. Only those residues targeted for human/murine residue mutagenesis are plotted, other than in the HCDR3. CDR residues noted in parentheses on the X-axes were identical to those found in the human germlines used for grafting (IGKV1-39 and IGHV3-11). Those residues in the CDRs that are not in parentheses, but whose values are set at 0, were mutated to human germline during the grafting process. In both plots the dashed line in grey at 75% represents the cut off for tolerance of murine residue replacement by human germline.

Figure 3A:
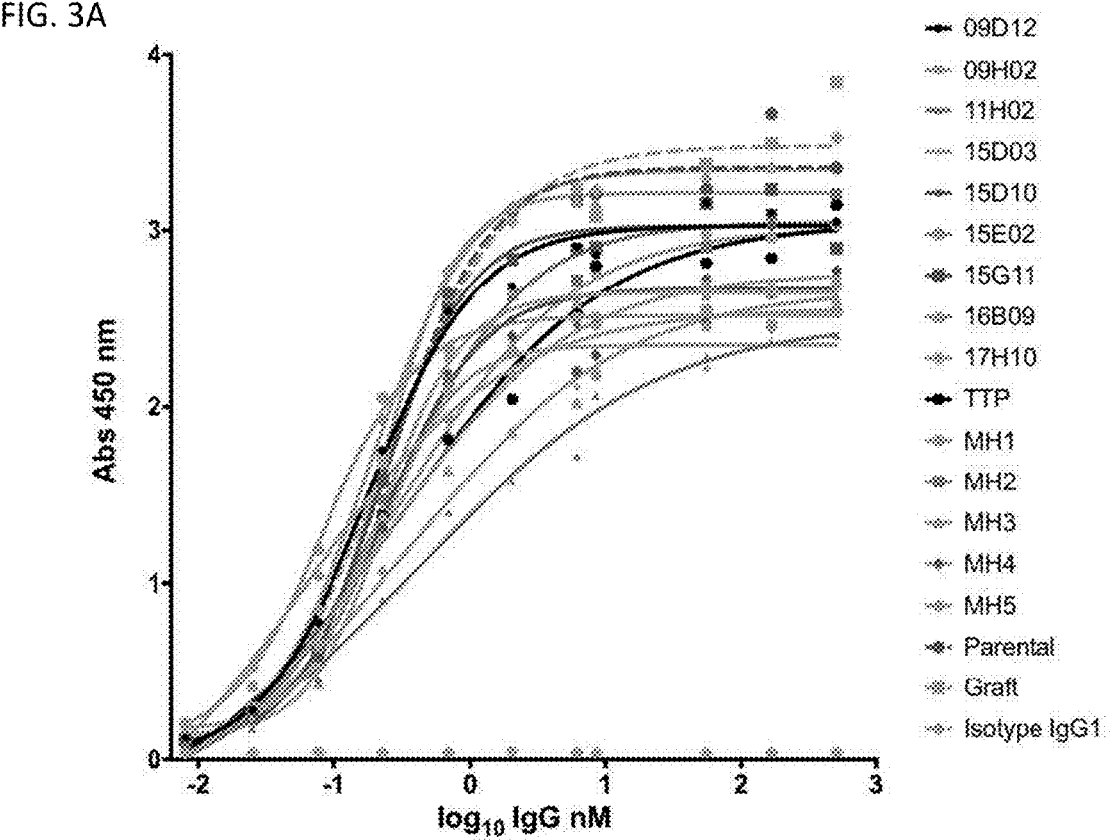
Figure 3B:
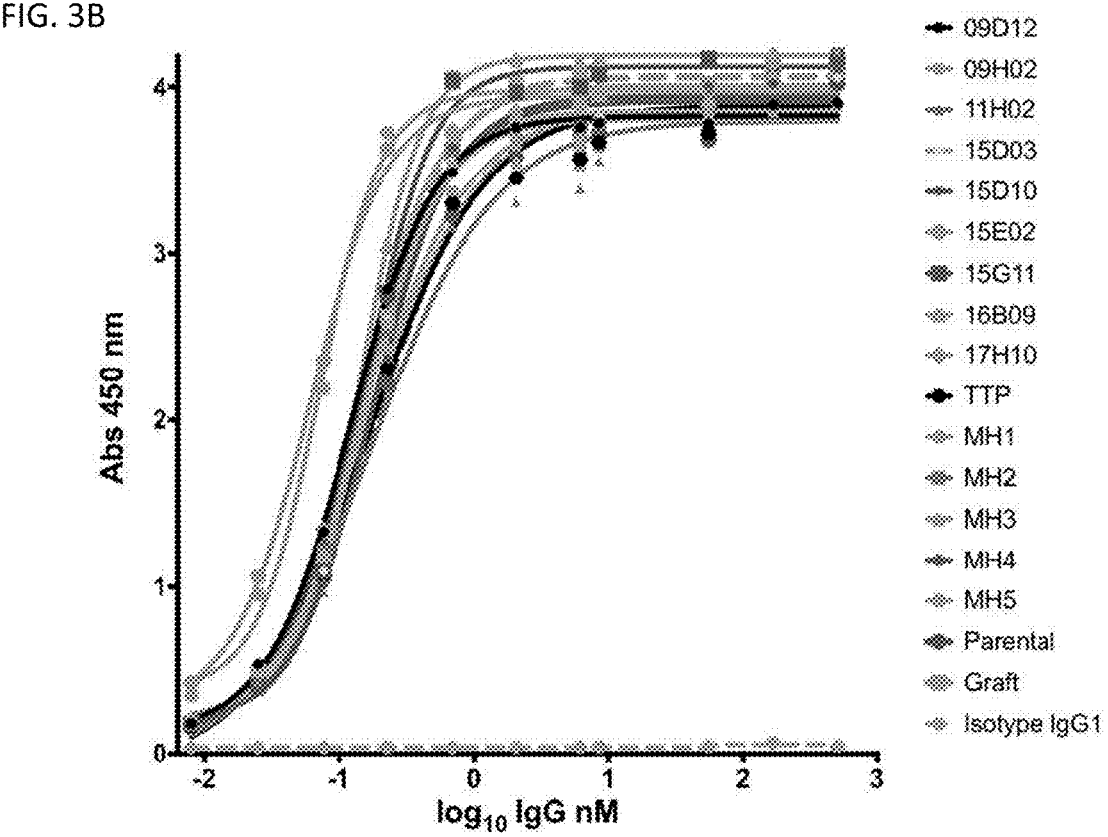

FIG. 3A-FIG. 3B. Direct titration ELISA for IgG binding to human and rhesus ERBB3 proteins. Chimeric and humanized 24C05, library-derived and designer clones in human IgG1null format were titrated (in nM) in a direct binding ELISA against human (FIG. 3A) and rhesus (FIG. 3B) ERBB3-Fc proteins. All clones other than Isotype IgG1null control demonstrated binding activity against both orthologs of ERBB3.

Figure 4:
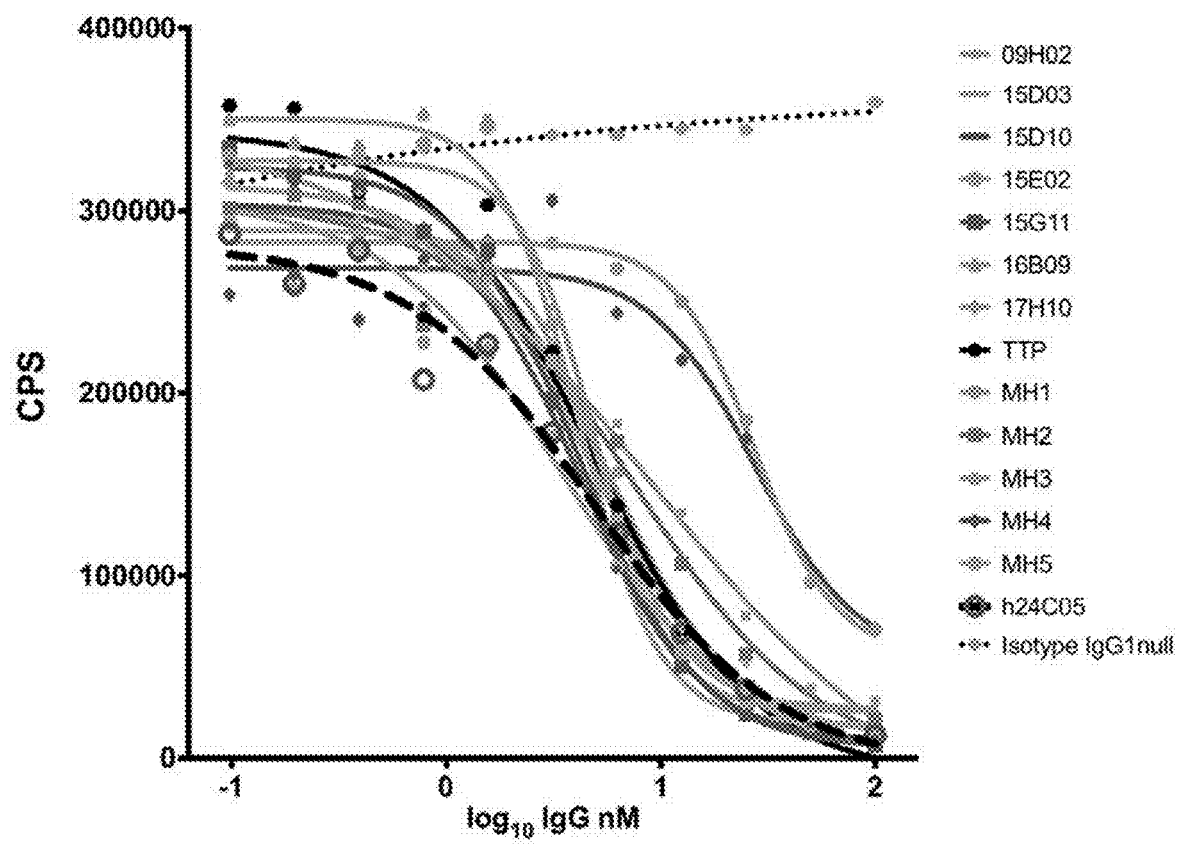

FIG. 4. Epitope competition analysis of IgG1 null proteins in Alphascreen. Anti-ERBB3 IgG1null clones were applied in an epitope competition assay using Alphascreen technology. In this assay, library-derived and designer IgGs were analysed for their retention of the h24C05 epitope by competing for h24C05 IgG1null binding to human ERBB3 protein, in solution. All clones analysed showed strong, concentration-dependent neutralisation of h24C05 binding to ERBB3.

Figure 5A:
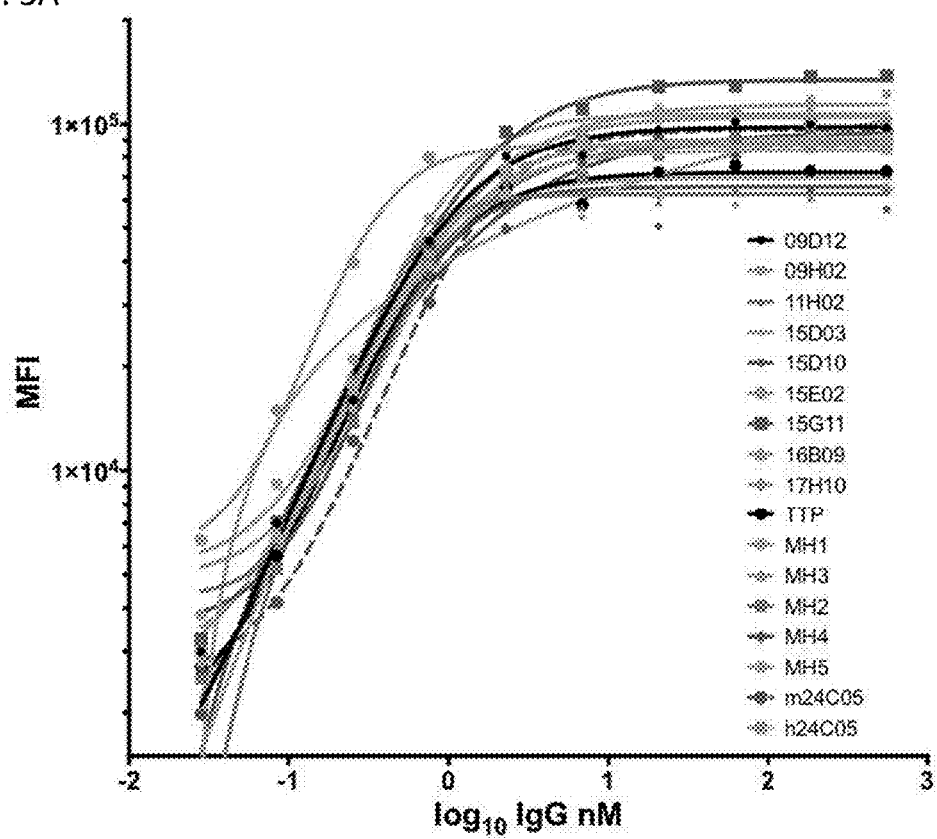
Figure 5B:
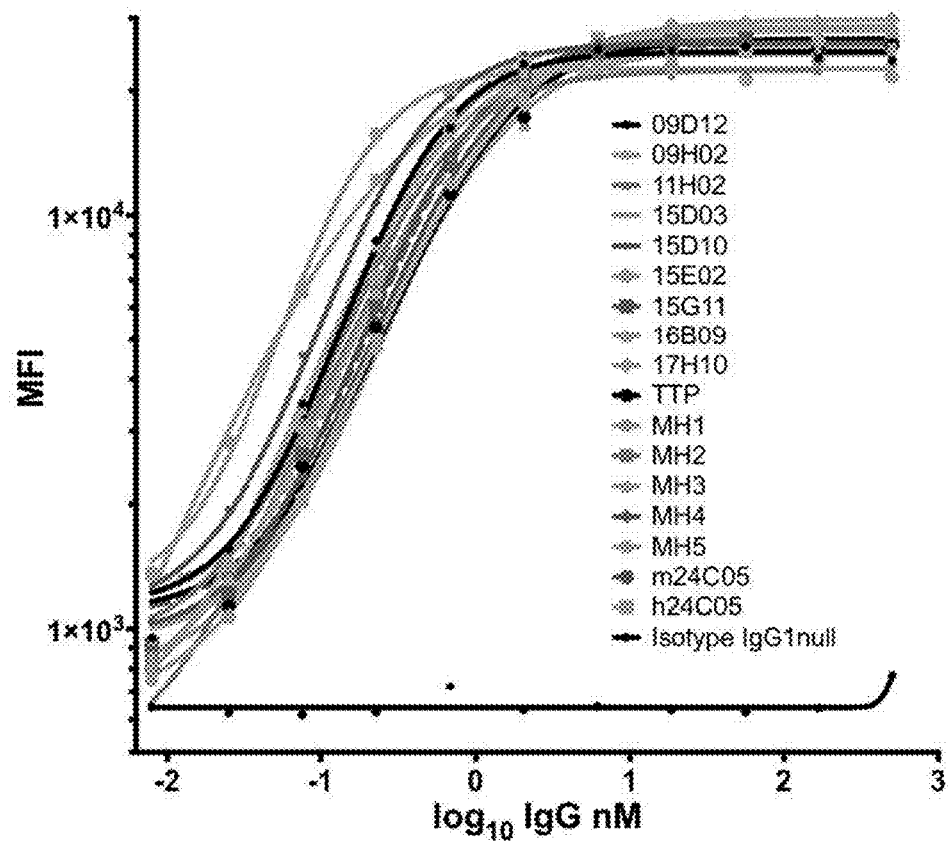

FIG. 5A-FIG. 5B. Flow cytometric binding to human and rhesus ERBB3+ HEK-293 cells for library-derived and primary designer leads. Chimeric and humanized 24C05, library-derived and designer leads in IgG1null format were examined for specific binding on human (FIG. 5A) and rhesus (FIG. 5B) ERBB3-transfected HEK-293 cells. IgGs were tested at concentrations ranging from 0.008-500 nM. Concentration-dependent binding was observed against both human and rhesus cell lines for all ERBB3-specific antibodies but not isotype controls. No binding signals above background were observed against wild type HEK-293 cells.

Figure 6A:
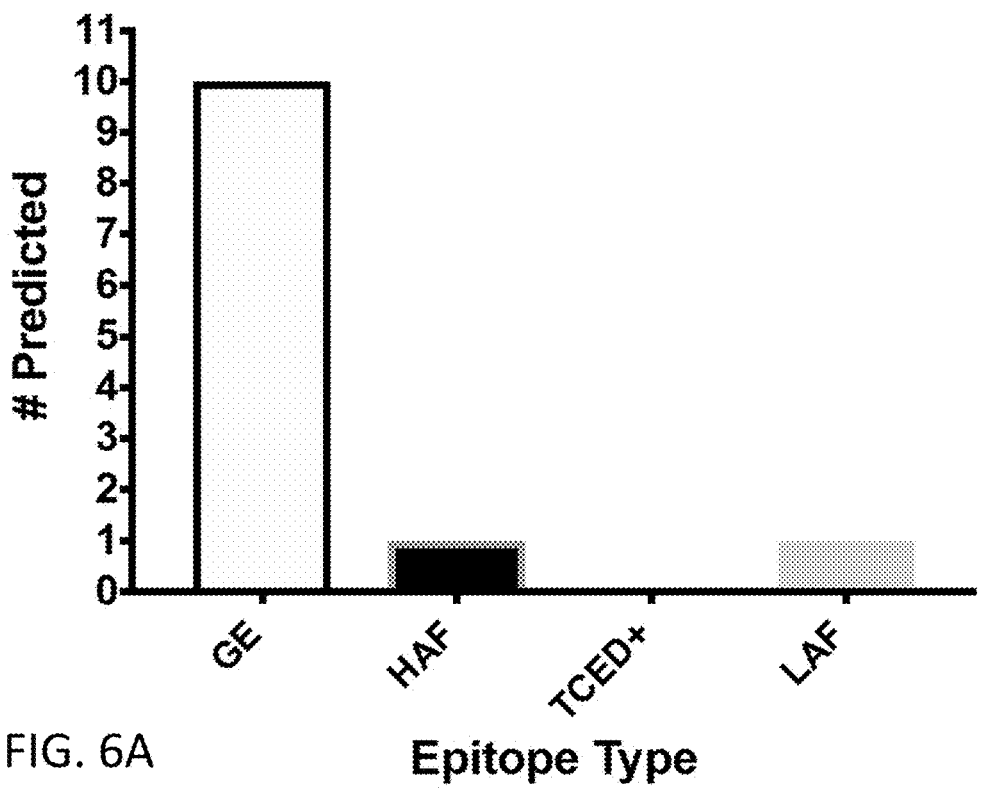
Figure 6B:
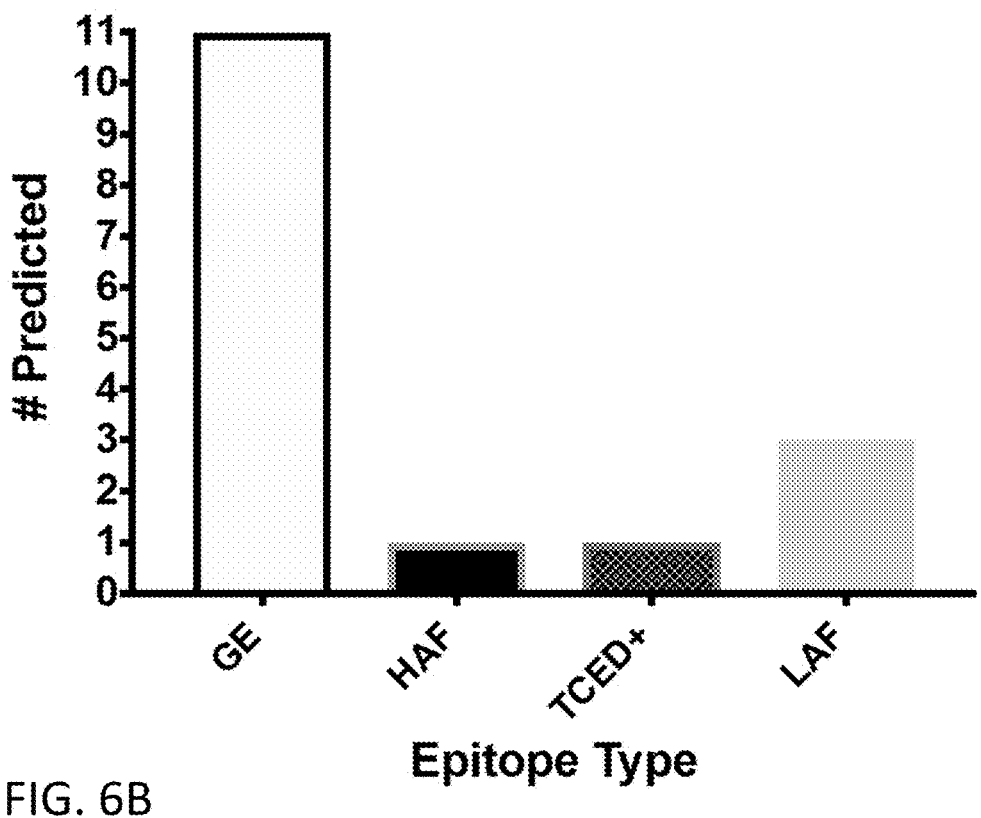

FIG. 6A-FIG. 6B. T cell epitope peptide content in lead antibody v-domains. The v-domains of h24C05 (FIG. 6A) and 15G11 (FIG. 6B) antibodies were examined for the presence of Germline (GE), High Affinity Foreign (HAF), Low Affinity Foreign (LAF) and TCED+ T cell receptor epitopes. Both the VH and VL domains of each antibody were found to contain multiple high-risk human T cell epitopes. In 15G11, despite having germline frameworks and multiple human germline residue changes in the CDRs, the high-risk epitope content was significantly increased in comparison to h24C05, rather than the expected reduction.

Figure 7A:
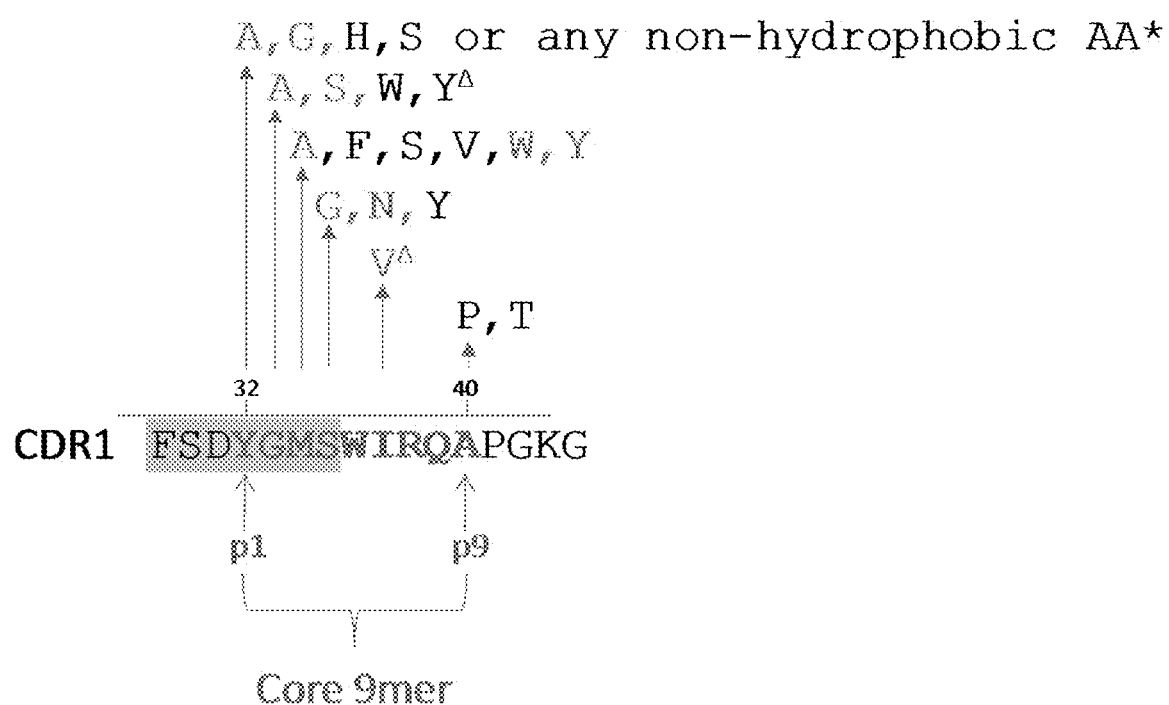
Figure 7B:
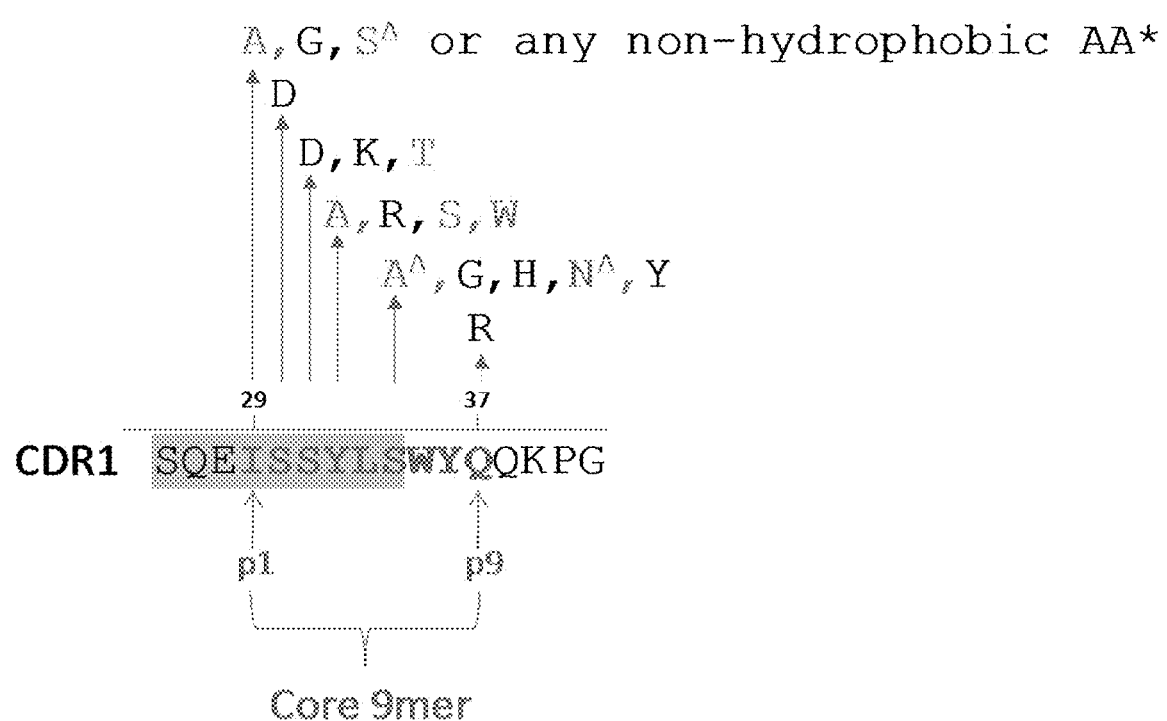
Figure 7C:
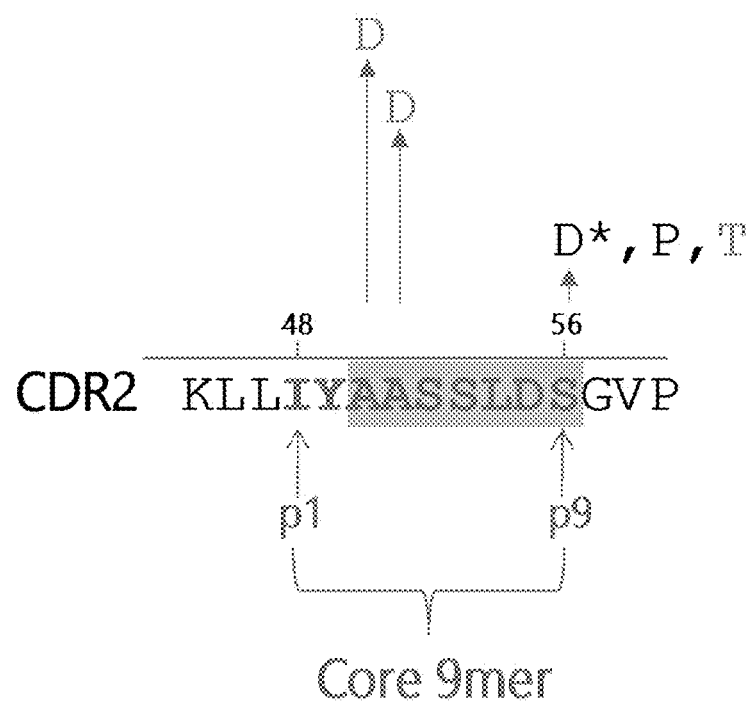
Figure 7D:
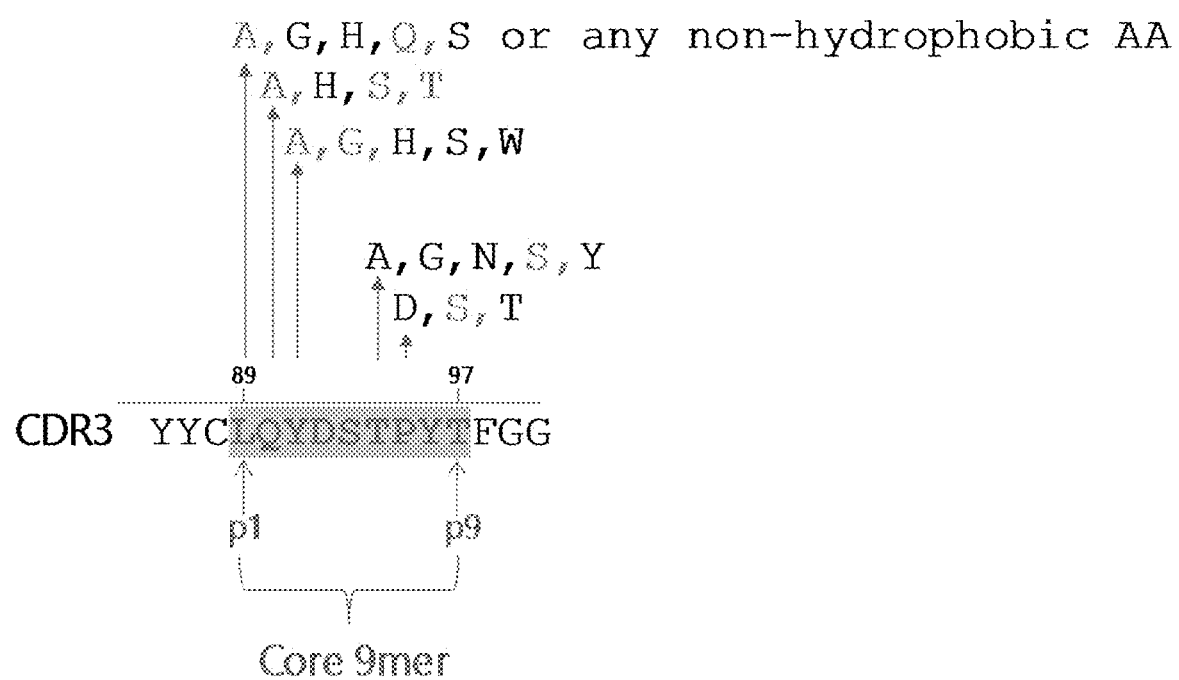

FIG. 7A-FIG. 7D. In silico disruption of T cell epitope peptide content in lead antibody v-domains. The v-domains High Affinity Foreign (HAF), Low Affinity Foreign (LAF) and TCED+ T cell receptor epitopes found in 15G11 were targeted for ablation. In silico mutagenesis analyses were performed to identify non-germline amino acid changes that might maintain antibody binding function but ablate one or more 9-mer peptide epitopes. There analyses were performed for peptides found in the HCDR-1 (FIG. 7A), LCDR-1 (FIG. 7B), LCDR-2 (FIG. 7C) and LCDR-3 (FIG. 7D). Residues are numbered according to the Kabat numbering scheme, the 9-mer peptide sequence is highlighted and p1 and p9 positions indicated. Favoured epitope disrupting mutations are indicated above arrows in grey, disfavoured in black. A delta symbol next to an amino acid one-letter abbreviation means that this mutation would render the new peptide a germ line (GE) peptide. An asterisk next to an amino acid one-letter abbreviation refers to a disfavoured mutation because the use of that residue would create a new isomerisation development risk motif (DG). FIG. 7A shows SEQ ID NO:257. FIG. 7B shows SEQ ID NO:258. FIG. 7C shows SEQ ID NO:259. FIG. 7D shows SEQ ID NO:260.

Figure 8A:
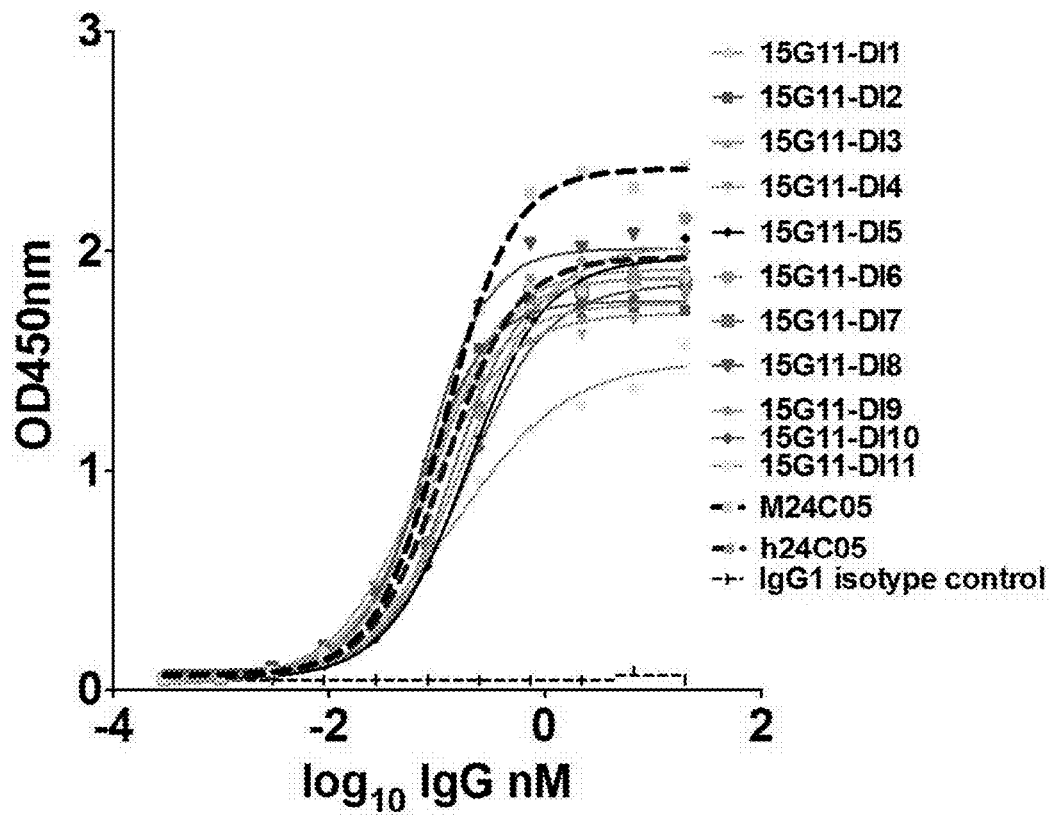
Figure 8B:
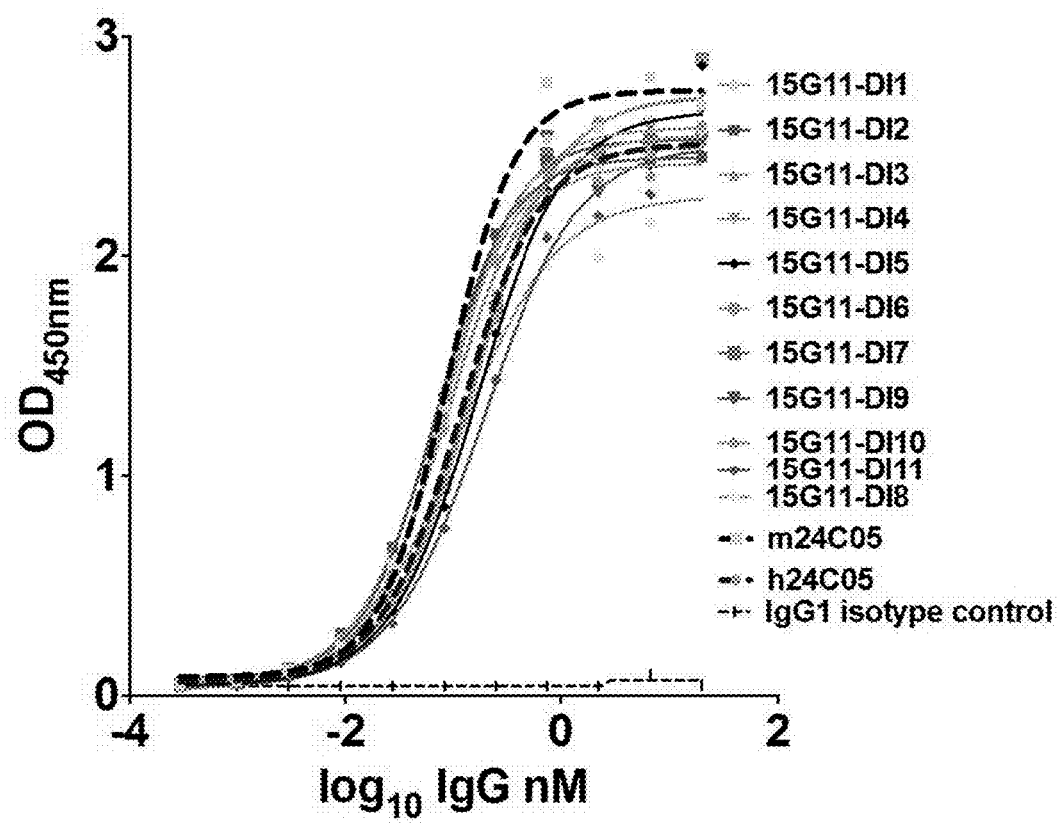

FIG. 8A-FIG. 8B. Direct titration ELISA for 15G11-DI IgGs binding to human and rhesus ErbB3 proteins. Chimeric and humanized 24C05, isotype control IgG1 and 15G11-DI1 to DI11 clones in human IgG1 format were titrated (in nM) in a direct binding ELISA against human (FIG. 8A) and rhesus (FIG. 8B) ERBB3-Fc proteins. All clones other than Isotype IgG1 control demonstrated binding activity against both orthologs of ERBB3.

Figure 9:
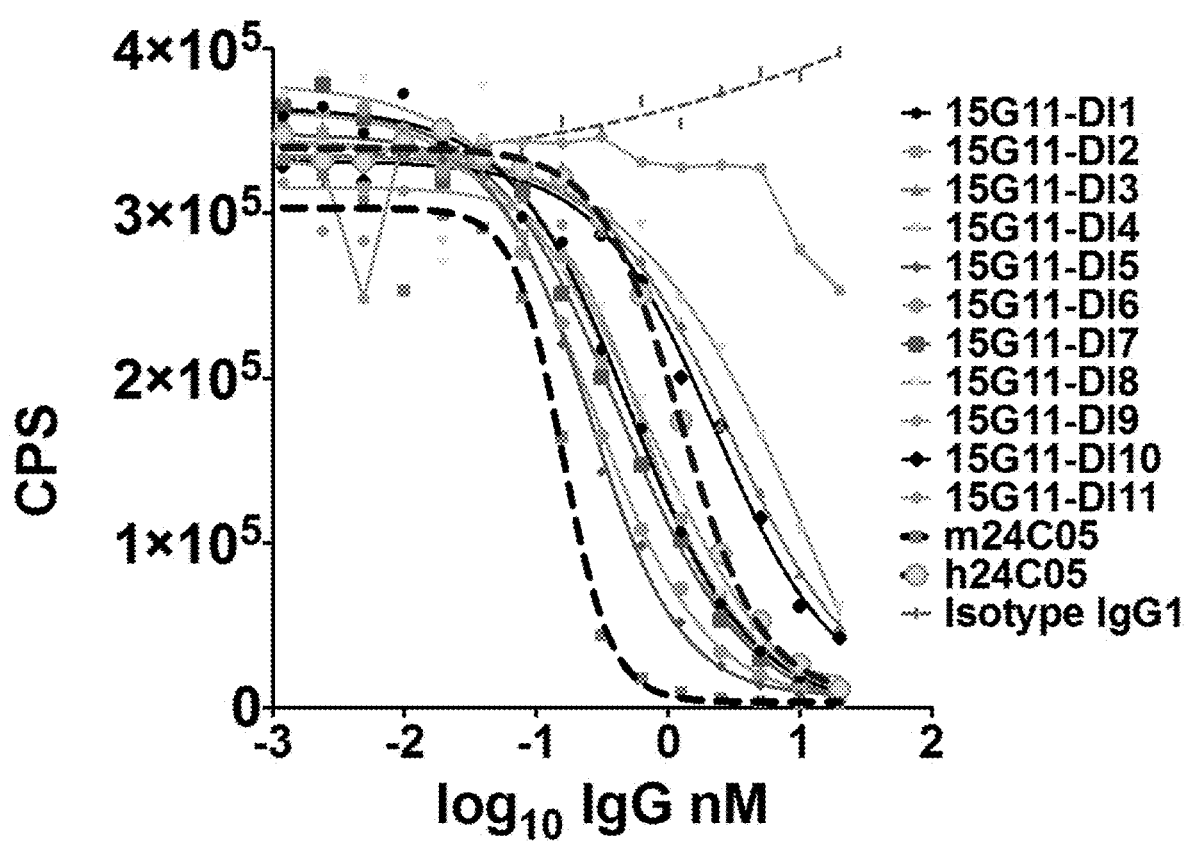

FIG. 9. Epitope competition analysis of IgG1 proteins in Alphascreen. Chimeric and humanized 24C05, isotype control IgG1 and 15G11-DI1 to DI11 clones in human IgG1 format were applied in an epitope competition assay using Alphascreen technology. In this assay, IgGs were analysed for their retention of the same functional epitope as h24C05 by competing for h24C05 IgG1 binding to human ERBB3 protein, in solution. All clones analysed showed strong, concentration-dependent neutralisation of h24C05 binding to ERBB3, with the exception of 15G11-DI11.

Figure 10A:
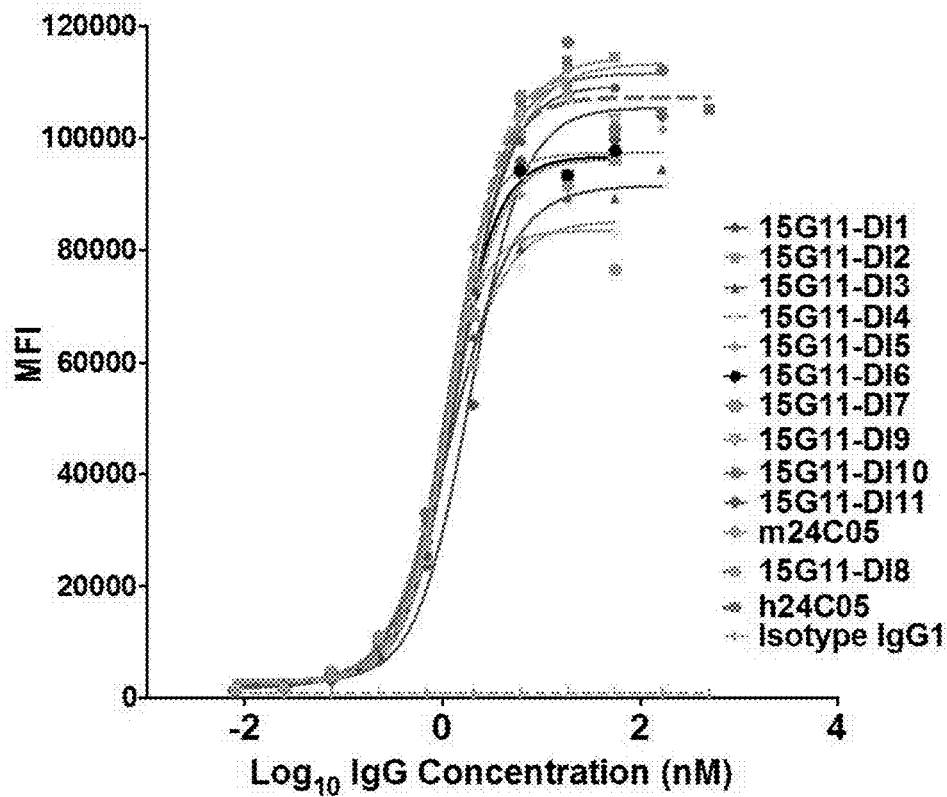
Figure 10B:
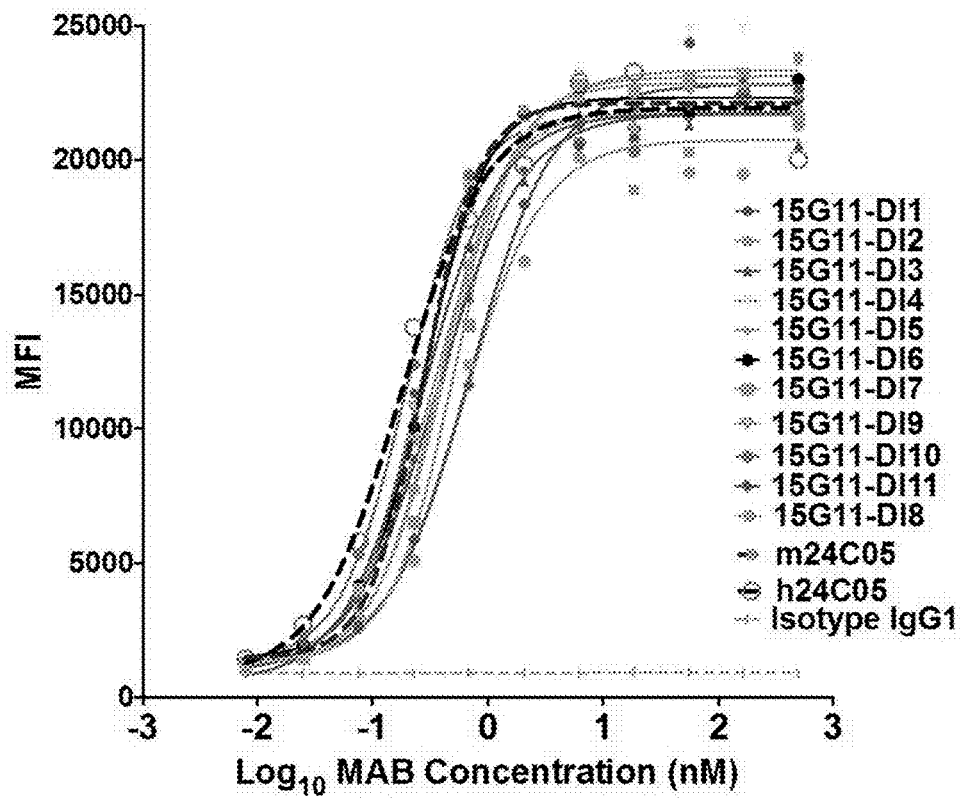

FIG. 10A-FIG. 10B. Flow cytometric binding to human and rhesus ERBB3+ HEK-293 cells for library-derived and primary designer leads. Chimeric and humanized 24C05, isotype control IgG1 and 15G11-DI1 to DI11 clones in human IgG1 format were examined for specific binding on human (FIG. 10A) and rhesus (FIG. 10B) ERBB3-transfected HEK-293 cells. IgGs were tested at concentrations ranging from 0.008-500 nM. Concentration-dependent binding was observed against both human and rhesus transfected cells for all ERBB3-specific antibodies but not isotype controls.

Figure 11:
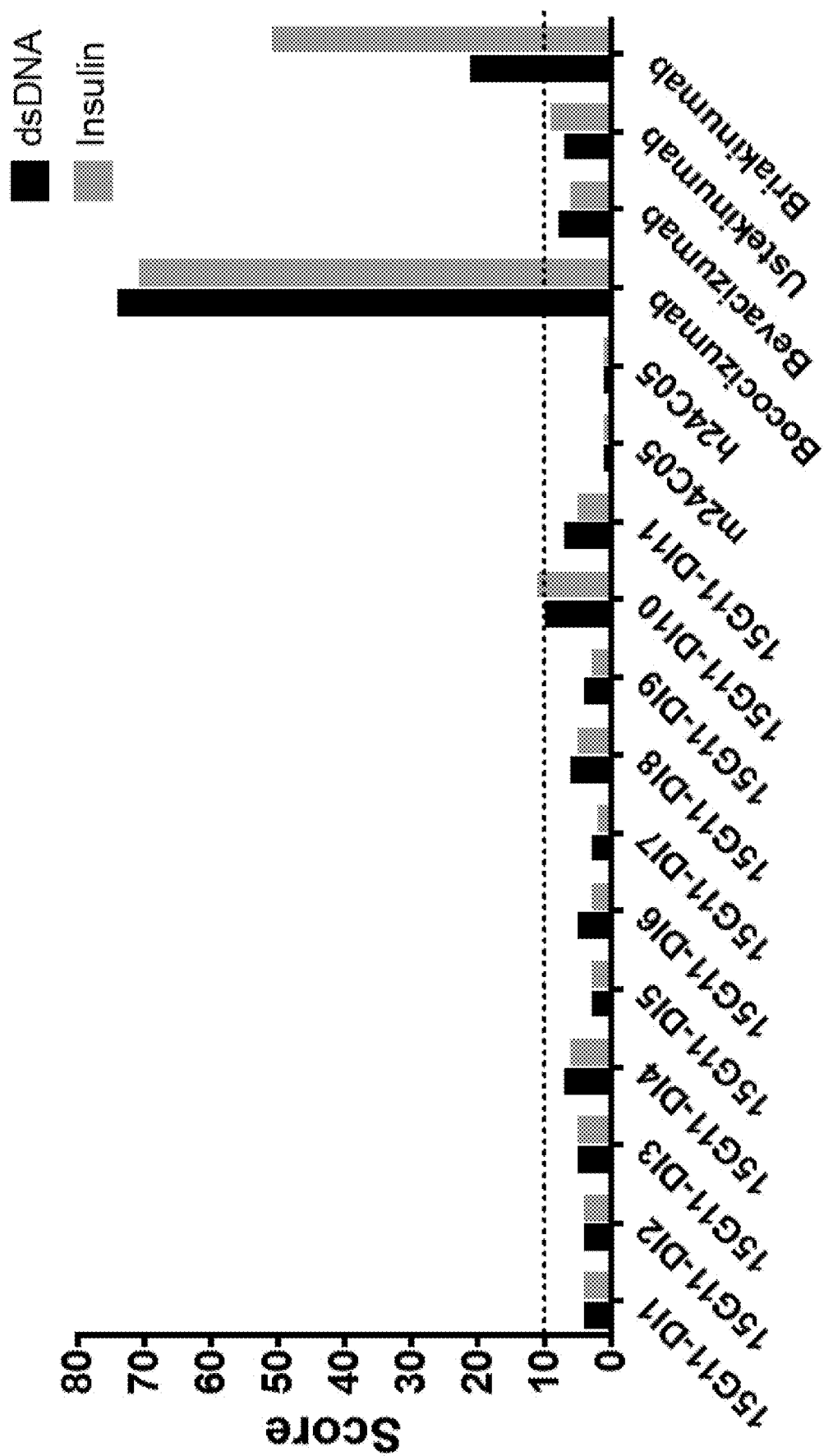
Figure 12A:
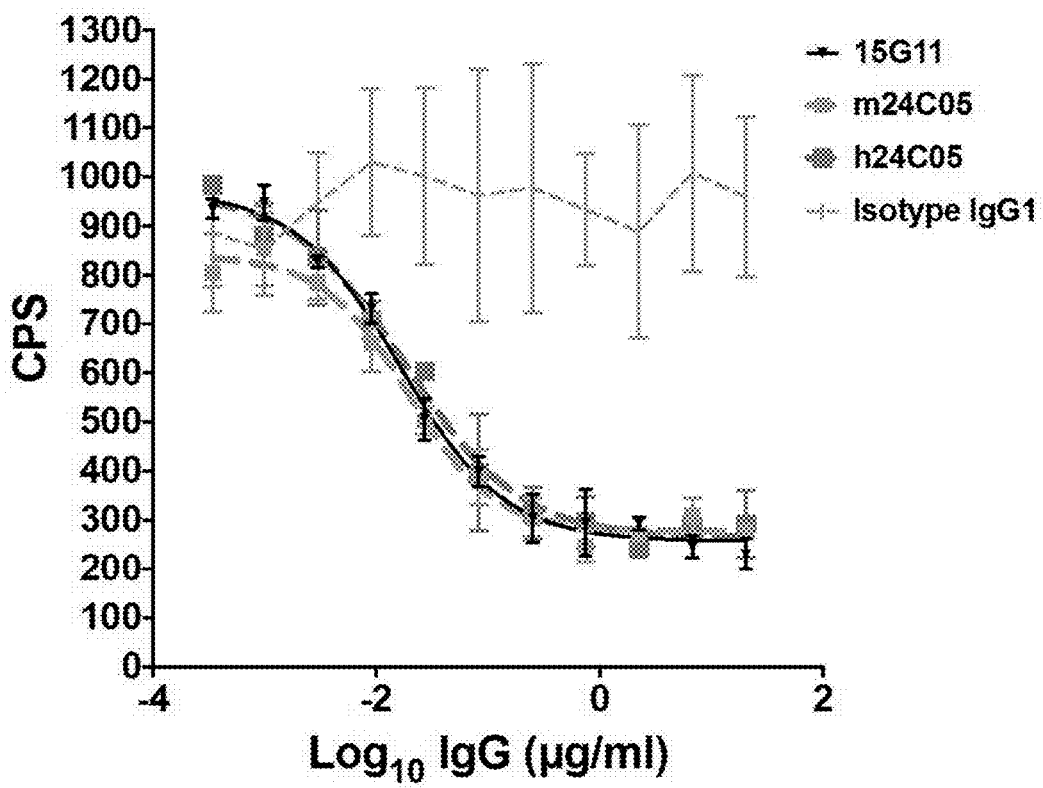
Figure 12B:
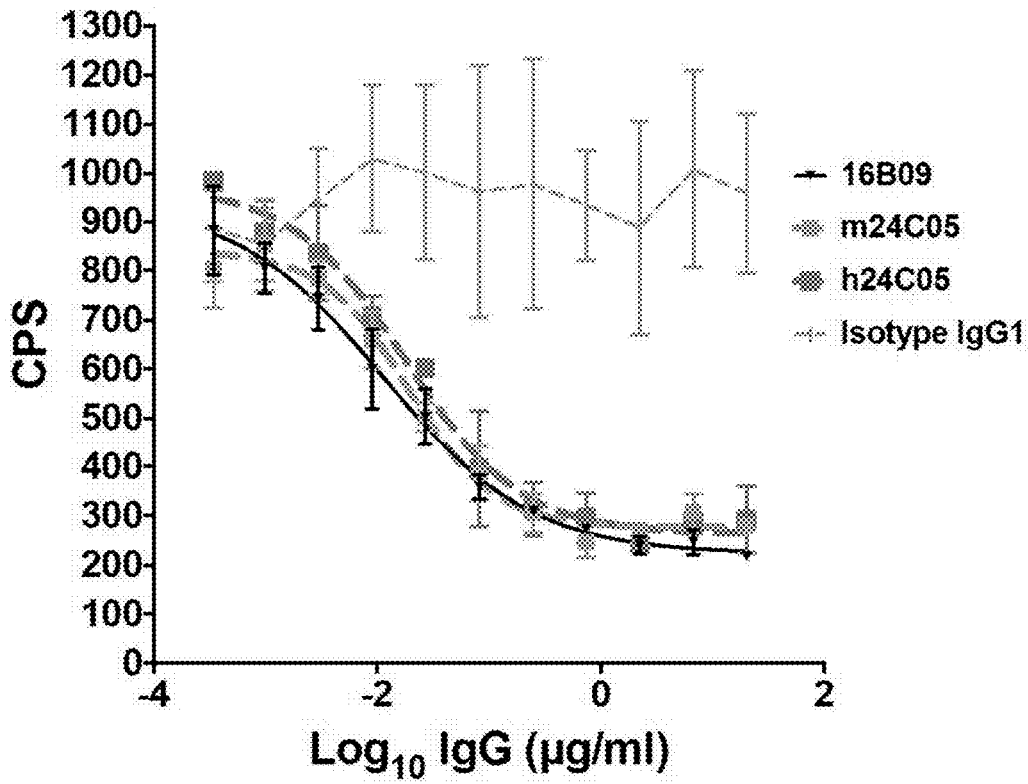
Figure 12C:
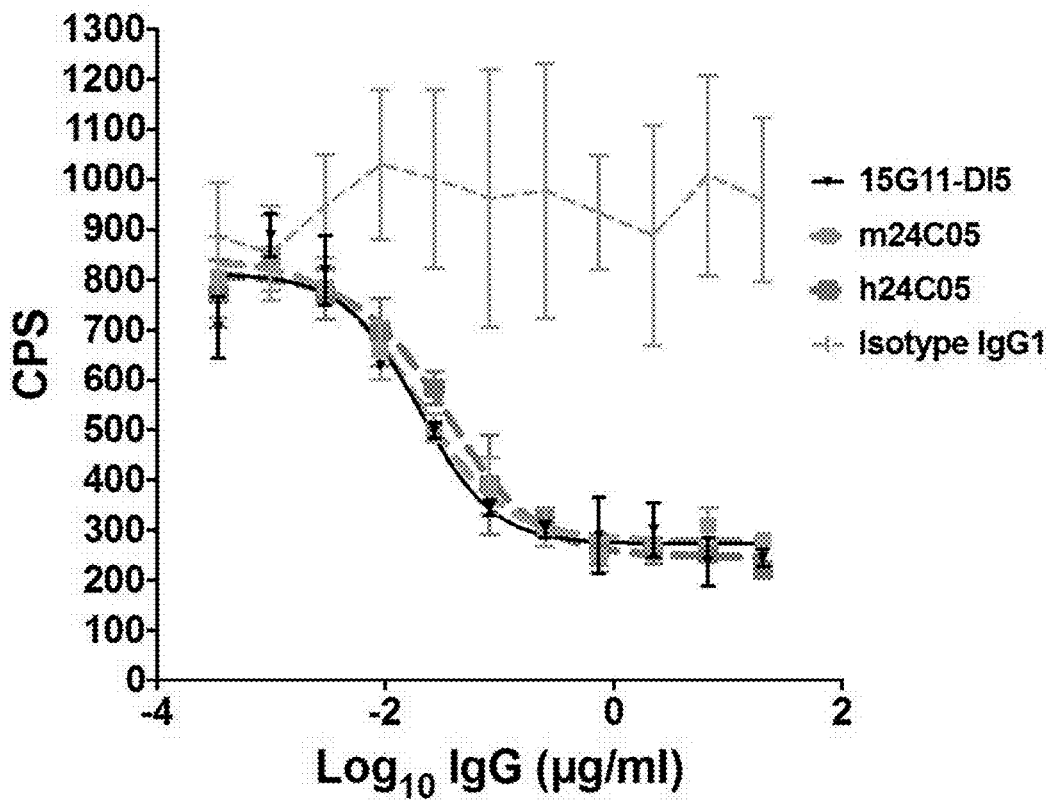
Figure 12D:
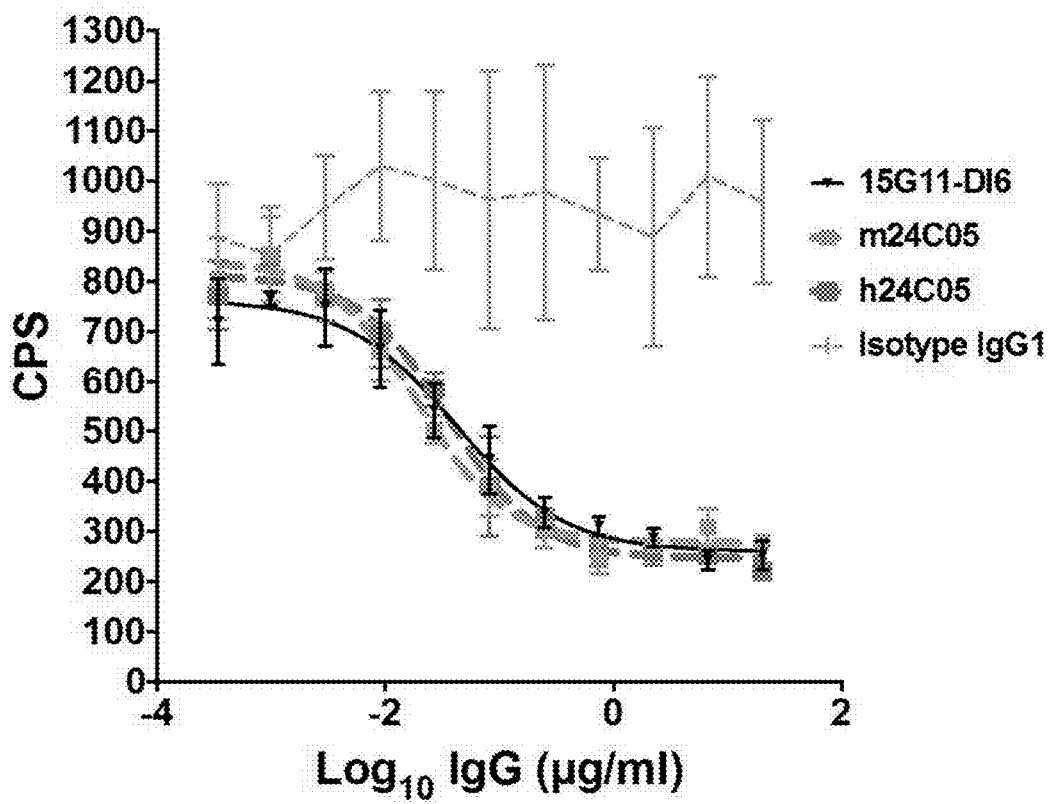
Figure 12E:
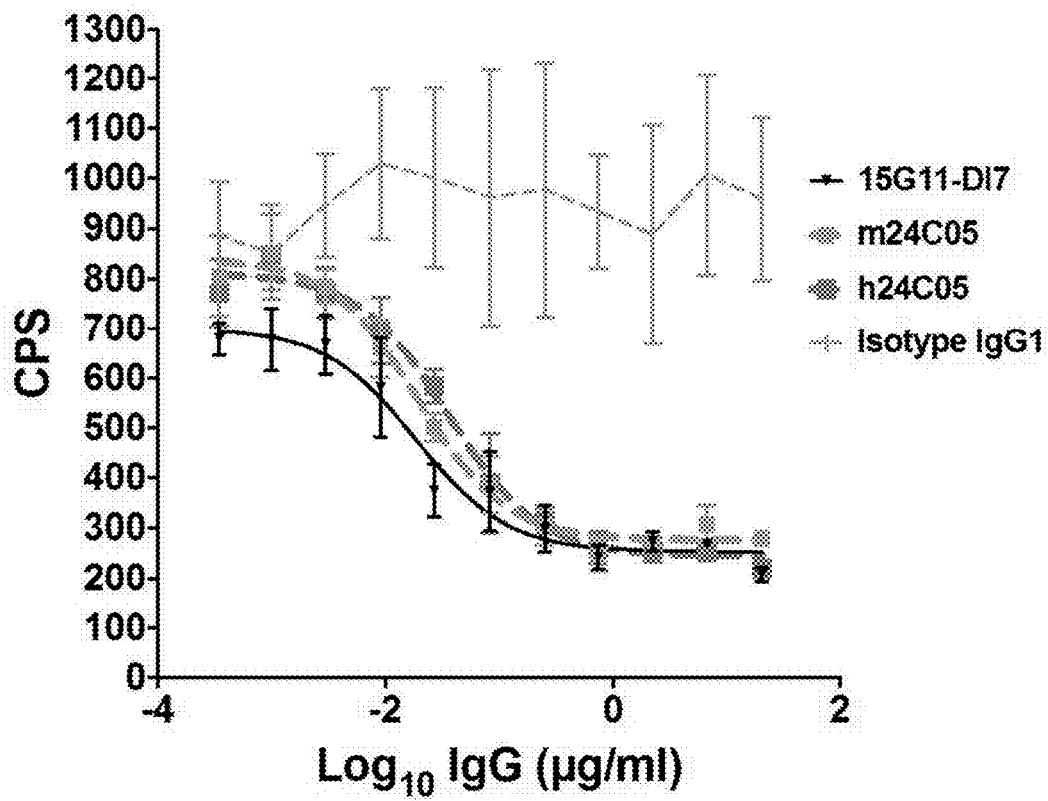
Figure 12F:
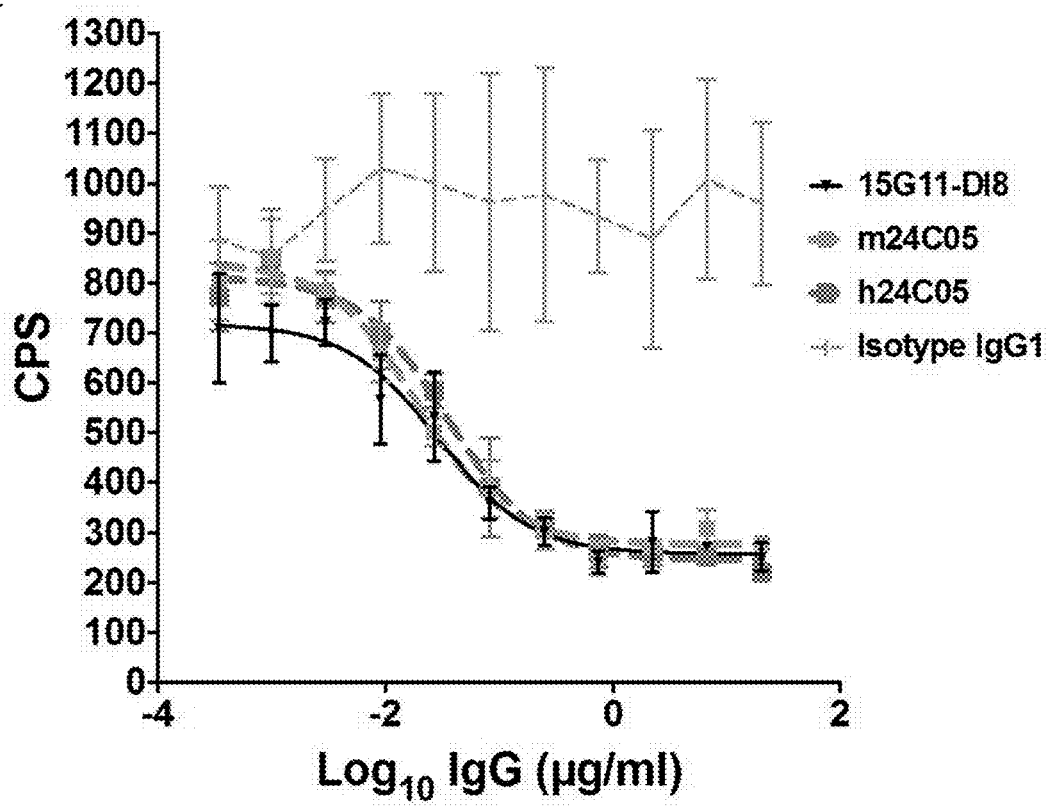
Figure 12G:
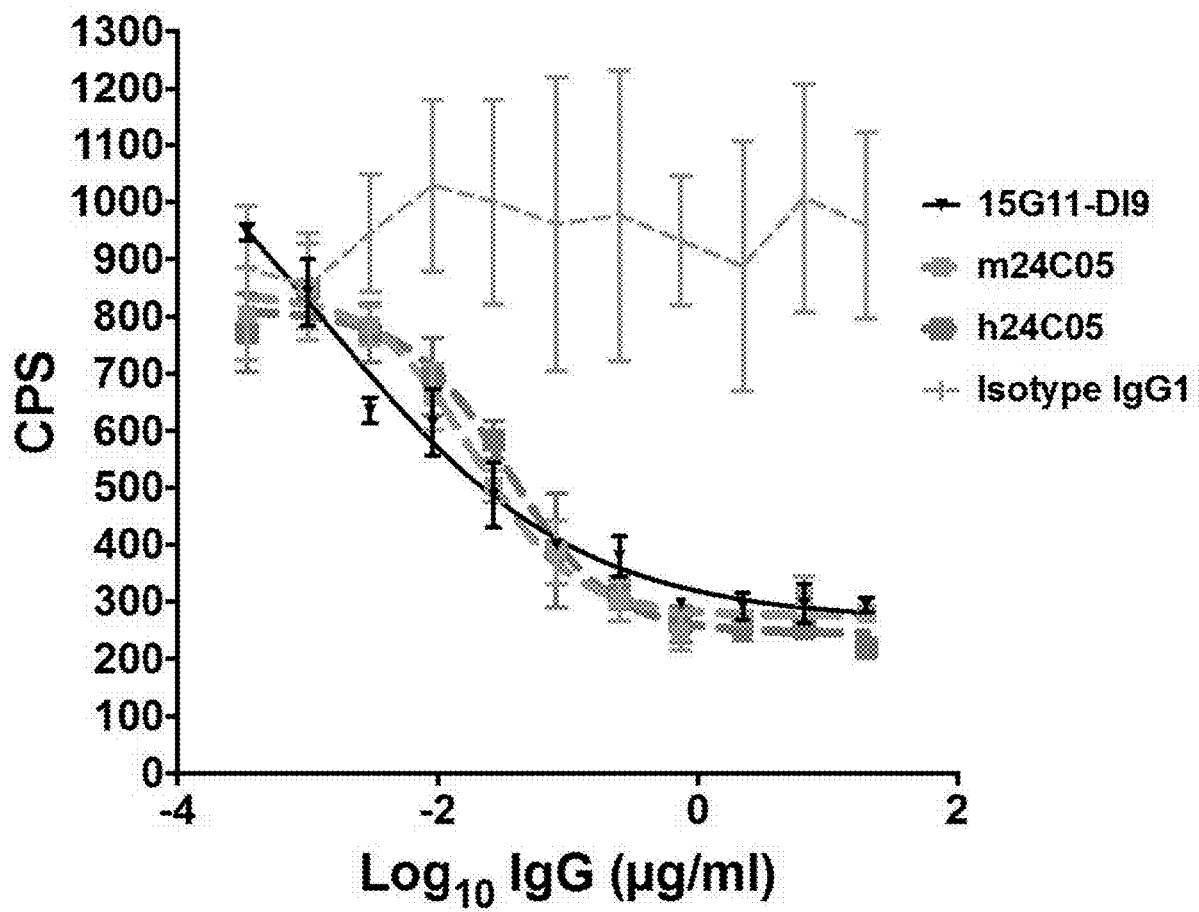

FIG. 11. Development risk ELISAs. Chimeric and humanized 24C05, isotype control IgG1, clinical-stage control antibodies, and 15G11-DI1 to DI11 clones in human IgG1 format were examined for nonspecific binding to the negatively charged biomolecules Insulin and double-stranded DNA (dsDNA). All lead clones demonstrated binding scores below 10 (15G11-DI10 being an exception), significantly lower than either of the negative control IgG1 Ustekinumab and Bevacizumab analogs. Strong off-target binding to insulin or dsDNA, as observed for Bococizumab and Briakinumab analogues, has been shown to be a high-risk indicator of poor pharmacokinetics of therapeutic antibodies.

FIG. 12A-FIG. 12G. Cell-based ErbB2-ErbB3 antagonism assay. Chimeric and humanized 24C05, isotype control IgG1 and clones 15G11 (FIG. 12A), 16B09 (FIG. 12B), 15G11-DI5 (FIG. 12C), 15G11-DI6 (FIG. 12D), 15G11-DI7 (FIG. 12E), 15G11-DI8 (FIG. 12F), and 15G11-DI9 (FIG. 12G) in human IgG1 format were titrated in a human ErbB3 signalling reporter assay (DiscoverX PathHunter eXpress ErbB2-ErbB3 assay, performed according to manufacturer's instructions). All clones other than the Isotype control induced strong, concentration-dependent ErbB3 antagonism, with highly similar potencies to h24C05.

Figure 13:
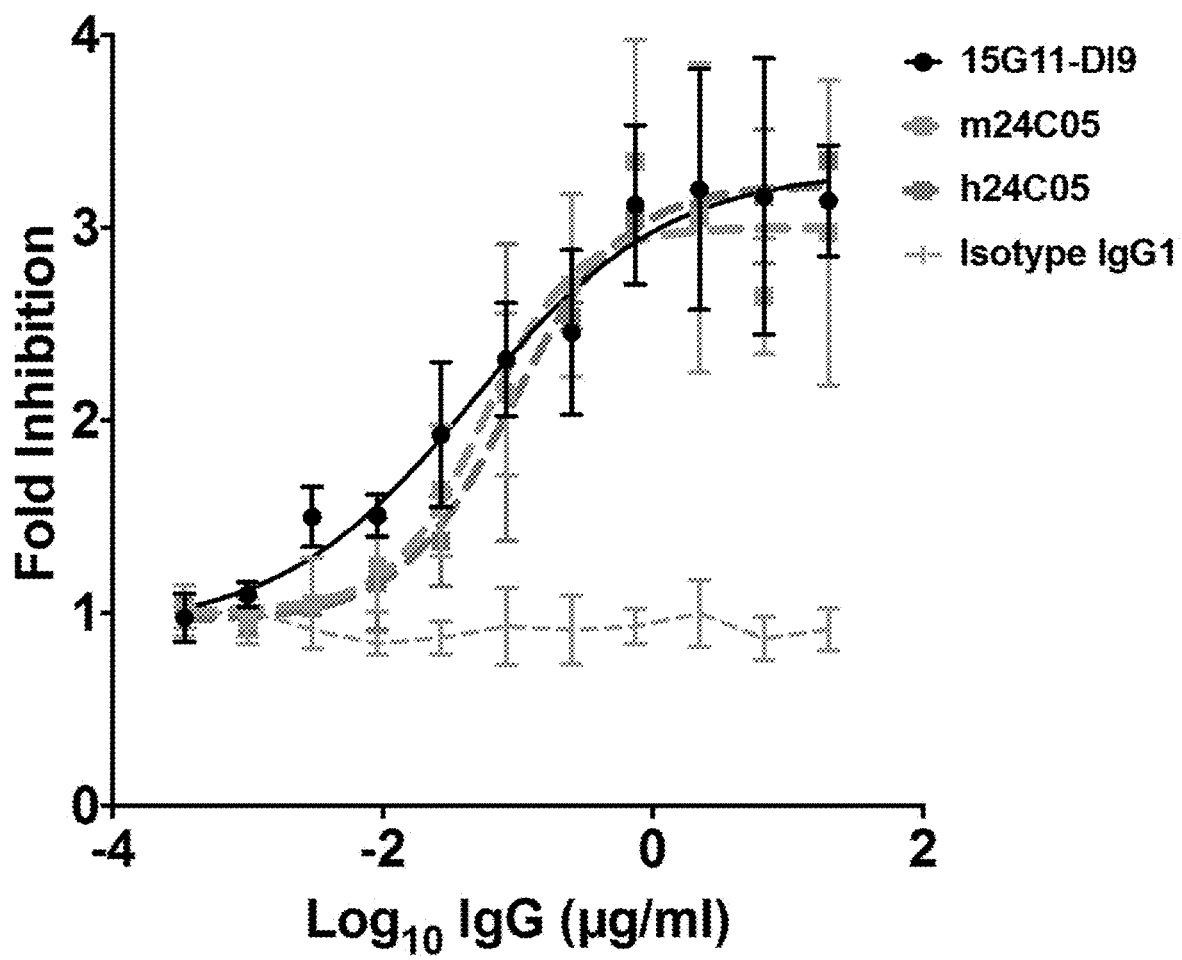
Figure 14A:
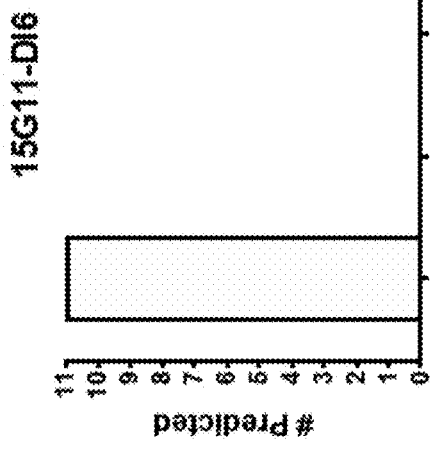
Figure 14B:
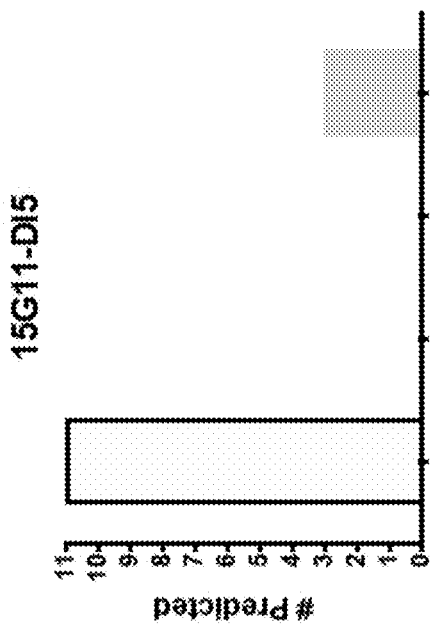
Figure 14C:
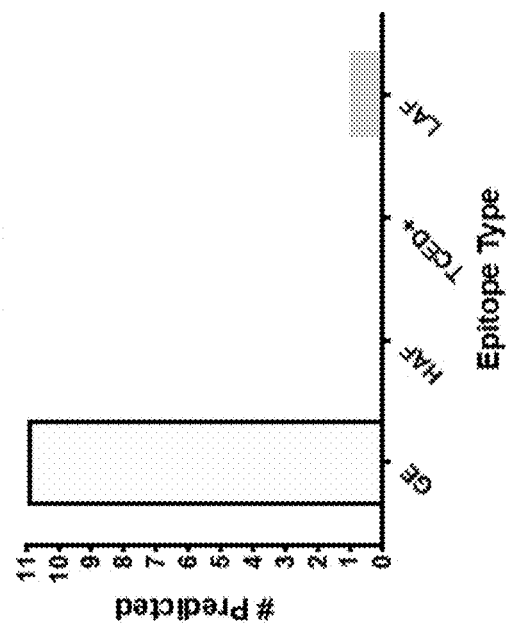
Figure 14D:
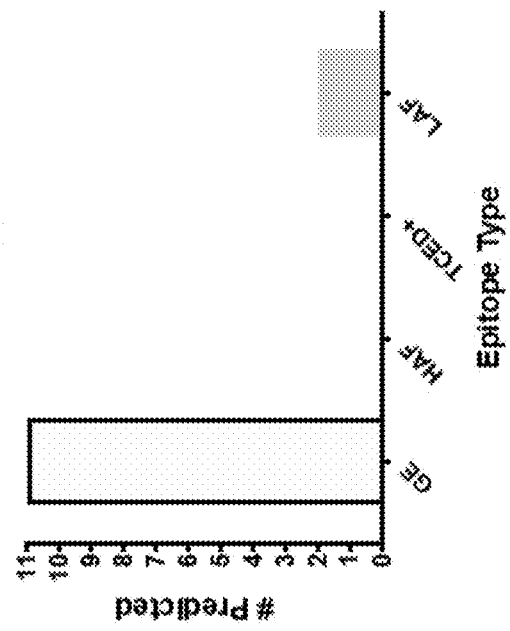
Figure 14E:
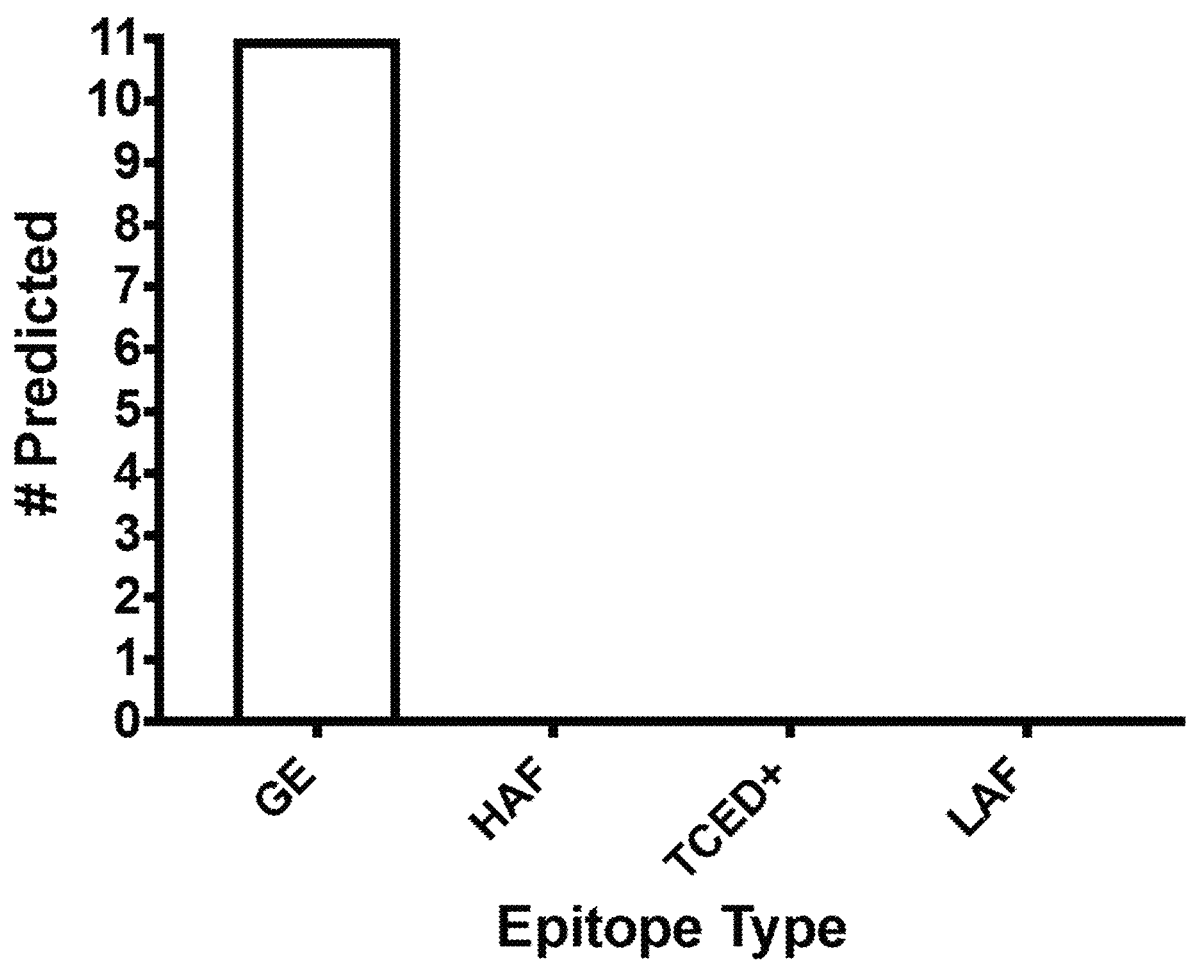

FIG. 13. Cell-based ErbB2-ErbB3 antagonism assay for 15G11-DI9. Chimeric and humanized 24C05, isotype control IgG1 and clone 15G11-DI9 in human IgG1 format were titrated in a human ErbB3 signalling reporter assay (DiscoverX PathHunter eXpress ErbB2-ErbB3 assay, performed according to manufacturer's instructions). All clones other than the Isotype control induced strong, concentration-dependent ErbB3 antagonism, as evidenced by fold inhibition of signal.

FIG. 14A-FIG. 14E. T cell epitope peptide content in lead antibody v-domains. The v-domains of 15G11-DI5 (FIG. 14A), 15G11-DI6 (FIG. 14B), 15G11-DI7 (FIG. 14C), 15G11-DI8 (FIG. 14D) and 15G11-DI9 (FIG. 14E) antibodies were examined for the presence of Germline (GE), High Affinity Foreign (HAF), Low Affinity Foreign (LAF) and TCED+ T cell receptor epitopes. In all lead clones, the high-risk epitope content was progressively reduced, and germline epitope content maintained from 15G11-DI5 to 15G11-DI9, with 15G11-DI9 containing no predicted foreign epitopes at all, coupled with high GE content, suggesting that this clone may be fully non-immunogenic in man.

DETAILED DESCRIPTION OF THE INVENTION

According to a first aspect of the invention, there is provided an antibody molecule which specifically binds to human ERBB3 and optionally also to rhesus monkey ERBB3, or an antigen-binding portion thereof, wherein the antibody molecule or antigen-binding portion comprises a heavy chain variable region with:

an HCDR1 having amino acids in sequence in the following order: G-F-T-F-S-D-Y-G or any amino acid (such as S)-M-S (SEQ ID NO:1);

an HCDR2 having amino acids in sequence in the following order: V-S-T-I-S-D-G or any amino acid (such as S, D)-G-T or a conservative substitution of T (such as S)-Y or any amino acid (such as T)-T or any amino acid (such as I)-Y-Y-P or any amino acid (such as A)-D-N or a conservative substitution of N (such as S)-V-K-G (SEQ ID NO:2); and an HCDR3 having amino acids in sequence in the following order: E or any amino acid (such as M)-W or any amino acid (such as F, L, M, Q or Y)-G-D-Y or any amino acid (such as A, D, E, H, L, M, N, Q, S, T or W)-D-G-F or any amino acid (such as I, L, W, Y)-D-Y or any amino acid (such as A, D, E, F, H, I, K, L, M, N, Q, R, S, V, W) (SEQ ID NO:3).

In some aspects an anti-ERBB3 antibody or antigen-binding portion provided herein specifically binds to a ERBB3 protein comprising or consisting of SEQ ID NO:246 or SEQ ID NO:247. In some aspects an anti-ERBB3 antibody or antigen-binding portion provided herein specifically binds to a ERBB3 protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:246 or SEQ ID NO:247.

In aspects of the invention, the HCDR1 of the antibody molecule or antigen-binding portion may exclude the sequence GFTFSDYAMS (SEQ ID NO:4; 24C05 murine/humanized antibody HCDR1 disclosed in WO2011136911A2; US20110256154A1), the HCDR2 of the antibody molecule or antigen-binding portion may exclude the sequence VSTISDGGTYTYYPDNVKG (SEQ ID NO:5; 24C05 murine/humanized antibody HCDR2 disclosed in WO2011136911A2; US20110256154A1), and/or the HCDR3 of the antibody molecule or antigen-binding portion may exclude the sequence EWGDYDGFDY (SEQ ID NO:6; 24C05 murine/humanized antibody HCDR3 disclosed in WO2011136911A2; US20110256154A1).

The antibody molecule or antigen-binding portion may further comprise a light chain variable region with:

an LCDR1 having amino acids in sequence in the following order: R-A-S-Q-E or any amino acid (such as S, I, N)-I-S-G or a conservative substitution of G (such as S, T)-Y-L-S or a conservative substitution of S (such as N) (SEQ ID NO:7); an LCDR2 having amino acids in sequence in the following order: A or any amino acid (such as E)-A-S-T or a conservative substitution of T (such as S, N)-L-D or any amino acid (such as H, K, Q)-S or T (SEQ ID NO:8); and an LCDR3 having amino acids in sequence in the following order: L or any amino acid (such as Q)-Q-Y or any amino acid (such as S)-D or any amino acid (such as Y)-S-Y or any amino acid (such as T, S)-P or any amino acid (such as H)-Y or any amino acid (such as L)-T (SEQ ID NO:9).

In aspects of the invention, the LCDR1 of the antibody molecule or antigen-binding portion may exclude the sequence RASQEISGYLS (SEQ ID NO:10; 24C05 murine/humanized antibody LCDR1 disclosed in WO2011136911A2; US20110256154A1), and/or the LCDR2 of the antibody molecule or antigen-binding portion may exclude the sequence AASTLDS (SEQ ID NO:11; 24C05 murine/humanized antibody LCDR2 disclosed in WO2011136911A2; US20110256154A1), and/or the LCDR3 of the antibody molecule or antigen-binding portion may exclude the sequence LQYDSYPYT (SEQ ID NO:12; 24C05 murine/humanized antibody LCDR3 disclosed in WO2011136911A2; US20110256154A1).

In some aspects, disclosed herein is an anti-ERBB3 antibody or an antigen-binding portion thereof, wherein the antibody comprises a heavy chain variable (VH) region and a light chain variable (VL) region, wherein (a) the HCDR1 comprises the amino acid sequence G-F-T-F-S-D-Y-$X_1$-M-S, wherein $X_1$ is G or any other amino acid (for example, S) (SEQ ID NO:1);

(b) the HCDR2 comprises V-S-T-I-S-D-$X_1$-G-$X_2$-$X_3$-$X_4$-Y-Y-$X_5$-D-$X_6$-V-K-G, wherein $X_1$ is G or any other amino acid (for example, S or D), $X_2$ is T or a conservative substitution of T (for example, S), $X_3$ is Y or any other amino acid (for example, T), $X_4$ is T or any other amino acid (for example, I), $X_5$ is P or any other amino acid (for example, A), and $X_6$ is N or a conservative substitution of N (for example, S) (SEQ ID NO:2);

(c) the HCDR3 comprises $X_1$-$X_2$-G-D-$X_3$-D-G-$X_4$-D-$X_5$, wherein $X_1$ is E or any other amino acid (for example, M), $X_2$ is W or any other amino acid (for example, F, L, M, Q or Y), $X_3$ is Y or any other amino acid (for example, A, D, E, H, L, M, N, Q, S, T or VV), $X_4$ is F or any other amino acid (for example, I, L, W or Y), and $X_5$ is Y or any other amino acid (for example, A, D, E, F, H, I, K, L, M, N, Q, R, S, V or W) (SEQ ID NO:3);

(d) the LCDR1 comprises R-A-S-Q-$X_1$-I-S-$X_2$-Y-L-$X_3$, wherein $X_1$ is E or any other amino acid (for example, S, I or N), $X_2$ is G or a conservative substitution of G (for example, S or T), and $X_3$ is S or a conservative substitution of S (for example, N) (SEQ ID NO:7);

(e) the LCDR2 comprises $X_1$-A-S-$X_2$-L-$X_3$-S, wherein $X_1$ is A or any other amino acid (for example, E), $X_2$ is T or a conservative substitution of T (for example, S or N), and $X_3$ is or D any other amino acid (for example, H, K or Q) (SEQ ID NO:8); and (f) the LCDR3 comprises $X_1$-Q-$X_2$-$X_3$-S-$X_4$-$X_5$-$X_6$-T, wherein $X_1$ is L or any other amino acid (for example, Q), $X_2$ is Y or any other amino acid (for example, S), $X_3$ is D or any other amino acid (for example, Y), $X_4$ is Y or any other amino acid (for example, T or S), $X_5$ is P or any other amino acid (for example, H), and $X_6$ is Y or any other amino acid (for example, L) (SEQ ID NO:9). In some aspects, the LCDR2 comprises $X_1$-A-S-$X_2$-L-$X_3$-S (SEQ ID NO:8), wherein the seventh residue in the sequence is a conservative substitution of S (for example, T).

In some aspects, disclosed herein is an anti-ERBB3 antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:1, the HCDR2 is SEQ ID NO:2, the HCDR3 is SEQ ID NO:3, the LCDR1 is SEQ ID NO:7, the LCDR2 is SEQ ID NO:8 and the LCDR3 is SEQ ID NO:9, wherein the heavy chain FR1, FR2, FR3 and FR4 amino acid sequences are the heavy chain FR1, FR2, FR3 and FR4 amino acid sequences in SEQ ID NO: 86 (see Table 2) and wherein the light chain FR1, FR2, FR3 and FR4 amino acid sequences are the light chain FR1, FR2, FR3 and FR4 amino acid sequences in SEQ ID NO: 88 (see Table 2).

As elaborated herein, the present inventors have succeeded for the first time in generating a number of optimized anti-ERBB3 antibody molecules using CDR sequences derived from the murine anti-ERBB3 antibody 24C05 disclosed in WO2011136911A2; US20110256154A1. In embodiments of the present invention, these antibody molecules have been selected to have binding specificity to both human ERBB3 as well as rhesus monkey ERBB3 (to facilitate in vivo studies in an appropriate animal test species). Further refining of the optimized antibody molecules as described herein has provided improved variable domain stability, higher expression yields, and/or reduced immunogenicity.

Preferred optimized anti-ERBB3 antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-ERBB3 binding characteristics and/or other desirable features.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to ERBB3. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-F-T-F-S-D-Y-E/G/H/N/R/S/T/Q/V-M-S (SEQ ID NO:38); the HCDR2 may have the amino acid sequence: V-S-T-I-S-D-G/S/D-G-T/S-Y/T-T/I-Y-Y-P/A-D-N/S-V-K-G (SEQ ID NO:39); and the HCDR3 may have the amino acid sequence: E/M-W/F/L/M/Q/Y-G-D-Y/A/D/E/H/L/M/N/Q/S/T/W-D-G-F/I/L/W/Y-D-Y/A/D/E/F/H/I/K/L/M/N/Q/R/S/V/W (SEQ ID NO:40).

For example, the HCDR1 may have the amino acid sequence: G-F-T-F-S-D-Y-G/S-M-S (SEQ ID NO:41); the HCDR2 may have the amino acid sequence: V-S-T-I-S-D-G/S-G-S-Y/T-T/I-Y-Y-P/A-D-S-V-K-G (SEQ ID NO:42); and the HCDR3 may have the amino acid sequence: E-W/L/Y-G-D-Y-D-G-F-D-Y/E/F/H/N (SEQ ID NO:43).

In the antibody molecule or antigen-binding portion thereof, the LCDR1 may have the amino acid sequence: R-A-S-Q-E/S/I/N-I-S-G/S-Y-L-S/N (SEQ ID NO:44); the LCDR2 may have the amino acid sequence: A/E-A-S-T/S/N-L-D/H/K/Q-S (SEQ ID NO:45); and the LCDR3 may have the amino acid sequence: L/Q-Q-Y/S-D/Y-S-Y/T-P/H-Y/L-T (SEQ ID NO:46). In the antibody molecule or antigen-binding portion thereof, the LCDR1 may have the amino acid sequence: R-A-S-Q-E/S/I/N-I-S-G/S/T-Y-L-S/N; the LCDR2 may have the amino acid sequence: A/E-A-S-T/S/N-L-D/H/K/Q-S/T; and the LCDR3 may have the amino acid sequence: L/Q-Q-Y/S-D/Y-S-Y/T/S-P/H-Y/L-T.

For example, the LCDR1 may have the amino acid sequence: R-A-S-Q-E/S-I-S-G/S-Y-L-S/N (SEQ ID NO:47); the LCDR2 may have the amino acid sequence: A-A-S-T/S-L-D/Q-S (SEQ ID NO:48); and the LCDR3 may have the amino acid sequence: L-Q-Y-D/Y-S-T-P-Y/L-T (SEQ ID NO:49). For example, the LCDR1 may have the amino acid sequence: R-A-S-Q-E/S-I-S-G/S/T-Y-L-S/N; the LCDR2 may have the amino acid sequence: A-A-S-T/S-L-D/Q-S/T; and the LCDR3 may have the amino acid sequence: L-Q-Y-D/Y-S-T/S-P-Y/L-T.

In specific embodiments of the invention, the antibody molecule or antigen-binding portion may comprise:

(a) the amino acid sequences RASQSISSYLS (SEQ ID NO:16; LCDR1), AASTLQS (SEQ ID NO:26; LCDR2), LQYDSTPLT (SEQ ID NO:18; LCDR3), GFTFSDYGMS (SEQ ID NO:13; HCDR1), VSTIS-DGGSYTYYADNVKG (SEQ ID NO:31; HCDR2), EWGDYDGFDF (SEQ ID NO:15; HCDR3), [Clone 15D10]; or (b) the amino acid sequences RASQSISGYLS (SEQ ID NO:30; LCDR1), AASTLQS (SEQ ID NO:26; LCDR2), LQYDSTPYT (SEQ ID NO:23; LCDR3), GFTFSDYGMS (SEQ ID NO:13; HCDR1), VSTIS-DGGSYTYYADSVKG (SEQ ID NO:28; HCDR2), EWGDYDGFDE (SEQ ID NO:29; HCDR3), [Clone 17H10]; or (c) the amino acid sequences RASQSISSYLN (SEQ ID NO:50; LCDR1), AASSLDS (SEQ ID NO:22; LCDR2), LQYDSTPLT (SEQ ID NO:18; LCDR3), GFTFSDYGMS (SEQ ID NO:13; HCDR1), VSTIS-DGGSYTYYADSVKG (SEQ ID NO:28; HCDR2), EYGDYDGFDY (SEQ ID NO:51; HCDR3), [Clone 09D12]; or (d) the amino acid sequences RASQEISSYLS (SEQ ID NO:21; LCDR1), AASSLQS (SEQ ID NO:17; LCDR2), LQYDSTPLT (SEQ ID NO:18; LCDR3), GFTFSDYGMS (SEQ ID NO:13; HCDR1), VSTIS-DSGSYIYYADSVKG (SEQ ID NO:14; HCDR2), EWGDYDGFDH (SEQ ID NO:27; HCDR3), [Clone 15D03]; or
(e) the amino acid sequences RASQIISSYLS (SEQ ID NO:52; LCDR1), AASSLDS (SEQ ID NO:22; LCDR2), LQYYSTPLT (SEQ ID NO:53; LCDR3), GFTFSDYGMS (SEQ ID NO:13; HCDR1), VSTIS-DSGSYTYYADSVKG (SEQ ID NO:54; HCDR2), EWGDYDGFDN (SEQ ID NO:55; HCDR3), [Clone 11H02]; or
(f) the amino acid sequences RASQEISSYLS (SEQ ID NO:21; LCDR1), AASSLDS (SEQ ID NO:22; LCDR2), LQYDSTPYT (SEQ ID NO:23; LCDR3), GFTFSDYGMS (SEQ ID NO:13; HCDR1), VSTIS-DSGSYTYYPDSVKG (SEQ ID NO:19; HCDR2), ELGDYDGFDY (SEQ ID NO:20; HCDR3), [Clone 15G11]; or
(g) the amino acid sequences RASQSISSYLS (SEQ ID NO:16; LCDR1), AASSLQS (SEQ ID NO:17; LCDR2), LQYDSTPLT (SEQ ID NO:18; LCDR3), GFTFSDYGMS (SEQ ID NO:13; HCDR1), VSTIS-DSGTTIYYADNVKG (SEQ ID NO:56; HCDR2), EYGDYDGFDY (SEQ ID NO:51; HCDR3), [Clone 15E02]; or
(h) the amino acid sequences RASQSISSYLS (SEQ ID NO:16; LCDR1), AASSLQS (SEQ ID NO:17; LCDR2), LQYDSTPLT (SEQ ID NO:18; LCDR3), GFTFSDYSMS (SEQ ID NO:24; HCDR1), VSTIS-DGGSYTYYPDSVKG (SEQ ID NO:57; HCDR2), ELGDYDGFDY (SEQ ID NO:20; HCDR3), [Clone 09H02]; or
(i) the amino acid sequences RASQEISSYLS (SEQ ID NO:21; LCDR1), AASTLQS (SEQ ID NO:26; LCDR2), LQYDSTPLT (SEQ ID NO:18; LCDR3), GFTFSDYSMS (SEQ ID NO:24; HCDR1), VSTIS-DSGTYTYYPDSVKG (SEQ ID NO:25; HCDR2), EWGDYDGFDF (SEQ ID NO:15; HCDR3), [Clone 16B09]; or
(j) the amino acid sequences RASQSISSYLS (SEQ ID NO:16; LCDR1), AASSLQS (SEQ ID NO:17; LCDR2), LQYDSTPLT (SEQ ID NO:18; LCDR3), GFTFSDYGMS (SEQ ID NO:13; HCDR1), VSTIS-DSGSYIYYADSVKG (SEQ ID NO:14; HCDR2), ELGDYDGFDY (SEQ ID NO:20; HCDR3), [Clone MH1]; or
(k) the amino acid sequences RASQSISSYLS (SEQ ID NO:16; LCDR1), AASSLQS (SEQ ID NO:17; LCDR2), LQYDSTPLT (SEQ ID NO:18; LCDR3), GFTFSDYGMS (SEQ ID NO:13; HCDR1), VSTIS-DSGSYIYYADSVKG (SEQ ID NO:14; HCDR2), EWGDYDGFDF (SEQ ID NO:15; HCDR3), [Clone MH2]; or
(l) the amino acid sequences RASQSISSYLS (SEQ ID NO:16; LCDR1), AASSLQS (SEQ ID NO:17; LCDR2), LQYDSTPLT (SEQ ID NO:18; LCDR3), GFTFSDYSMS (SEQ ID NO:24; HCDR1), VSTIS-DSGSTIYYADSVKG (SEQ ID NO:58; HCDR2), EWGDYDGFDF (SEQ ID NO:15; HCDR3), [Clone MH3]; or
(m) the amino acid sequences RASQSISSYLS (SEQ ID NO:16; LCDR1), AASSLQS (SEQ ID NO:17; LCDR2), LQYDSTPLT (SEQ ID NO:18; LCDR3), GFTFSDYGMS (SEQ ID NO:13; HCDR1), VSTIS-DSGSYIYYADSVKG (SEQ ID NO:14; HCDR2), EWGDYDGFDE (SEQ ID NO:29; HCDR3), [Clone MH4]; or
(n) the amino acid sequences RASQSISSYLS (SEQ ID NO:16; LCDR1), AASSLQS (SEQ ID NO:17; LCDR2), LQYDSTPLT (SEQ ID NO:18; LCDR3), GFTFSDYGMS (SEQ ID NO:13; HCDR1), VSTIS-DSGSTIYYADSVKG (SEQ ID NO:58; HCDR2), EYGDYDGFDY (SEQ ID NO:51; HCDR3), [Clone MH5]; or
(o) the amino acid sequences RASQSISSYLN (SEQ ID NO:50; LCDR1), AASSLQS (SEQ ID NO:17; LCDR2), LQYDSTPLT (SEQ ID NO:18; LCDR3), GFTFSDYGMS (SEQ ID NO:13; HCDR1), VSTIS-DSGSTIYYADSVKG (SEQ ID NO:58; HCDR2), EYGDYDGFDY (SEQ ID NO:51; HCDR3), [Clone TTP]; or
(p) the amino acid sequences RASQEISTYLS (SEQ ID NO: 261; LCDR1), AASTLQS (SEQ ID NO:26; LCDR2), LQYDSSPLT (SEQ ID NO: 262; LCDR3), GFTFSDYSMS (SEQ ID NO: 24; HCDR1), VSTIS-DSGTYTYYPDSVKG (SEQ ID NO: 25; HCDR2), EWGDYDGFDF (SEQ ID NO: 15; HCDR3), [Clone 15G11-DI9]; or
(q) the amino acid sequences RASQEISSYLS (SEQ ID NO: 21; LCDR1), AASSLDT (SEQ ID NO: 263; LCDR2), LQYDSTPYT (SEQ ID NO: 23; LCDR3), GFTFSDYSMS (SEQ ID NO: 24; HCDR1), VSTIS-DSGTYTYYPDSVKG (SEQ ID NO: 25; HCDR2), EWGDYDGFDF (SEQ ID NO: 15; HCDR3), [Clone 15G11-DI5].

In some aspects, disclosed herein is an anti-ERBB3 antibody or an antigen-binding portion thereof, wherein the antibody comprises a heavy chain variable (VH) region and a light chain variable (VL) region, wherein
(a) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); and the VL region amino acid sequence comprises LCDR1 of RASQEISTYLS (SEQ ID NO: 261), LCDR2 of AASTLQS (SEQ ID NO:26) and LCDR3 of LQYDSSPLT (SEQ ID NO: 262);
(b) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); and the VL region amino acid sequence comprises LCDR1 of RASQEISSYLS (SEQ ID NO: 21), LCDR2 of AASSLDT (SEQ ID NO: 263) and LCDR3 of LQYDSTPYT (SEQ ID NO: 23);
(c) the VH region amino acid sequence comprises HCDR1 of GFTFSDYGMS (SEQ ID NO:13), HCDR2 of VSTISDSGSYTYYPDSVKG (SEQ ID NO:19) and HCDR3 of ELGDYDGFDY (SEQ ID NO:20); and the VL region amino acid sequence comprises LCDR1 of RASQEISSYLS (SEQ ID NO:21), LCDR2 of AASSLDS (SEQ ID NO:22) and LCDR3 of LQYDSTPYT (SEQ ID NO:23);
(d) the VH region amino acid sequence comprises HCDR1 of GFTFSDYSMS (SEQ ID NO:24), HCDR2 of VSTISDSGTYTYYPDSVKG (SEQ ID NO:25) and HCDR3 of EWGDYDGFDF (SEQ ID NO:15); and the VL region amino acid sequence comprises LCDR1 of RASQEISSYLS (SEQ ID NO:21), LCDR2 of AASTLQS (SEQ ID NO:26) and LCDR3 of LQYDSTPLT (SEQ ID NO:18);
(e) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDF (SEQ ID NO:15); and the VL region amino acid sequence comprises LCDR1 of RASQSISSYLS (SEQ ID NO:16), LCDR2 of AASSLQS (SEQ ID NO:17) and LCDR3 of LQYD-STPLT (SEQ ID NO:18);

(f) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDH (SEQ ID NO:27); and the VL region amino acid sequence comprises LCDR1 of RASQEISSYLS (SEQ ID NO:21), LCDR2 of AASSLQS (SEQ ID NO:17) and LCDR3 of LQYD-STPLT (SEQ ID NO:18);

(g) the VH region amino acid sequence comprises HCDR1 of GFTFSDYGMS (SEQ ID NO:13), HCDR2 of VSTISDGGSYTYYADSVKG (SEQ ID NO:28) and HCDR3 of EWGDYDGFDE (SEQ ID NO:29); and the VL region amino acid sequence comprises LCDR1 of RASQSISGYLS (SEQ ID NO:30), LCDR2 of AASTLQS (SEQ ID NO:26) and LCDR3 of LQYD-STPYT (SEQ ID NO:23);

(h) the VH region amino acid sequence comprises HCDR1 of GFTFSDYGMS (SEQ ID NO:13), HCDR2 of VSTISDGGSYTYYADNVKG (SEQ ID NO:31) and HCDR3 of EWGDYDGFDF (SEQ ID NO:15); and the VL region amino acid sequence comprises LCDR1 of RASQSISSYLS (SEQ ID NO:16), LCDR2 of AASTLQS (SEQ ID NO:26) and LCDR3 of LQYD-STPLT (SEQ ID NO:18); or (i) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDE (SEQ ID NO:29); and the VL region amino acid sequence comprises LCDR1 of RASQSISSYLS (SEQ ID NO:16), LCDR2 of AASSLQS (SEQ ID NO:17) and LCDR3 of LQYD-STPLT (SEQ ID NO:18).

In some aspects, disclosed herein is an anti-ERBB3 antibody or an antigen-binding portion thereof, wherein the antibody comprises a heavy chain variable (VH) region and a light chain variable (VL) region, wherein the VH region comprises any one of the VH region amino acid sequences in Table 7 or 8 and the VL region comprises any one of the VL region amino acid sequences in Table 6 or 8.

In some aspects, disclosed herein is an anti-ERBB3 antibody or an antigen-binding portion thereof, wherein the antibody comprises a heavy chain variable (VH) region and a light chain variable (VL) region, wherein (a) the VH region amino acid sequence comprises SEQ ID NO:236 and the VL region amino acid sequence comprises SEQ ID NO:225;

(b) the VH region amino acid sequence comprises SEQ ID NO:232 and the VL region amino acid sequence comprises SEQ ID NO:221;

(c) the VH region amino acid sequence comprises SEQ ID NO:253 and the VL region amino acid sequence comprises SEQ ID NO:254;

(d) the VH region amino acid sequence comprises SEQ ID NO:255 and the VL region amino acid sequence comprises SEQ ID NO:256;

(e) the VH region amino acid sequence comprises SEQ ID NO:228 and the VL region amino acid sequence comprises SEQ ID NO:217;

(f) the VH region amino acid sequence comprises SEQ ID NO:229 and the VL region amino acid sequence comprises SEQ ID NO:218;

(g) the VH region amino acid sequence comprises SEQ ID NO:230 and the VL region amino acid sequence comprises SEQ ID NO:219;

(h) the VH region amino acid sequence comprises SEQ ID NO:231 and the VL region amino acid sequence comprises SEQ ID NO:220;

(i) the VH region amino acid sequence comprises SEQ ID NO:233 and the VL region amino acid sequence comprises SEQ ID NO:222;

(j) the VH region amino acid sequence comprises SEQ ID NO:234 and the VL region amino acid sequence comprises SEQ ID NO:223;

(k) the VH region amino acid sequence comprises SEQ ID NO:235 and the VL region amino acid sequence comprises SEQ ID NO:224;

(l) the VH region amino acid sequence comprises SEQ ID NO:237 and the VL region amino acid sequence comprises SEQ ID NO:226; or (m) the VH region amino acid sequence comprises SEQ ID NO:238 and the VL region amino acid sequence comprises SEQ ID NO:227.

In some aspects, disclosed herein is an anti-ERBB3 antibody or an antigen-binding portion thereof, wherein the antibody comprises a heavy chain variable (VH) region and a light chain variable (VL) region, wherein (a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:236 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:225;

(b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:232 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:221;

(c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:253 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:254; or (d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:255 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:256.

In some aspects, the antibody or antigen-binding portion as defined herein may be isolated.

The antibody molecule or antigen-binding portion as defined herein may cross-compete for binding to ERBB3 with an antibody or antigen-binding portion thereof comprising the sets of CDRs disclosed herein. In some embodiments, the invention provides an isolated anti-ERBB3 antibody or an antigen-binding portion thereof, wherein the antibody or antigen-binding portion cross-competes for binding to ERBB3 with the antibody or antigen-binding portion comprising the sets of CDRs disclosed herein; and (a) comprises fully germline human framework amino acid sequences; and/or (b) does not comprise an isomerization site in the LCDR2; and/or (c) does not comprise a 'DG' isomerization site in the HCDR2; and/or (d) does not comprise an oxidation site at position 2 in the HCDR3; and/or and/or (e) exhibits a reduced number of predicted foreign human T cell receptor binding peptides in its v-domains in comparison to h24C05; and/or (f) contains no predicted foreign human T cell receptor binding peptides in its v-domains. In some embodiments, the anti-ERBB3 antibody or an antigen-binding portion thereof does not comprise an oxidation site at position 2 (e.g., W) in the HCDR3.

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-ERBB3 antibodies of the invention to the target ERBB3 (e.g., human ERBB3). The extent to which an antibody or portion thereof is able to interfere with the binding of another to the target, and therefore whether it can be said to cross-block or cross-compete according to the invention, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 6588-1321). Removal of such a site for example by substitution, deletion and/or insertion and then optionally testing (experimentally and/or theoretically) for (a) binding activity and/or (b) loss of the PTM is contemplated.

For example, the 24C05 murine LCDR2 (as defined herein, i.e. the amino acid sequence AASTLDS (SEQ ID NO:11)) has been identified to have a putative isomerisation site at residue 6. Removal this site at equivalent positions in an LCDR2 of the invention, for example by substitution of D (such as to Q), is envisaged (as for example in clone MH2 and others found in Tables 3 and 4).

In a further example, the 24C05 murine HCDR2 (as defined herein, i.e. the amino acid sequence VSTIS-DGGTYTYYPDNVKG (SEQ ID NO:5)) has been identified to have a putative isomerisation site at residue 6 (D). Reduction in chemical modification risk this site at equivalent positions in an HCDR2 of the invention, for example by substitution of G (such as to S, or D), is envisaged (as for example in clone 15G11 and others found in Tables 3 and 4).

In a further example, the 24C05 murine HCDR3 (as defined herein, i.e. the amino acid sequence EWGDYDGFDY (SEQ ID NO:6)) has been identified to have a putative oxidation site at residue 2 (W). Removal this site at equivalent positions in an LCDR1 of the invention, for example by substitution of W (such as to L or Y), is envisaged (as for example in clone 15G11 and others found in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region amino acid sequences.

The antibody molecule or antigen-binding portion thereof may comprise an IGHV3-11 human germline scaffold into which the corresponding HCDR sequences have been inserted. The antibody molecule or antigen-binding portion thereof may comprise a VH region that comprises an IGHV3-11 human germline scaffold amino acid sequence into which a set of corresponding HCDR1, HCDR2 and HCDR3 amino acid sequences have been inserted.

The antibody molecule or antigen-binding portion thereof may comprise an IGKV1-39 human germline scaffold into which the corresponding LCDR sequences have been inserted. The antibody molecule or antigen-binding portion thereof may comprise a VL region that comprises an IGKV1-39 human germline scaffold amino acid sequence into which a set of corresponding LCDR1, LCDR2 and LCDR3 amino acid sequences have been inserted.

The antibody molecule or antigen-binding portion thereof may comprise an IGHV3-11 human germline scaffold into which the corresponding HCDR sequences have been inserted and an IGKV1-39 human germline scaffold into which the corresponding LCDR sequences have been inserted. The antibody molecule or antigen-binding portion thereof may comprise a VH region that comprises an IGHV3-11 human germline scaffold amino acid sequence into which a set of corresponding HCDR1, HCDR2 and HCDR3 amino acid sequences have been inserted and a VL region that comprises an IGKV1-39 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4 (with all six CDR sequences being from the same clone).

In some aspects, the antibody molecule or antigen-binding portion thereof may comprise an immunoglobulin constant region. In some embodiments, the immunoglobulin constant region is IgG1, IgG2, IgG3, IgG4, IgA1 or IgA2. In additional embodiments, the immunoglobulin constant region is IgG1, IgG2, IgG3, IgG1null, IgG4(S228P), IgA1 or IgA2. The antibody molecule or antigen-binding portion thereof may comprise an immunologically inert constant region. In some aspects, an anti-ERBB3 antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-ERBB3 antibody or antigen-binding portion thereof may comprise an immunoglobulin constant region comprising a wild-type human IgG2 constant region or a wild-type human IgG4 constant region. In some aspects, an anti-ERBB3 antibody may comprise an immunoglobulin constant region comprising any one of the amino acid sequences in Table 9. The Fc region sequences in Table 9 begin at the CH1 domain. In some aspects, an anti-ERBB3 antibody may comprise an immunoglobulin constant region comprising an amino acid sequence of an Fc region of human IgG4, human IgG4(S228P), human IgG2, human IgG1, human IgG1-3M or human IgG1-4M. For example, the human IgG4(S228P) Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some aspects, a position of an amino acid residue in a constant region of an immunoglobulin molecule is numbered according to EU nomenclature (Ward et al., 1995 Therap. Immunol. 2:77-94). In some aspects, an immunoglobulin constant region may comprise an RDELT (SEQ ID NO:248) motif or an REEM (SEQ ID NO:249) motif (underlined in Table 9). The REEM (SEQ ID NO:249) allotype is found in a smaller human population than the RDELT (SEQ ID NO:248) allotype. In some aspects, an anti-ERBB3 antibody may comprise an immunoglobulin constant region comprising any one of SEQ ID NOS:239-245. In some aspects, an anti-ERBB3 antibody may comprise the six CDR amino acid sequences of any one of the clones in Table 4 and any one of the Fc region amino acid sequences in Table 9. In some aspects, an anti-ERBB3 antibody may comprise an immunoglobulin heavy chain constant region comprising any one of the Fc region amino acid sequences in Table 9 and an immunoglobulin light chain constant region that is a kappa light chain constant region or a lambda light chain constant region.

In some aspects, disclosed herein is an anti-ERBB3 antibody or an antigen-binding portion thereof, wherein the antibody comprises a heavy chain variable (VH) region, a light chain variable (VL) region and a heavy chain constant region, wherein
(a) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); the VL region amino acid sequence comprises LCDR1 of RASQEISTYLS (SEQ ID NO: 261), LCDR2 of AASTLQS (SEQ ID NO:26) and LCDR3 of LQYDSSPLT (SEQ ID NO: 262); and the heavy chain constant region comprises any one of SEQ ID NOS: 239-245;
(b) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); the VL region amino acid sequence comprises LCDR1 of RASQEISSYLS (SEQ ID NO: 21), LCDR2 of AASSLDT (SEQ ID NO: 263) and LCDR3 of LQYDSTPYT (SEQ ID NO: 23); and the heavy chain constant region comprises any one of SEQ ID NOS: 239-245;
(c) the VH region amino acid sequence comprises HCDR1 of GFTFSDYGMS (SEQ ID NO:13), HCDR2 of VSTISDSGSYTYYPDSVKG (SEQ ID NO:19) and HCDR3 of ELGDYDGFDY (SEQ ID NO:20); the VL region amino acid sequence comprises LCDR1 of RASQEISSYLS (SEQ ID NO:21), LCDR2 of AASSLDS (SEQ ID NO:22) and LCDR3 of LQYDSTPYT (SEQ ID NO:23); and the heavy chain constant region comprises any one of SEQ ID NOS: 239-245;
(d) the VH region amino acid sequence comprises HCDR1 of GFTFSDYSMS (SEQ ID NO:24), HCDR2 of VSTISDSGTYTYYPDSVKG (SEQ ID NO:25) and HCDR3 of EWGDYDGFDF (SEQ ID NO:15); the VL region amino acid sequence comprises LCDR1 of RASQEISSYLS (SEQ ID NO:21), LCDR2 of AASTLQS (SEQ ID NO:26) and LCDR3 of LQYDSTPLT (SEQ ID NO:18); and the heavy chain constant region comprises any one of SEQ ID NOS: 239-245;
(e) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDF (SEQ ID NO:15); the VL region amino acid sequence comprises LCDR1 of RASQSISSYLS (SEQ ID NO:16), LCDR2 of AASSLQS (SEQ ID NO:17) and LCDR3 of LQYDSTPLT (SEQ ID NO:18); and the heavy chain constant region comprises any one of SEQ ID NOS: 239-245;
(f) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDH (SEQ ID NO:27); the VL region amino acid sequence comprises LCDR1 of RASQEISSYLS (SEQ ID NO:21), LCDR2 of AASSLQS (SEQ ID NO:17) and LCDR3 of LQYDSTPLT (SEQ ID NO:18); and the heavy chain constant region comprises any one of SEQ ID NOS: 239-245;
(g) the VH region amino acid sequence comprises HCDR1 of GFTFSDYGMS (SEQ ID NO:13), HCDR2 of VSTISDGGSYTYYADSVKG (SEQ ID NO:28) and HCDR3 of EWGDYDGFDE (SEQ ID NO:29); the VL region amino acid sequence comprises LCDR1 of RASQSISGYLS (SEQ ID NO:30), LCDR2 of AASTLQS (SEQ ID NO:26) and LCDR3 of LQYDSTPYT (SEQ ID NO:23); and the heavy chain constant region comprises any one of SEQ ID NOS: 239-245;
(h) the VH region amino acid sequence comprises HCDR1 of GFTFSDYGMS (SEQ ID NO:13), HCDR2 of VSTISDGGSYTYYADNVKG (SEQ ID NO:31) and HCDR3 of EWGDYDGFDF (SEQ ID NO:15); the VL region amino acid sequence comprises LCDR1 of RASQSISSYLS (SEQ ID NO:16), LCDR2 of AASTLQS (SEQ ID NO:26) and LCDR3 of LQYD- STPLT (SEQ ID NO:18); and the heavy chain constant region comprises any one of SEQ ID NOS: 239-245; or (i) the VH region amino acid sequence comprises HCDR1 of GFTFSDYGMS (SEQ ID NO:13), HCDR2 of VSTISDSGSYIYYADSVKG (SEQ ID NO:14) and HCDR3 of EWGDYDGFDE (SEQ ID NO:29); the VL region amino acid sequence comprises LCDR1 of RASQSISSYLS (SEQ ID NO:16), LCDR2 of AASSLQS (SEQ ID NO:17) and LCDR3 of LQYD-STPLT (SEQ ID NO:18); and the heavy chain constant region comprises any one of SEQ ID NOS: 239-245.

In some aspects, disclosed herein is an anti-ERBB3 antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:236; the VL region amino acid sequence comprises or consists of SEQ ID NO:225; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(b) the VH region amino acid sequence comprises or consists of SEQ ID NO:232; the VL region amino acid sequence comprises or consists of SEQ ID NO:221; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(c) the VH region amino acid sequence comprises or consists of SEQ ID NO:253; the VL region amino acid sequence comprises or consists of SEQ ID NO:254; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A; or (d) the VH region amino acid sequence comprises or consists of SEQ ID NO:255; the VL region amino acid sequence comprises or consists of SEQ ID NO:256; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A.

In some aspects, disclosed herein is an anti-ERBB3 antibody or an antigen-binding portion thereof, wherein the antibody comprises a heavy chain variable (VH) region, a light chain variable (VL) region and a heavy chain constant region, wherein (a) the VH region amino acid sequence comprises or consists of SEQ ID NO:236; the VL region amino acid sequence comprises or consists of SEQ ID NO:225; and the heavy chain constant region comprises any one of SEQ ID NOS: 239-245;

(b) the VH region amino acid sequence comprises or consists of SEQ ID NO:232; the VL region amino acid sequence comprises or consists of SEQ ID NO:221; and the heavy chain constant region comprises any one of SEQ ID NOS: 239-245;

(c) the VH region amino acid sequence comprises or consists of SEQ ID NO:253; the VL region amino acid sequence comprises or consists of SEQ ID NO:254; and the heavy chain constant region comprises any one of SEQ ID NOS: 239-245; or (d) the VH region amino acid sequence comprises or consists of SEQ ID NO:255; the VL region amino acid sequence comprises or consists of SEQ ID NO:256; and the heavy chain constant region comprises any one of SEQ ID NOS: 239-245.

In some aspects, an anti-ERBB3 antibody may be immune effector null. In some aspects, an anti-ERBB3 antibody or an antigen-binding portion thereof does not induce immune effector function and, optionally, suppresses immune effector function. In some aspects, an anti-ERBB3 antibody may lack measurable binding to human FcγRI, FcγRIIa, FcγRIIIa and FcγRIIIb receptors but maintain binding to human FcγRIIb receptor and optionally maintain binding to human FcRn receptor. FcγRI, FcγRIIa, FcγRIIIa and FcγRIIIb are examples of activating receptors. FcγRIIb is an example of an inhibitory receptor. FcRn is an example of a recycling receptor. In some aspects, binding affinity of an anti-ERBB3 antibody or an antigen-binding portion thereof for human Fc receptors may be measured by BIA-CORE® analysis. In some aspects, Homogeneous Time Resolved Fluorescence (HTRF) can be used to study binding of an anti-ERBB3 antibody to human Fc receptors. In one example of HTRF, human IgG1 (wild type) is labelled, as is the full suite of Fc gamma receptors and then antibodies with engineered Fc fragments are used in titration competition. In some aspects, ERBB3-positive cells may be mixed with human white blood cells and anti-ERBB3 antibodies, and cell killing by CDC, ADCC and/or ADCP may be measured. In some aspects, an anti-ERBB3 antibody comprising an amino acid sequence of an Fc region of human IgG1-3M (see Table 9) is effector null. In some aspects, an anti-ERBB3 antibody comprising an amino acid sequence of an Fc region of human IgG1-3M (see Table 9) is not effector null.

The antibody molecule or antigen-binding portion thereof may be a Fab fragment, a F(ab)$_2$ fragment, an Fv fragment, a tetrameric antibody, a tetravalent antibody, a multispecific antibody (for example, a bispecific antibody), a domain-specific antibody, a single domain antibody, a monoclonal antibody or a fusion protein. In one embodiment, an antibody may be a bispecific antibody that binds specifically to a first antigen and a second antigen, wherein the first antigen is ERBB3 and the second antigen is not ERBB3. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked to a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the anti-folates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, downregulate self-antigen expression, or mask MHC antigens.

Also provided is a nucleic acid molecule encoding the antibody molecule or antigen-binding portion thereof of the invention as defined herein. A nucleic acid molecule may encode (a) the VH region amino acid sequence; (b) the VL region amino acid sequence; or (c) both the VH and the VL region amino acid sequences of an anti-ERBB3 antibody or an antigen-binding portion thereof described herein. In some aspects, the nucleic acid molecule as defined herein may be isolated.

Further provided is a vector comprising the nucleic acid molecule of the invention as defined herein. The vector may be an expression vector.

Also provided is a host cell comprising the nucleic acid molecule or the vector of the invention as defined herein. The host cell may be a recombinant host cell.

In a further aspect there is provided a method of producing an anti-ERBB3 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

The invention also provides a method for inhibiting ERBB3 signalling in a cell, the method comprising contacting the cell with an anti-ERBB3 antibody molecule or antigen-binding portion thereof described herein. In some embodiments, an anti-ERBB3 antibody molecule or antigen-binding portion of the invention locks ERBB3 into a monomeric form.

Further provided is a method for enhancing an immune response in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein. In some embodiments, an anti-ERBB3 antibody molecule or antigen-binding portion of the invention engages a subject's immune cells via antibody effector-function mediated engagement.

In a further aspect there is provided a method for treating or preventing cancer in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

For example, the cancer may be Gastrointestinal Stromal cancer (GIST), pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an autoimmune disease or an inflammatory disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

For example the autoimmune disease or inflammatory disease may be arthritis, asthma, multiple sclerosis, psoriasis, Crohn's disease, inflammatory bowel disease, lupus, Grave's disease and Hashimoto's thyroiditis, or ankylosing spondylitis.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an autoimmune disease or an inflammatory disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an autoimmune disease or an inflammatory disease.

The invention also provides a method for treating or preventing a cardiovascular disease or a fibrotic disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of a cardiovascular disease or a fibrotic disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of a cardiovascular disease or a fibrotic disease.

The cardiovascular disease in any aspect of the invention may for example be coronary heart disease or atherosclerosis.

For example, the fibrotic disease in any aspect of the invention may be myocardial infarction, angina, osteoarthritis, pulmonary fibrosis, asthma, cystic fibrosis or bronchitis.

In one embodiment, the invention provides an anti-ERBB3 antibody or an antigen-binding portion thereof comprising the amino acid sequences disclosed herein for use in therapy.

The pharmaceutical composition of the invention may comprise a pharmaceutically acceptable excipient, carrier or diluent. A pharmaceutically acceptable excipient may be a compound ora combination of compounds entering into a pharmaceutical composition which does not provoke secondary reactions and which allows, for example, facilitation of the administration of the anti-ERBB3 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-ERBB3 antibody molecule.

In some embodiments, the anti-ERBB3 antibody molecule may be provided in a lyophilised form for reconstitution prior to administration. For example, lyophilised antibody molecules may be re-constituted in sterile water and mixed with saline prior to administration to an individual.

The anti-ERBB3 antibody molecules will usually be administered in the form of a pharmaceutical composition, which may comprise at least one component in addition to the antibody molecule. Thus pharmaceutical compositions may comprise, in addition to the anti-ERBB3 antibody molecule, a pharmaceutically acceptable excipient, carrier, buffer, stabilizer or other materials well known to those skilled in the art. Such materials should be non-toxic and should not interfere with the efficacy of the anti-ERBB3 antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-ERBB3 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-ERBB3 antibody molecule may be administered alone or in combination with other treatments, either simultaneously or sequentially dependent upon the condition to be treated.

An anti-ERBB3 antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-ERBB3 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1, IgG1null or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-ERBB3 antibody molecules as described herein may be administered as sub-cutaneous injections. Sub-cutaneous injections may be administered using an auto-injector, for example for long or short-term prophylaxis/treatment.

In some embodiments, the therapeutic effect of the anti-ERBB3 antibody molecule may persist for several multiples of the antibody half-life in serum, depending on the dose. For example, the therapeutic effect of a single dose of the anti-ERBB3 antibody molecule may persist in an individual for 1 month or more, 2 months or more, 3 months or more, 4 months or more, 5 months or more, or 6 months or more.

The invention also provides a method of producing an antibody molecule which specifically binds to human ERBB3 and optionally also to rhesus monkey ERBB3 or an antigen-binding portion thereof, comprising the steps of:

(1) grafting anti-ERBB3 CDRs from a non-human source into a human v-domain framework to produce a humanized anti-ERBB3 antibody molecule or antigen-binding portion thereof;

(2) generating a phage library of clones of the humanized anti-ERBB3 antibody molecule or antigen-binding portion thereof comprising one or more mutations in the CDRs;

(3) selecting the phage library for binding to human ERBB3 and optionally also to rhesus monkey ERBB3;

(4) screening clones from the selection step (3) having binding specificity to human ERBB3 and optionally also to rhesus monkey ERBB3; and (5) producing an antibody molecule which specifically binds to human ERBB3 and optionally also to rhesus monkey ERBB3, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "ERBB3" refers to the ERBB3 protein and variants thereof that retain at least part of the biological activity of ERBB3. As used herein, ERBB3 includes all mammalian species of native sequence ERBB3, including human, rat, mouse and chicken. The term "ERBB3" is used to include variants, isoforms and species homologs of human ERBB3. Antibodies of the invention may cross-react with ERBB3 from species other than human, in particular ERBB3 from rhesus monkey (*Macaca mulatta*). Examples of human and rhesus ERBB3 amino acid sequences are provided in Table 10. In certain embodiments, the antibodies may be completely specific for human ERBB3 and may not exhibit non-human cross-reactivity.

As used herein, an "antagonist" as used in the context of the antibody of the invention or an "anti-ERBB3 antagonist antibody" (interchangeably termed "anti-ERBB3 antibody") refers to an antibody which is able to bind to ERBB3 and inhibit ERBB3 biological activity and/or downstream pathway(s) mediated by ERBB3 signalling. An anti-ERBB3 antagonist antibody encompasses antibodies that can block, antagonize, suppress or reduce (including significantly) ERBB3 biological activity, including downstream pathways mediated by ERBB3 signalling, such as receptor binding and/or elicitation of a cellular response to ERBB3. For the purposes of the present invention, it will be explicitly understood that the term "anti-ERBB3 antagonist antibody" encompass all the terms, titles, and functional states and characteristics whereby ERBB3 itself, and ERBB3 biological activity, or the consequences of the activity or biological activity, are substantially nullified, decreased, or neutralized in any meaningful degree.

The antibody "specifically binds" "specifically interacts", "preferentially binds", "binds" or "interacts" with ERBB3 if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to ERBB3. Antigen binding functions of an antibody molecule can be performed by fragments of an intact antibody. Examples of binding fragments encompassed within the term "antigen binding portion" of an antibody molecule include Fab; Fab'; F(ab')$_2$; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, and contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 Aug. 2016]). The CDR definition used herein (a "Unified" definition) incorporates the lessons of all such prior insights and includes all appropriate loop positions required to sample the full residue landscape that potentially mediates target-binding complementarity.

Table 1 shows the amino acid sequences of the 24C05 murine anti-ERBB3 antibody CDRs as defined herein (a "Unified" scheme), in comparison to well-known alternative systems for defining the same CDRs.

As used herein the term "conservative substitution" refers to replacement of an amino acid with another amino acid which does not significantly deleteriously change the functional activity. A preferred example of a "conservative substitution" is the replacement of one amino acid with another amino acid which has a value≥0 in the following BLOSUM 62 substitution matrix (see Henikoff & Henikoff, 1992, PNAS 89: 10915-10919):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4 |

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')$_2$ or other antigen-binding sub-sequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to ERBB3, which is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 μM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen ERBB3 to inhibit 50% of activity measured in a ERBB3 activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to ERBB3.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neo-adjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-ERBB3 Therapeutic Antibodies Introduction In this example, we successfully generated a panel of antagonistic, optimized anti-ERBB3 antibodies. These anti-ERBB3 antibodies are well expressed, biophysically stable, highly soluble and of maximized amino acid sequence identity to preferred human germlines.

Materials and Methods
ERBB3 Library Generation and Selection
The ERBB3 Fab mutagenesis repertoire was assembled by mass oligo synthesis and PCR.

This library was designed to sample the germline human CDR residue or murine CDR residue at all positions where the sequences differed, but also sampled all amino acids other than cysteine at key selected CDR positions e.g. in HCDR1 and HCDR3. The amplified Fab repertoire was then cloned via restriction-ligation into a phagemid vector, transformed into E. coli TG-1 cells, and the phage repertoire rescued essentially as previously described in detail (Finlay et al., 2011, Methods Mol Biol 681: 383-401).

Phage selections were performed by coating streptavidin magnetic microbeads with biotinylated ERBB3 target protein (either human or rhesus), washing the beads thrice with PBS and resuspending in PBS pH7.4 plus 5% skim milk protein. These beads were coated at 100 nM target protein in round 1 of selection, followed by reduced antigen concentrations in three successive rounds. In each round, phage were eluted using trypsin before re-infection into TG1 cells.

Periplasmic Extracts Production (Small-Scale)
Production of soluble Fabs in individual E. coli clones was performed. E. coli TG1 cells in logarhythmic growth phase were induced with isopropyl 1-thio-β-D-galactopyranoside. Periplasmic extracts containing soluble Fab were generated by a freeze/thaw cycle: Bacterial cell pellets were frozen at −20° C. for overnight and then thawed at room temperature and resuspended in PBS pH 7.4. The supernatants containing the soluble Fab were collected after shaking at room temperature and centrifugation.

IgG Expression and Purification
Mammalian codon-optimized synthetic genes encoding the heavy and light chain variable domains of the lead panel anti-ERBB3 antibodies plus the m24C05 and h24C05 were cloned into mammalian expression vectors comprising IgG1null ('IgG1null'; human IgG1 containing L234A, L235A, G237A mutations in the lower hinge that abrogate normal immunoglobulin Fc effector functions) or IgG1 and human Cκ domains, respectively. Co-transfection of heavy and light chain containing vector in mammalian expression system was performed, followed by protein A-based purification of the IgG, quantification and QC on denaturing and non-denaturing SDS-PAGE.

Direct Binding ELISA for Fab and IgG
Binding and cross-reactivity of the lead panel to the recombinant proteins was initially assessed by binding ELISA. The human ERBB3 human Fc tagged recombinant protein and the rhesus monkey ERBB3 human Fc tagged recombinant protein were coated to the surface of MaxiSorp™ flat-bottom 96 well plate at 1 µg/ml. The purified IgG samples were titrated in two fold serial dilutions starting from 500 nM to 0.008 nM and allowed to bind to the coated antigens. The Fabs were detected using mouse anti-c-myc antibody followed by donkey anti-mouse IgG conjugated to horseradish peroxidase. The IgGs were detected using the mouse anti-human IgG conjugated to horseradish peroxidase. Binding signals were visualized with 3,3',5,5'-Tetramethylbenzidine Substrate Solution (TMB) and the absorbance measured at 450 nm.

Alphascreen Epitope Competition Assay for IgG1Nullnull Antibodies
The AlphaScreen assay (Perkin Elmer) was performed in a 25 µl final volume in 384-well white microtiter plates (Greiner). The reaction buffer contained 1×PBS pH 7.3 (Oxoid, Cat. nr. BR0014G) and 0.05% (v/v) Tween® 20 (Sigma, Cat. nr. P9416). Purified IgG samples were titrated in three fold serial dilutions starting at 100 nM final concentration and incubated with biotinylated human ERBB3-His (Acrobiosystems) at 1 nM final concentration for 20 minutes at room temperature. The parental IgG and the anti-human IgG1 Acceptor beads at were added and the mix was incubated for 1 hour at room temperature. Followed by addition of the Streptavidin Donor beads and incubation for 30 minutes at room temperature. The emission of light was measured in the EnVision multilabel plate reader (Perkin Elmer) and analysed using the EnVision manager software. Values were reported as Counts Per Second (CPS) and corrected for crosstalk.

Biacore® Analyses of IgG Affinity for Monomeric Human and Rhesus ERBB3 in Solution
Affinity (KD) of purified IgGs was determined via SPR with antigen in-solution on a Biacore® 3000 (GE). A mouse anti-human antibody (CH1 specific) was immobilized on a CM5 Sensor Chip to a level of 2000 RU in acetate buffer at pH 4.5 using amine coupling following the Wizard instructions for two channels. One channel was used for background signal correction. The standard running buffer HBS-EP pH 7.4 was used. Regeneration was performed with a single injection of 10 µl of 10 mM Glycine at pH 1.5 at 20 µl/minute. IgG samples were injected for 2 minutes at 50 nM at 30 µl/min followed by an off-rate of 60 seconds. The monomeric antigen (human ERBB3 His tagged or rhesus monkey ERBB3 His tag) was injected in two fold serial dilutions from 3 nM down to 0.2 nM, for 2 minutes at 30 µl/min followed by an off-rate of 300 seconds. The obtained sensorgrams were analysed using the Biacore® 3000 evaluation (BIAevaluation) software. The KD was calculated by simultaneous fitting of the association and dissociation phases to a 1:1 Langmuir binding model.

Flow Cytometry of IgGs

Purified IgGs were tested in FACs for binding to human and rhesus monkey ERBB3 expressed on transiently transfected HEK-293 cells and HEK-293 wild-type cells. The IgG samples were titrated in three-fold serial dilutions starting at 500 nM to 0.008 nM. Binding of IgGs was detected with a mouse anti-human IgG conjugated to FITC. Results were analyzed by examining the Mean Fluorescence Intensity (MFI) of 10000 cells per sample in the BL-1 channel detector of a flow cytometer (Attune™ NxT Acoustic Focusing Cytometer, Invitrogen/ThermoFisher Scientific). The EC50 values were calculated using the MFI values in GraphPad Prism software (Graph Pad Software, La Jolla, Calif.) and 4 parameters.

Antibody v-Domain T Cell Epitope Content: in Silico Analyses

In silico technologies (Abzena, Ltd.), which are based on identifying the location of T cell epitopes in therapeutic antibodies and proteins, were used for assessing potential immunogenicity in antibody v-domains. iTope™ was used to analyse the VL and a VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

In addition, the sequences were analysed using TCED™ (T Cell Epitope Database™) search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

Results and Discussion

CDR Grafting onto Preferred Human Germline v-Genes

The CDRs of an antagonistic murine anti-ERBB3 IgG 24C05 (24C05; see WO2011136911A2 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV3-11 and IGKV1-39, which are known to have good solubility, high physical stability and are used at high frequency in the expressed human antibody repertoire.

Those scaffolds and grafted CDR definitions are outlined in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGHV3-11/IGKV1-39 graft was therefore taken forward as the template for CDR mutagenesis and selection of improved clones.

Library Generation and Screening

The CDR-grafted IGKV1-39/IGHV3-11 v-domain sequences were combined into a Fab phage display format and a mutagenesis library cassette was generated by oligo synthesis and assembly. The final Fab library was ligated into a phage display vector and transformed into E. coli via electroporation to generate $1.2 \times 10^9$ independent clones. Library build quality was verified by sequencing 96 clones, across both v-domains. This sequencing data showed that the positions encoding either the murine or human germline residue at each position of variance had been effectively sampled at a frequency of approximately 50% and that positions intended to encode all amino acids exhibited full coverage. Libraries were rescued using helper phage M13 and selections performed on biotinylated human and rhesus monkey ERBB3-Fc proteins in multiple separate branches.

Post-selection screening and DNA sequencing revealed the presence of 658 human and rhesus ERBB3-binding Fab clones that exhibited strong binding to human and rhesus ERBB3 in ELISA (FIG. 1A) and >50% inhibition of 24C05 IgG1null binding to human ERBB3 in Alphascreen assay (FIG. 1B). Amongst these 658 clones, the framework sequences remained fully germline while humanizing mutations were also observed in all CDRs (Table 3). Lead clones were ranked based on level of CDR germlining versus ELISA and Alphascreen signals for binding to both human and rhesus ERBB3-Fc. The v-domains of the 9 top clones from this ranking were then sub-cloned into IgG expression vectors for further testing as below (Table 4).

While germ-lining mutations were observed in all CDRs for the lead clones derived directly from library selections, it remained possible that sequence analyses might allow further clones to be designed to have maximal humanization. The 658 sequence-unique hits with binding signals against human and rhesus protein were therefore used to analyse the retention frequency for murine amino acids in the CDRs of this functionally characterized population. Positional amino acid retention frequency was expressed as a percentage found in the $V_L$ and $V_H$ domains (FIGS. 2A&B, respectively). Murine residues with RF <75% were regarded as positions that are possibly not essential to the target-binding paratope and are likely to be open to germ-lining, in a series of combinatorial designs (Table 4). In a surprising finding for such a high-affinity starting clone, only a minority of murine residues were found to be highly positively selected. Indeed, only 3 of the 9 murine residues in the HCDR1 and HCDR2 exhibited retention frequency above 75% (FIG. 2A). This analysis strongly suggested that the VH sequence outside the HCDR3 could possibly be rendered very close in germline identity to IGHV3-11. In the $V_L$ domain, only 4 of 10 murine CDR residues derived from the h24C05 sequence were retained with frequencies >75% (FIG. 3A).

Designs containing combinations of those murine residues with RF>75% with those also heavily-selected in the lead clone population were given the prefix "MH" (MH=Maximally Humanized). In total 5 MH clones were generated. In addition, a 'TTP' (TTP=Total Theoretically Possible) clone was generated which combined the 6 most humanized CDR sequences found in the high-functioning, epitope-competing Fab screen. The MH, TTP and library-derived clone v-domains (Table 4) were generated by gene synthesis and (along with the control antibodies), cloned into human expression vectors for production in IgG1null format. All IgGs were readily expressed and purified from transient transfections of mammalian cells.

Lead IgG Specificity and Potency Characteristics

The purified IgGs described above were then tested for binding to human and rhesus ERBB3 in direct titration ELISA format (FIGS. 3A&B). This analysis demonstrated that the majority of library derived and designer (MH) clones retained binding activity for human and/or rhesus ERBB3 that was equivalent to, or improved over, the h24C05 IgG1null.

An Alphascreen assay was established to allow the testing of IgGs for epitope competition with h24C05 IgG binding to biotinylated monomeric human ERBB3. In this assay, the top-performing library-derived and designer IgGs were more effectively differentiated. While all clones exhibited full, concentration-dependent neutralisation, and the majority of clones exhibited equivalent or improved competition for the h24C05 epitope over h24C05 (FIG. 4), some exhibited less potent epitope competition including MH1.

Biacore® analyses of binding affinity were performed for all IgGs to solution-phase, monomeric human and rhesus ERBB3 proteins. In all cases, accurate 1:1 binding affinities with low $Chi^2$ values were obtained (Table 5). These analyses showed that library-derived clones which consistently gave the highest EC50 and IC50 values in Fab and IgG ELISA and Alphascreen assays also showed highest affinity binding to human and rhesus ERBB3 (Table 5). Importantly, these improvements in affinity were recapitulated in rhesus binding, with the majority of these clones exhibiting affinities within 3-fold of the human ERBB3 affinity. Affinity differentials of less than 4-fold between human and rhesus target orthologs are highly beneficial in pre-clinical drug development analyses as they allow significantly better design and interpretation of e.g. monkey safety, PK and PD modelling experiments.

In addition, comparison of the affinities of MH and TTP clones confirmed the influence of the LCDR1 in maintaining binding affinity, as mutations of the residues 'S>N' at positions 11 in that CDR resulted in approximately 2-fold loss of KD for clones TTP in comparison to clone MH5, against human ERBB3 (Table 5). Comparison of clones MH2 and MH3 also confirmed that the mutation of HCDR1 residue 8 (A to S) and HCDR2 residue 10 (Y to T) in MH3 also led to an approximately 3-fold reduction in binding affinity for human and rhesus ERBB3 in comparison to clone MH2 (Table 5).

The findings outlined above confirmed that the multiple clones could retain high binding affinity (in the pM range), epitope specificity and species cross-reactivity of h24C05, while retaining only minimal non-germline amino acid content in the VH and VL domains (excluding the HCDR3, for which there is no corresponding germline). This near-complete germlining of the VH domain significantly reduced immunogenic potential in man. In addition, the gemlining mutations observed in multiple clones led to the removal or improvement of several amino acid degradation motifs found in the murine CDRs of h24C05 that are a known risk for manufacturing and clinical development qualities in antibody molecules: A putative isomerization risk at LCDR2 position 6 (D) was removed via mutation to Q, a 'DG' aspartic acid isomerisation motif in HCDR2 position 6 and 7 was converted to the lower-risk motif 'DS', and a putative oxidation risk at HCDR3 position 2 (W) was removed by mutation to Y or L. These improvements in primary sequence were not possible to predict a priori and are of direct consequence in both manufacturing and clinical development of an antibody therapeutic as they are all potential stability risk motifs, leading to intrinsic product heterogeneity. Such risk motifs can lead to costly development issues where multiple process modifications must be made to maximise intact antibody yield and to minimise product heterogeneity. Degradation motifs are also a clinical development risk, as accelerated antibody breakdown in the body can reduce both half-life and potency of the molecule.

Flow Cytometric Analyses of Lead IgG Binding Specificity at the Cell Membrane

Antibodies to ERBB3 were analysed for concentration-dependent binding at the cell surface via flow cytometry. HEK-293 cells were transiently transfected with either human or rhesus ERBB3 full-length cDNAs. Anti-ERBB3 IgGs and an isotype control were then all tested in IgG1null format, over a concentration range of 500-0.008 nM for binding to human (FIG. 5A) and rhesus (FIG. 5B) transfected cells. All IgGs other than the isotype control showed strong concentration-dependent binding to human and rhesus ERBB3+ cells, with a maximum MFI in each case being >20-fold higher than observed background signals for IgG1 isotype control.

Antibody v-domain T Cell Epitope Analyses

In silico technologies (Abzena, Ltd.), which are based on identifying the location of T cell epitopes in therapeutic antibodies and proteins, were used for assessing the immunogenicity of both the h24C05 and lead antibody 15G11 v-domains. Analysis of the v-domain sequences was performed with overlapping 9mer peptides (with each overlapping the last peptide by 8 residues) which were tested against each of the 34 MHC class II allotypes. Each 9mer was scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score >0.6), such peptides were defined as 'high affinity' MHC class II binding peptides which are considered a high risk for containing CD4+ T cell epitopes. Low affinity MHC class II binding peptides bind a high number of alleles (>50%) with a binding score >0.55 (but without a majority >0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+ (previously identified epitope in TCED database), and Germline Epitope ('GE'—human germline peptide sequence with high MHC Class II binding affinity). Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

This analysis showed that despite the replacement with several murine residues with human germline equivalents in the CDRs of the key lead 15G11, the method of Townsend et al. had not led to significant beneficial changes in peptide epitope content in comparison to h24C05 (FIG. 6A, FIG. 6B). On the contrary, while 15G11 had improved GE content (11) over h24C05 (10), 15G11 had unexpectedly increased immunogenicity risk rather than decreased, as it contained not only 2 new LAF epitopes, but had also gained a high-risk TCED+ LAF in the HCDR-1. As the v-domain framework regions (i.e. outside the CDR sequences) of both antibodies were germline in sequence (Table 2), all changes in predicted immunogenicity in 15G11 came about as a result of the germlining of CDR residues.

As the method of Townsend et al. had failed to improve either the potency or immunogenicity risk of lead clone 15G11 over h24C05, the potential of further non-human germline mutagenesis in the CDRs was examined. Selection of specific amino acid changes was influenced by the available biophysical and biochemical data, e.g. constraints on modification of the parental 15G11 sequence taking into consideration secondary and tertiary protein structures as well as potential interactions of amino acid side chains with the core of the protein. Additionally, selection of amino acid changes was influenced by the frequency of occurrence of any particular amino acid at any given position in the human repertoire. The aim was therefore to avoid introducing amino acids that never occur at a given position and that would be more likely to adversely affect the structure. The amino acid cysteine was not considered at any point to avoid introducing an unpaired cysteine residue, which could potentially lead to aggregation issues. Each epitope was analysed individually to identify residues that would remove or reduce promiscuous MHC class II binding and, subsequently, the proposed epitope variants were analysed in the context of the whole 15G11 sequence to ensure that novel potential epitopes were not introduced in adjacent regions. Increased value was placed on the use of mutations that had been observed to be tolerated in the functionally-selected population of CDR sequences (Table 3). This process was applied to four key predicted epitopes.

Epitope 1 was the highest risk (TCED+) epitope identified and partially overlaps with VH CDR1 (FIG. 7A). As such, performing any substitutions within this region could potentially impact on binding to antigen. By iTope™ analysis, this region consists of one T cell epitope with a p1 anchor at Y32 (Kabat numbering). Only a limited number of changes were assessed for Framework 2 as this region is highly conserved between antibodies, with several residues playing a role in forming the VH:VL interface. In contrast to Framework regions, CDRs show greater sequence diversity, although this diversity is substantially less pronounced for VH CDR1 and 2 compared with VH CDR3. Within the VH CDR1 region, it was observed that for a number of given positions, several amino acid substitutions were able to completely abrogate potential T cell epitope binding. However, in many cases, these amino acids are almost never observed in that given position, and so these amino acids were discarded. Suggested sequence changes are illustrated in FIG. 7A. Two epitope-ablating variants were prioritised in this peptide: YSMSWIRQA (SED ID NO:250) and YGMSWVRQA (SEQ ID NO:251) (mutation underlined in both cases). The first mutation G>S could potentially ablate the TCED+ epitope, whereas the second mutation I>V could potentially render the peptide sequence a GE.

Epitope 2 lies primarily within VL CDR1 and, as such, performing any substitutions within this region could potentially impact on binding to antigen. By iTope™ analysis, this region consists of one potential T cell epitope with a p1 anchor at 129. Changes were kept to a minimum in Framework 2 as this region is very highly conserved between antibodies, with several residues playing a role in forming the VH:VL interface. In contrast to Framework regions, CDRs show greater sequence diversity, although this diversity is substantially less pronounced for VLs compared with VHs and for VL CDR1 and 2 compared with VL CDR3. Within the VL CDR1 region, it was observed that for a number of given positions, several amino acid substitutions were able to completely abrogate potential T cell epitope binding. However, in many cases, these amino acids are almost never observed in that given position, and so these amino acids were discarded. Suggested sequence changes are illustrated in FIG. 7B.

Epitope 3 overlaps partially with VL CDR2 and, as such, performing any mutations within this region could potentially impact on binding to antigen. By iTope™ analysis, this region consists of one potential T cell epitope with a p1 anchor at 148. Changes to Framework 2 were kept to a minimum as this region is highly conserved between antibodies. In contrast to Framework regions, CDRs show greater sequence diversity, although this diversity is less pronounced for VL CDRs compared with VH CDRs. From iTope™ analysis, it was observed that the majority of amino acid substitutions at almost all positions within the core 9-mer were detrimental, with increased binding observed for almost all substitutions. A limited number of amino acid substitutions were identified that abrogate potential T cell epitope binding, however, these amino acids are almost never observed in that given position, and so these amino acids were discarded. Suggested sequence changes are illustrated in FIG. 7C. Importantly, in the analysis, as so many changes in this region were potentially detrimental, selected full CDR variants in the LCDR-2 (Tables 3 and 4) were examined for their TCR epitope risk. Surprisingly, the LCDR-2 sequence AASTLQS (SEQ ID NO:26) was found to fully ablate the HAF peptide risk of this epitope, and a similar high-risk HAF epitope in h24C05 (IYAASTLDS (SEQ ID NO:252)). As a result, this CDR sequence was prioritised for inclusion in a subset of new variants.

Epitope 4 lies completely within VL CDR3 and, as such, performing any substitutions within this region could potentially impact on binding to antigen. By iTope™ analysis, this region consists of one potential T cell epitope with a p1 anchor at L89. No Framework changes were considered. In contrast to Framework regions, CDRs show greater sequence diversity, especially for CDR3, and so amino acid substitutions were not discarded in this region on the basis of occurrence. Several single amino acid substitutions were observed to partially abrogate the binding of both potential T cell epitopes. Suggested single amino acid substitution changes that have an effect on Epitope 4 are illustrated in FIG. 7D.

As there were a number of potential variants to be sampled in each epitope, 11 new variants of 15G11 were designed in an attempt to find an ideal combination that could retain potency but lead to a fully deimmunised clone. For these 15 IgGs the VL v-domain sequences are shown in Table 6, with the VH domains in Table 7. These IgGs were cloned and expressed in IgG1 form, before functional testing as below.

15G11-DI variants—IgG Specificity and Potency Characteristics

'DI' variant IgGs 15G11-DI1-11 were first examined for their binding characteristics by ELISA on human (FIG. 8A) and rhesus (FIG. 8B) ErbB3. Against both human and rhesus ErbB3, all clones other than 15G11-DI11 exhibited strong target binding with curves overlapping with both m24C05 and h24C05.

As ELISA binding is strongly influenced by avidity effects, we then performed a high-sensitivity, solution-phase, Alphascreen competition assay to simultaneously examine the target binding affinity and epitope competition retention with h24C05 (FIG. 9). In this assay, all IgGs other than 15G11-DI11 showed full, concentration dependent inhibition of h24C05 to human ErbB3, with potencies generally being equivalent to, or improved over h24C05 (FIG. 9). IgGs m24C05 and h24C05 exhibited IC50 values of 0.16 nM and 1.25 nM, respectively, which correlates with the Biacore® affinity value differential between those two IgGs shown in Table 5. Exceptions were 15G11-DI3, 15G11-DI4, 15G11-DI10 and 15G11-DI11, whose potencies appeared to be lower than h24C05.

In flow cytometric analyses of binding to human and rhesus ErbB3 (FIG. 10A, B), all clones showed fully saturating, overlapping binding curves. Clones 15G11-DI5, 15G11-DI6, 15G11-D17, 15G11-DI8 and 15G11-DI9 exhibited highest binding to both human and rhesus ErbB3, approximately equivalent to both m24C05 and h24C05.

A key developability factor in CDR-engineered antibodies for therapeutic use is a lack of 'polyreactivity'. Polyreactivity is a significant risk to the pharmacokinetic and safety qualities of any antibody. To ensure the deimmunised lead antibodies were not at risk, they were examined in established polyreactivity binding ELISA assays against dsDNA and human insulin (Avery et al. mAbs, 2018). The majority of IgGs tested in this assay (15G11-DI10 being an exception) showed no sign of polyreactive binding as they exhibited signals below the risk cut-off of 10 and at, or below, the signals of the negative control, clinically successful antibodies Bevacizumab and Ustekinumab (FIG. 11). The positive control antibodies Bococizumab and Briakinumab exhibited the expected strong signals in these assays.

To ascertain if the full biological potency of ErbB3 inhibition had been retained in the key deimmunised leads, clones 15G11, 16B09, 15G11-DI5, 15G11-DI6, 15G11-DI7, 15G11-DI8 and 15G11-DI9 were all analysed over a broad concentration range in the DiscoverX PathHunter eXpress ErbB2-ErbB3 functional assay (FIG. 12A-G). These analyses demonstrated that clones 15G11 (FIG. 12A), 16B09 (FIG. 12B), 15G11-DI5 (FIG. 12C) and 15G11-DI6 (FIG. 12D) all maintained near-identical potency to both m24C05 and h24C05. Clones 15G11-DI7 (FIG. 12E) and 15G11-DI8 (FIG. 12F) exhibited slightly reduced potency. For 15G11-DI9, the curve fit of its data was unreliable (FIG. 12C), so the experiment was repeated and the fit improved, with 15G11-DI9 also showing near identical potency to h24C05 and m24C05, as evidenced by the overlapping response curves (FIG. 13).

For these deimmunised key leads, TCR epitope content was again examined (FIG. 14A-FIG. 14E) and this demonstrated that clones 15G11-DI8 and 15G11-DI9 exhibited significantly reduced immunogenicity risk in comparison to h24C05 and 15G11 where the initial germlining process had, unexpectedly, actually increased risk over h24C05 (FIG. 6A, FIG. 6B). Indeed, clone 15G11-DI9 was found to be fully inert, containing no predicted foreign TCR epitopes at all and only a large number of GE peptides (11).

The combined analyses outlined herein demonstrated that, surprisingly, deep sampling of both germline and non-germline amino acids in the CDRs of these antibodies allowed the simultaneous optimisation of target binding specificity, immunogenicity risk, potency, biophysical stability and chemical stability risks in multiple final molecules. These findings also demonstrate that the beneficial deimmunising outcomes described here could not be achieved using the method of Townsend et al. (2015; PNAS 112: 15354-15359).

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

No limitation with respect to the specific embodiments disclosed herein and set forth in the appended claims is intended nor should any be inferred. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

TABLE 1

Amino acid sequences of 24C05 anti-ERBB3 CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GFTFSDYAMS (SEQ ID NO: 59) | VSTISDGGTYTYYPDNVKG (SEQ ID NO: 65) | EWGDYDGFDY (SEQ ID NO: 72) | RASQEISGYLS (SEQ ID NO: 76) | AASTLDS (SEQ ID NO: 80) | LQYDSYPYT (SEQ ID NO: 82) |

TABLE 1-continued Amino acid sequences of 24C05 anti-ERBB3 CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Kabat | DYAMS (SEQ ID NO: 60) | TISDGGTYTYYPDNVKG (SEQ ID NO: 66) | EWGDYDGFDY (SEQ ID NO: 72) | RASQEISGYLS (SEQ ID NO: 76) | AASTLDS (SEQ ID NO: 80) | LQYDSYPYT (SEQ ID NO:) |
| Chotia | GFTFSDY (SEQ ID NO: 61) | SDGGTY (SEQ ID NO: 67) | EWGDYDGFDY (SEQ ID NO: 72) | RASQEISGYLS (SEQ ID NO: 76) | AASTLDS (SEQ ID NO: 80) | LQYDSYPYT (SEQ ID NO: 82) |
| IMGT | GFTFSDYA (SEQ ID NO: 62) | ISDGGTYT (SEQ ID NO: 68) | AREWGDYDGFDY (SEQ ID NO: 73) | QEISGY (SEQ ID NO: 77) | AAS | LQYDSYPYT (SEQ ID NO: 82) |
| AHo | ASGFTFSDYAMS (SEQ ID NO: 63) | ISDGGTYTYYPDNVKG (SEQ ID NO: 69) | EWGDYDGFD (SEQ ID NO: 74) | ASQEISGY (SEQ ID NO: 78) | AASTLDS (SEQ ID NO: 80) | YDSYPY (SEQ ID NO: 83) |
| AbM | GFTFSDYAMS (SEQ ID NO: 59) | TISDGGTYTY (SEQ ID NO: 70) | EWGDYDGFDY (SEQ ID NO: 72) | RASQEISGYLS (SEQ ID NO: 76) | AASTLDS (SEQ ID NO: 80) | LQYDSYPYT (SEQ ID NO: 82) |
| Contact | SDYAMS (SEQ ID NO: 64) | VSTISDGGTYTY (SEQ ID NO: 71) | AREWGDYDGFD (SEQ ID NO: 75) | ISGYLSWY (SEQ ID NO: 79) | LLIYAASTLD (SEQ ID NO: 81) | LQYDSYPY (SEQ ID NO: 84) |

TABLE 2

Amino acid sequence of h24C05 anti-ERBB3 v-domains and human germline CDR grafts.

| V DOMAIN | Human germline[1] | Amino acid sequence[2] |
|---|---|---|
| h24C05-VH | IGHV3-11 | QVQLVESGGGLVKPGGSLRLSCAASGFTFSDYAMSWIRQAPGKGLEWVSTISDGGTYTYYPDNVKGRFTISRDNAKNSLYLQMNSLRAEDTAVYYCAREWGDYDGFDYWGQGTLVTVSS (SEQ ID NO: 85) |
| VH graft | IGHV3-11[3] | QVQLVESGGGLVKPGGSLRLSCAASGFTFSDYAMSWIRQAPGKGLEWVSTISDGGTYTYYPDNVKGRFTISRDNAKNSLYLQMNSLRAEDTAVYYCAREWGDYDGFDYWGQGTLVTVSS (SEQ ID NO: 86) |
| h24C05-VL | IGKV1-16 | DIQMTQSPSSLSASVGDRVTITCRASQEISGYLSWFQQKPGKAPKSLIYAASTLDSGVPSRFSGSGSGTDFTLTISSLQPEDFATTYCLQYDSYPYTFGGGTKVEIK (SEQ ID NO: 87) |
| VL graft | IGKV1-39[3] | DIQMTQSPSSLSASVGDRVTITCRASQEISGYLSWYQQKPGKAPKLLIYAASTLDSGVPSRFSGSGSGTDFTLTISSLQPEDFATTYCLQYDSYPYTFGGGTKVEIK (SEQ ID NO: 88) |

[1]Human germline definitions used for grafting, based on IMGT system.
[2]CDR residues are in bold and underlined. As noted above, the "Unified" CDR definitions used in this manuscript are an expanded definition in comparison to the classical Kabat definition. Each sequence above shows the framework regions (FRs) and the CDRs in the following order: FR1-CDR1-FR2-CDR2-FR3-CDR3-FR4.
[3]Grafts are fully germline in the framework regions, used as the template for CDR mutant library construction.

TABLE 3

Amino acid sequences of unique CDRs from 658 unique anti-ERBB3 v-domains.

| LCDR1 | LCDR2 | LCDR3 | HCDR1 | HCDR2 | HCDR2 | HCDR3 |
|---|---|---|---|---|---|---|
| RASQSISSYLS (SEQ ID NO: 16) | AASSLDS (SEQ ID NO: 22) | LQYDSTPYT (SEQ ID NO: 23) | GFTFSDYAMS (SEQ ID NO: 109) | VGTISDGGTTIYYADNVKG (SEQ ID NO: 117) | VSTISDSGSYIYYADSVKG (SEQ ID NO: 14) | EFGDYDGFDF (SEQ ID NO: 181) |
| RASQEISSYLS (SEQ ID NO: 21) | AASSLQS (SEQ ID NO: 17) | LQYYSYPYT (SEQ ID NO: 98) | GFTFSDYEMS (SEQ ID NO: 110) | VSTISDDGSTTYYADSVKG (SEQ ID NO: 118) | VSTISDSGSYIYYPDNVKG (SEQ ID NO: 155) | EFGDYDGFDY (SEQ ID NO: 182) |

TABLE 3-continued

Amino acid sequences of unique CDRs from 658 unique anti-ERBB3 v-domains.

| LCDR1 | LCDR2 | LCDR3 | HCDR1 | HCDR2 | HCDR2 | HCDR3 |
|---|---|---|---|---|---|---|
| RASQIISSYLS (SEQ ID NO: 52) | AASTLQS (SEQ ID NO: 26) | LQYDSTPLT (SEQ ID NO: 18) | GFTFSDYGMS (SEQ ID NO: 13) | VSTISDGGSTIYYADNVKG (SEQ ID NO: 119) | VSTISDSGSYIYYPDSVKG (SEQ ID NO: 156) | ELGDYDGFDY (SEQ ID NO: 20) |
| RASQSISSYLN (SEQ ID NO: 50) | AASNLQS (SEQ ID NO: 93) | QQYDSYPYT (SEQ ID NO: 99) | GFTFSDYHMS (SEQ ID NO: 111) | VSTISDGGSTIYYADSVKG (SEQ ID NO: 120) | VSTISDSGSYTYYADNVKG (SEQ ID NO: 157) | ELGDYDGWDY (SEQ ID NO: 183) |
| RASQSISGYLN (SEQ ID NO: 89) | AASSLHS (SEQ ID NO: 94) | LQYSTPLT (SEQ ID NO: 53) | GFTFSDYNMS (SEQ ID NO: 112) | VSTISDGGSTIYYPDNVKG (SEQ ID NO: 121) | VSTISDSGSYTYYADSVKG (SEQ ID NO: 54) | EMGDYDGFDY (SEQ ID NO: 184) |
| RASQEISSYLN (SEQ ID NO: 90) | EASSLDS (SEQ ID NO: 95) | LQYDSYPLT (SEQ ID NO: 100) | GFTFSDYQMS (SEQ ID NO: 113) | VSTISDGGSTIYYPDSVKG (SEQ ID NO: 122) | VSTISDSGSYTYYPDNVKG (SEQ ID NO: 158) | EQGDYDGFDI (SEQ ID NO: 185) |
| RASQSISGYLS (SEQ ID NO: 30) | AASSLKS (SEQ ID NO: 96) | QQYDSTPYT (SEQ ID NO: 101) | GFTFSDYRMS (SEQ ID NO: 114) | VSTISDGGSTTYYADNVKG (SEQ ID NO: 123) | VSTISDSGSYTYYPDSVKG (SEQ ID NO: 19) | EWGDADGFDY (SEQ ID NO: 186) |
| RASQEISGYLN (SEQ ID NO: 91) | EASSLQS (SEQ ID NO: 97) | LQSDSTPYT (SEQ ID NO: 102) | GFTFSDYSMS (SEQ ID NO: 24) | VSTISDGGSTTYYADSVKG (SEQ ID NO: 124) | VSTISDSGTTIYYADNVKG (SEQ ID NO: 56) | EWGDDDGFDY (SEQ ID NO: 187) |
| RASQNISSYLS (SEQ ID NO: 92) | | LQSDSTPLT (SEQ ID NO: 103) | GFTFSDYTMS (SEQ ID NO: 115) | VSTISDGGSTTYYPDNVKG (SEQ ID NO: 125) | VSTISDSGTTIYYADSVKG (SEQ ID NO: 159) | EWGDEDGFDY (SEQ ID NO: 188) |
| | | QQYDSYPLT (SEQ ID NO: 104) | GFTFSDYVMS (SEQ ID NO: 116) | VSTISDGGSTTYYPDSVKG (SEQ ID NO: 126) | VSTISDSGTTTYYADNVKG (SEQ ID NO: 160) | EWGDHDGFDY (SEQ ID NO: 189) |
| | | LQYYSYPLT (SEQ ID NO: 105) | | VSTISDGGSYIYYADNVKG (SEQ ID NO: 127) | VSTISDSGTTTYYADSVKG (SEQ ID NO: 161) | EWGDLDGFDY (SEQ ID NO: 190) |
| | | LQYYSTPYT (SEQ ID NO: 106) | | VSTISDGGSYIYYADSVKG (SEQ ID NO: 128) | VSTISDSGTTTYYPDNVKG (SEQ ID NO: 162) | EWGDMDGFDR (SEQ ID NO: 191) |
| | | QQYDSTPLT (SEQ ID NO: 107) | | VSTISDGGSYIYYPDNVKG (SEQ ID NO: 129) | VSTISDSGTTTYYPDSVKG (SEQ ID NO: 163) | EWGDMDGFDY (SEQ ID NO: 192) |
| | | LQYDSYHLT (SEQ ID NO: 108) | | VSTISDGGSYIYYPDSVKG (SEQ ID NO: 130) | VSTISDSGTYIYYADNVKG (SEQ ID NO: 164) | EWGDNDGFDY (SEQ ID NO: 193) |
| | | | | VSTISDGGSYTYYADNVKG (SEQ ID NO: 31) | VSTISDSGTYIYYADSVKG (SEQ ID NO: 165) | EWGDQDGFDY (SEQ ID NO: 194) |
| | | | | VSTISDGGSYTYYADSVKG (SEQ ID NO: 28) | VSTISDSGTYIYYPDNVKG (SEQ ID NO: 166) | EWGDSDGFDY (SEQ ID NO: 195) |
| | | | | VSTISDGGSYTYYPDNVKG (SEQ ID NO: 131) | VSTISDSGTYIYYPDSVKG (SEQ ID NO: 167) | EWGDTDGFDY (SEQ ID NO: 196) |
| | | | | VSTISDGGSYTYYPDSVKG (SEQ ID NO: 57) | VSTISDSGTYTYYADNVKG (SEQ ID NO: 168) | EWGDWDGFDY (SEQ ID NO: 197) |
| | | | | VSTISDGGTTIYYADNVKG (SEQ ID NO: 132) | VSTISDSGTYTYYADSVKG (SEQ ID NO: 169) | EWGDYDGCDY (SEQ ID NO: 198) |
| | | | | VSTISDGGTTIYYADSVKG (SEQ ID NO: 133) | VSTISDSGTYTYYPDNVKG (SEQ ID NO: 170) | EWGDYDGFDA (SEQ ID NO: 199) |
| | | | | VSTISDGGTTIYYPDSVKG (SEQ ID NO: 134) | VSTISDSGTYTYYPDSVKG (SEQ ID NO: 25) | EWGDYDGFDD (SEQ ID NO: 200) |

TABLE 3-continued

Amino acid sequences of unique CDRs from 658 unique anti-ERBB3 v-domains.

| LCDR1 | LCDR2 | LCDR3 | HCDR1 | HCDR2 | HCDR2 | HCDR3 |
|---|---|---|---|---|---|---|
| | | | | VSTISDGGTTTYYADNVKG (SEQ ID NO: 135) | VSTISNSGTYTYYADSVKG (SEQ ID NO: 171) | EWGDYDGFDE (SEQ ID NO: 29) |
| | | | | VSTISDGGTTTYYADSVKG (SEQ ID NO: 136) | VSTISSGGSYIYYPDSVKG (SEQ ID NO: 172) | EWGDYDGFDF (SEQ ID NO: 15) |
| | | | | VSTISDGGTTTYYPDNVKG (SEQ ID NO: 137) | VSTISSGGSYTYYPDSVKG (SEQ ID NO: 173) | EWGDYDGFDH (SEQ ID NO: 27) |
| | | | | VSTISDGGTTTYYPDSVKG (SEQ ID NO: 138) | VSTISSSGSYTYYADNVKG (SEQ ID NO: 174) | EWGDYDGFDI (SEQ ID NO: 201) |
| | | | | VSTISDGGTYIYYADNVKG (SEQ ID NO: 139) | VSTISSSGTTTYYADSVKG (SEQ ID NO: 175) | EWGDYDGFDK (SEQ ID NO: 202) |
| | | | | VSTISDGGTYIYYADSVKG (SEQ ID NO: 140) | VSTISSSGTYIYYADNVKG (SEQ ID NO: 176) | EWGDYDGFDL (SEQ ID NO: 203) |
| | | | | VSTISDGGTYIYYPDNVKG (SEQ ID NO: 141) | VSYISDGGSYIYYADSVKG (SEQ ID NO: 177) | EWGDYDGFDM (SEQ ID NO: 204) |
| | | | | VSTISDGGTYIYYPDSVKG (SEQ ID NO: 142) | VSYISDGGSYTYYADNVKG (SEQ ID NO: 178) | EWGDYDGFDN (SEQ ID NO: 55) |
| | | | | VSTISDGGTYTYYADNVKG (SEQ ID NO: 143) | VSYISDGGTTIYYADSVKG (SEQ ID NO: 179) | EWGDYDGFDQ (SEQ ID NO: 205) |
| | | | | VSTISDGGTYTYYADSVKG (SEQ ID NO: 144) | VSYISDSGTYTYYPDSVKG (SEQ ID NO: 180) | EWGDYDGFDR (SEQ ID NO: 206) |
| | | | | VSTISDGGTYTYYPDNVKG (SEQ ID NO: 145) | | EWGDYDGFDS (SEQ ID NO: 207) |
| | | | | VSTISDGGTYTYYPDSVKG (SEQ ID NO: 146) | | EWGDYDGFDV (SEQ ID NO: 208) |
| | | | | VSTISDSGSTIYYADNVKG (SEQ ID NO: 147) | | EWGDYDGFDW (SEQ ID NO: 209) |
| | | | | VSTISDSGSTIYYADSVKG (SEQ ID NO: 58) | | EWGDYDGFDY (SEQ ID NO: 210) |
| | | | | VSTISDSGSTIYYPDNVKG (SEQ ID NO: 148) | | EWGDYDGFHY (SEQ ID NO: 211) |
| | | | | VSTISDSGSTIYYPDSVKG (SEQ ID NO: 149) | | EWGDYDGIDY (SEQ ID NO: 212) |
| | | | | VSTISDSGSTTYYADNVKG (SEQ ID NO: 150) | | EWGDYDGLDY (SEQ ID NO: 213) |
| | | | | VSTISDSGSTTYYADSVKG (SEQ ID NO: 151) | | EWGDYDGWDY (SEQ ID NO: 214) |
| | | | | VSTISDSGSTTYYPDNVKG (SEQ ID NO: 152) | | EWGDYDGYDY (SEQ ID NO: 215) |

TABLE 3-continued

Amino acid sequences of unique CDRs from 658 unique anti-ERBB3 v-domains.

| LCDR1 | LCDR2 | LCDR3 | HCDR1 | HCDR2 | HCDR2 | HCDR3 |
|---|---|---|---|---|---|---|
| | | | | VSTISDSGSTTYYPDSVKG (SEQ ID NO: 153) | | EYGDYDGFDY (SEQ ID NO: 51) |
| | | | | VSTISDSGSYIYYADNVKG (SEQ ID NO: 154) | | MWGDYDGFDY (SEQ ID NO: 216) |

TABLE 4

Amino acid sequences of CDRs of unique, library-derived and designer, human/rhesus cross-reactive anti-ERBB IgGs.

| Clone | LCDR1 | LCDR2 | LCDR3 | HCDR1 | HCDR2 | HCDR3 |
|---|---|---|---|---|---|---|
| 15D10 | RASQSISSYLS (SEQ ID NO: 16) | AASTLQS (SEQ ID NO: 26) | LQYDSTPLT (SEQ ID NO: 18) | GFTFSDYGMS (SEQ ID NO: 13) | VSTISDGGSYTYYADNVKG (SEQ ID NO: 31) | EWGDYDGFDF (SEQ ID NO: 15) |
| 17H10 | RASQSISGYLS (SEQ ID NO: 30) | AASTLQS (SEQ ID NO: 26) | LQYDSTPYT (SEQ ID NO: 23) | GFTFSDYGMS (SEQ ID NO: 13) | VSTISDGGSYTYYADSVKG (SEQ ID NO: 28) | EWGDYDGFDE (SEQ ID NO: 29) |
| 09D12 | RASQSISSYLN (SEQ ID NO: 50) | AASSLDS (SEQ ID NO: 22) | LQYDSTPLT (SEQ ID NO: 18) | GFTFSDYGMS (SEQ ID NO: 13) | VSTISDGGSYTYYADSVKG (SEQ ID NO: 28) | EYGDYDGFDY (SEQ ID NO: 51) |
| 15D03 | RASQEISSYLS (SEQ ID NO: 21) | AASSLQS (SEQ ID NO: 17) | LQYDSTPLT (SEQ ID NO: 18) | GFTFSDYGMS (SEQ ID NO: 13) | VSTISDSGSYIYYADSVKG (SEQ ID NO: 14) | EWGDYDGFDH (SEQ ID NO: 27) |
| 11H02 | RASQIISSYLS (SEQ ID NO: 52) | AASSLDS (SEQ ID NO: 22) | LQYYSTPLT (SEQ ID NO: 53) | GFTFSDYGMS (SEQ ID NO: 13) | VSTISDSGSYTYYADSVKG (SEQ ID NO: 54) | EWGDYDGFDN (SEQ ID NO: 55) |
| 15G11 | RASQEISSYLS (SEQ ID NO: 21) | AASSLDS (SEQ ID NO: 22) | LQYDSTPYT (SEQ ID NO: 23) | GFTFSDYGMS (SEQ ID NO: 13) | VSTISDSGSYTYYPDSVKG (SEQ ID NO: 19) | ELGDYDGFDY (SEQ ID NO: 20) |
| 15E02 | RASQSISSYLS (SEQ ID NO: 16) | AASSLQS (SEQ ID NO: 17) | LQYDSTPLT (SEQ ID NO: 18) | GFTFSDYGMS (SEQ ID NO: 13) | VSTISDSGTTIYYADNVKG (SEQ ID NO: 56) | EYGDYDGFDY (SEQ ID NO: 51) |
| 09H02 | RASQSISSYLS (SEQ ID NO: 16) | AASSLQS (SEQ ID NO: 17) | LQYDSTPLT (SEQ ID NO: 18) | GFTFSDYSMS (SEQ ID NO: 24) | VSTISDGGSYTYYPDSVKG (SEQ ID NO: 57) | ELGDYDGFDY (SEQ ID NO: 20) |
| 16B09 | RASQEISSYLS (SEQ ID NO: 21) | AASTLQS (SEQ ID NO: 26) | LQYDSTPLT (SEQ ID NO: 18) | GFTFSDYSMS (SEQ ID NO: 24) | VSTISDSGTYTYYPDSVKG (SEQ ID NO: 25) | EWGDYDGFDF (SEQ ID NO: 15) |
| TTP | RASQSISSYLN (SEQ ID NO: 50) | AASSLQS (SEQ ID NO: 17) | LQYDSTPLT (SEQ ID NO: 18) | GFTFSDYGMS (SEQ ID NO: 13) | VSTISDSGSTIYYADSVKG (SEQ ID NO: 58) | EYGDYDGFDY (SEQ ID NO: 51) |
| MH1 | RASQSISSYLS (SEQ ID NO: 16) | AASSLQS (SEQ ID NO: 17) | LQYDSTPLT (SEQ ID NO: 18) | GFTFSDYGMS (SEQ ID NO: 13) | VSTISDSGSYIYYADSVKG (SEQ ID NO: 14) | ELGDYDGFDY (SEQ ID NO: 20) |
| MH2 | RASQSISSYLS (SEQ ID NO: 16) | AASSLQS (SEQ ID NO: 17) | LQYDSTPLT (SEQ ID NO: 18) | GFTFSDYGMS (SEQ ID NO: 13) | VSTISDSGSYIYYADSVKG (SEQ ID NO: 14) | EWGDYDGFDF (SEQ ID NO: 15) |
| MH3 | RASQSISSYLS (SEQ ID NO: 16) | AASSLQS (SEQ ID NO: 17) | LQYDSTPLT (SEQ ID NO: 18) | GFTFSDYSMS (SEQ ID NO: 24) | VSTISDSGSTIYYADSVKG (SEQ ID NO: 58) | EWGDYDGFDF (SEQ ID NO: 15) |
| MH4 | RASQSISSYLS (SEQ ID NO: 16) | AASSLQS (SEQ ID NO: 17) | LQYDSTPLT (SEQ ID NO: 18) | GFTFSDYGMS (SEQ ID NO: 13) | VSTISDSGSYIYYADSVKG (SEQ ID NO: 14) | EWGDYDGFDE (SEQ ID NO: 29) |

TABLE 4-continued

Amino acid sequences of CDRs of unique, library-derived and designer, human/rhesus cross-reactive anti-ERBB3 IgGs.

| Clone | LCDR1 | LCDR2 | LCDR3 | HCDR1 | HCDR2 | HCDR3 |
|---|---|---|---|---|---|---|
| MH5 | RASQSISSYLS (SEQ ID NO: 16) | AASSLQS (SEQ ID NO: 17) | LQYDSTPLT (SEQ ID NO: 18) | GFTFSDYGMS (SEQ ID NO: 13) | VSTISDSGSTIYYADSVKG (SEQ ID NO: 58) | EYGDYDGFDY (SEQ ID NO: 51) |

TABLE 5

BIACORE ® affinity values for IgG binding to human and rhesus monomeric ERBB3.

| | Human ERBB3 | | | | Rhesus ERBB3 | | | |
|---|---|---|---|---|---|---|---|---|
| Clone name | ka (1/Ms) | kd (1/s) | Chi2 | KD (nM) | ka (1/Ms) | kd (1/s) | Chi2 | KD (nM) |
| 24C05 | 4.60E+07 | 6.70E−04 | 0.117 | 0.014 | 1.80E+07 | 4.40E−04 | 0.02 | 0.024 |
| h24C05 | 2.50E+07 | 9.60E−04 | 0.164 | 0.039 | 4.10E+06 | 7.40E−04 | 0.037 | 0.18 |
| 15G11 | 1.60E+07 | 1.20E−03 | 0.141 | 0.078 | 3.30E+06 | 1.10E−03 | 0.041 | 0.33 |
| 16809 | 1.60E+07 | 1.40E−03 | 0.223 | 0.089 | 1.30E+07 | 2.70E−03 | 0.044 | 0.21 |
| 15D10 | 1.40E+07 | 1.90E−03 | 0.195 | 0.14 | 3.30E+06 | 1.80E−03 | 0.057 | 0.54 |
| 17H10 | 9.30E+06 | 1.70E−03 | 0.165 | 0.19 | 2.70E+06 | 1.80E−03 | 0.035 | 0.65 |
| 15D03 | 1.10E+07 | 3.00E−03 | 0.204 | 0.26 | 1.80E+07 | 4.70E−03 | 0.117 | 0.26 |
| MH4 | 1.10E+07 | 2.90E−03 | 0.158 | 0.26 | 2.20E+07 | 4.70E−03 | 0.099 | 0.21 |
| MH2 | 1.10E+07 | 2.90E−03 | 0.177 | 0.27 | 2.00E+07 | 4.80E−03 | 0.099 | 0.23 |
| 09D12 | 1.30E+07 | 3.50E−03 | 0.149 | 0.27 | 1.10E+07 | 7.40E−03 | 0.049 | 0.69 |
| 09H02 | 3.10E+06 | 1.30E−03 | 0.272 | 0.43 | 1.10E+07 | 2.70E−03 | 0.027 | 0.25 |
| MH1 | 6.80E+06 | 3.50E−03 | 0.124 | 0.51 | 1.30E+07 | 5.60E−03 | 0.081 | 0.45 |
| 15E02 | 6.30E+06 | 3.90E−03 | 0.229 | 0.61 | 3.70E+06 | 9.50E−03 | 0.034 | 2.5 |
| MH5 | 5.80E+06 | 4.10E−03 | 0.166 | 0.71 | 1.20E+07 | 6.00E−03 | 0.076 | 0.51 |
| MH3 | 7.60E+06 | 6.50E−03 | 0.143 | 0.85 | 1.80E+07 | 1.10E−02 | 0.057 | 0.63 |
| TTP | 6.20E+07 | 7.30E−02 | 1.21 | 1.2 | ND | ND | ND | ND |
| 11H02 | 6.10E+06 | 8.10E−03 | 1.04 | 1.3 | 1.70E+07 | 3.70E−02 | 0.332 | 2.1 |

TABLE 6

Amino acid sequences of VL-domains of unique, deimmunised anti-ERBB3 IgGs.

| Clone | VL |
|---|---|
| 15G11-DI1 | DIQMTQSPSSLSASVGDRVTITCRASQEISSYLSWYQQKPGKAPKLLIYAASSLDTGVPSRFSGSGSGTDFTLTISSLQPEDFATYYCLQYDSTPYTFGGGTKVEIK (SEQ ID NO: 217) |
| 15G11-DI2 | DIQMTQSPSSLSASVGDRVTITCRASQEISTYLSWYQQKPGKAPKLLIYAASSLDTGVPSRFSGSGSGTDFTLTISSLQPEDFATYYCLQYDSTPYTFGGGTKVEIK (SEQ ID NO: 218) |
| 15G11-DI3 | DIQMTQSPSSLSASVGDRVTITCRASQEISSYLSWYQQKPGKAPKLLIYAASSLDTGVPSRFSGSGSGTDFTLTISSLQPEDFATYYCLQYDSSPYTFGGGTKVEIK (SEQ ID NO: 219) |
| 15G11-DI4 | DIQMTQSPSSLSASVGDRVTITCRASQEISTYLSWYQQKPGKAPKLLIYAASSLDTGVPSRFSGSGSGTDFTLTISSLQPEDFATYYCLQYDSSPYTFGGGTKVEIK (SEQ ID NO: 220) |
| 15G11-DI5 | DIQMTQSPSSLSASVGDRVTITCRASQEISSYLSWYQQKPGKAPKLLIYAASSLDTGVPSRFSGSGSGTDFTLTISSLQPEDFATYYCLQYDSTPYTFGGGTKVEIK (SEQ ID NO: 221) |
| 15G11-DI6 | DIQMTQSPSSLSASVGDRVTITCRASQEISTYLSWYQQKPGKAPKLLIYAASSLDTGVPSRFSGSGSGTDFTLTISSLQPEDFATYYCLQYDSTPYTFGGGTKVEIK (SEQ ID NO: 222) |
| 15G11-DI7 | DIQMTQSPSSLSASVGDRVTITCRASQEISSYLSWYQQKPGKAPKLLIYAASSLDTGVPSRFSGSGSGTDFTLTISSLQPEDFATYYCLQYDSSPYTFGGGTKVEIK (SEQ ID NO: 223) |
| 15G11-DI8 | DIQMTQSPSSLSASVGDRVTITCRASQEISTYLSWYQQKPGKAPKLLIYAASSLDTGVPSRFSGSGSGTDFTLTISSLQPEDFATYYCLQYDSSPYTFGGGTKVEIK (SEQ ID NO: 224) |

TABLE 6-continued

Amino acid sequences of VL-domains of unique, deimmunised anti-ERBB3 IgGs.

| Clone | VL |
|---|---|
| 15G11-DI9 | DIQMTQSPSSLSASVGDRVTITCRASQEISTYLSWYQQKPGKAPKLLIYAASTLQS<br>GVPSRFSGSGSGTDFTLTISSLQPEDFATYYCLQYDSSPLTFGGGTKVEIK<br>(SEQ ID NO: 225) |
| 15G11-DI10 | DIQMTQSPSSLSASVGDRVTITCRASQEISSYLSWYQQKPGKAPKLLAYAASSLDS<br>GVPSRFSGSGSGTDFTLTISSLQPEDFATYYCLQYDSTPYTFGGGTKVEIK<br>(SEQ ID NO: 226) |
| 15G11-DI11 | DIQMTQSPSSLSASVGDRVTITCRASQEASSYLSWYQQKPGKAPKLLAYAASSLDS<br>GVPSRFSGSGSGTDFTLTISSLQPEDFATYYCLQYDSSPYTFGGGTKVEIK<br>(SEQ ID NO: 227) |

TABLE 7

Amino acid sequences of VH-domains of unique, deimmunised anti-ERBB3 IgGs.

| Clone | VH |
|---|---|
| 15G11-DI1 | QVQLVESGGGLVKPGGSLRLSCAASGFTFSDYGMSWVRQAPGKGLEWVSTISDSGSYT<br>YYPDSVKGRFTISRDNAKNSLYLQMNSLRAEDTAVYYCARELGDYDGFDYWGQGTLVT<br>VSS<br>(SEQ ID NO: 228) |
| 15G11-DI2 | QVQLVESGGGLVKPGGSLRLSCAASGFTFSDYGMSWVRQAPGKGLEWVSTISDSGSYT<br>YYPDSVKGRFTISRDNAKNSLYLQMNSLRAEDTAVYYCARELGDYDGFDYWGQGTLVT<br>VSS<br>(SEQ ID NO: 229) |
| 15G11-DI3 | QVQLVESGGGLVKPGGSLRLSCAASGFTFSDYGMSWVRQAPGKGLEWVSTISDSGSYT<br>YYPDSVKGRFTISRDNAKNSLYLQMNSLRAEDTAVYYCARELGDYDGFDYWGQGTLVT<br>VSS<br>(SEQ ID NO: 230) |
| 15G11-DI4 | QVQLVESGGGLVKPGGSLRLSCAASGFTFSDYGMSWVRQAPGKGLEWVSTISDSGSYT<br>YYPDSVKGRFTISRDNAKNSLYLQMNSLRAEDTAVYYCARELGDYDGFDYWGQGTLVT<br>VSS<br>(SEQ ID NO: 231) |
| 15G11-DI5 | QVQLVESGGGLVKPGGSLRLSCAASGFTFSDYSMSWIRQAPGKGLEWVSTISDSGTYT<br>YYPDSVKGRFTISRDNAKNSLYLQMNSLRAEDTAVYYCAREWGDYDGFDFWGQGTLVT<br>VSS<br>(SEQ ID NO: 232) |
| 15G11-DI6 | QVQLVESGGGLVKPGGSLRLSCAASGFTFSDYSMSWIRQAPGKGLEWVSTISDSGTYT<br>YYPDSVKGRFTISRDNAKNSLYLQMNSLRAEDTAVYYCAREWGDYDGFDFWGQGTLVT<br>VSS<br>(SEQ ID NO: 233) |
| 15G11-DI7 | QVQLVESGGGLVKPGGSLRLSCAASGFTFSDYSMSWIRQAPGKGLEWVSTISDSGTYT<br>YYPDSVKGRFTISRDNAKNSLYLQMNSLRAEDTAVYYCAREWGDYDGFDFWGQGTLVT<br>VSS<br>(SEQ ID NO: 234) |
| 15G11-DI8 | QVQLVESGGGLVKPGGSLRLSCAASGFTFSDYSMSWIRQAPGKGLEWVSTISDSGTYT<br>YYPDSVKGRFTISRDNAKNSLYLQMNSLRAEDTAVYYCAREWGDYDGFDFWGQGTLVT<br>VSS<br>(SEQ ID NO: 235) |
| 15G11-DI9 | QVQLVESGGGLVKPGGSLRLSCAASGFTFSDYSMSWIRQAPGKGLEWVSTISDSGTYT<br>YYPDSVKGRFTISRDNAKNSLYLQMNSLRAEDTAVYYCAREWGDYDGFDFWGQGTLVT<br>VSS<br>(SEQ ID NO: 236) |
| 15G11-DI10 | QVQLVESGGGLVKPGGSLRLSCAASGFTFSDYGMSWVRQAPGKGLEWVSTISDSGSYT<br>YYPDSVKGRFTISRDNAKNSLYLQMNSLRAEDTAVYYCARELGDYDGFDYWGQGTLVT<br>VSS<br>(SEQ ID NO: 237) |

TABLE 7-continued

Amino acid sequences of VH-domains of unique, deimmunised anti-ERBB3 IgGs.

| Clone | VH |
|---|---|
| 15G11-DI11 | QVQLVESGGGLVKPGGSLRLSCAASGFTFSDYGMSWVRQAPGKGLEWVSTISDSGSYT YYPDSVKGRFTISRDNAKNSLYLQMNSLRAEDTAVYYCARELGDYDGFDYWGQGTLVT VSS (SEQ ID NO: 238) |

TABLE 8

Examples of antibody variable region amino acid sequences.

Antibody 15G11-DI9 heavy chain variable (VH) region
QVQLVESGGGLVKPGGSLRLSCAASGFTFSDYSMSWIRQAPGKGLEVVS
TISDSGTYTYYPDSVKGRFTISRDNAKNSLYLQMNSLRAEDTAVYYCARE
WGDYDGFDFWGQGTLVTVSS (SEQ ID NO: 236)

Antibody 15G11-DI9 light chain variable (VL) region
DIQMTQSPSSLSASVGDRVTITCRASQEISTYLSWYQQKPGKAPKLLIYA
ASTLQSGVPSRFSGSGSGTDFTLTISSLQPEDFATYYCLQYDSSPLTFGG
GTKVEIK (SEQ ID NO: 225)

Antibody 15G11-DI5 heavy chain variable (VH) region
QVQLVESGGGLVKPGGSLRLSCAASGFTFSDYSMSWIRQAPGKGLEWVST
ISDSGTYTYYPDSVKGRFTISRDNAKNSLYLQMNSLRAEDTAVYYCAREW
GDYDGFDFWGQGTLVTVSS (SEQ ID NO: 232)

Antibody 15G11-DI5 light chain variable (VL) region
DIQMTQSPSSLSASVGDRVTITCRASQEISSYLSWYQQKPGKAPKLLIYA
ASSLDTGVPSRFSGSGSGTDFTLTISSLQPEDFATYYCLQYDSTPYTFGG
GTKVEIK (SEQ ID NO: 221)

Antibody 15G11 heavy chain variable (VH) region
QVQLVESGGGLVKPGGSLRLSCAASGFTFSDYSMSWIRQAPGKGLEWVST
ISDSGSYTYYPDSVKGRFTISRDNAKNSLYLQMNSLRAEDTAVYYCAREL
GDYDGFDYWGQGTLVTVSS (SEQ ID NO: 253)

Antibody 15G11 light chain variable (VL) region
DIQMTQSPSSLSASVGDRVTITCRASQEISSYLSWYQQKPGKAPKLLIYA
ASSLDSGVPSRFSGSGSGTDFTLTISSLQPEDFATYYCLQYDSTPYTFGG
GTKVEIK (SEQ ID NO: 254)

Antibody 16B09 heavy chain variable (VH) region
QVQLVESGGGLVKPGGSLRLSCAASGFTFSDYSMSWIRQAPGKGLEWVST
ISDSGTYTYYPDSVKGRFTISRDNAKNSLYLQMNSLRAEDTAVYYCAREW
GDYDGFDFWGQGTLVTVSS (SEQ ID NO: 255)

Antibody 16B09 light chain variable (VL) region
DIQMTQSPSSLSASVGDRVTITCRASQEISSYLSVVYQQKPGKAPKLLIY
AASTLQSGVPSRFSGSGSGTDFTLTISSLQPEDFATYYCLQYDSTPLTFG
GGTKVEIK (SEQ ID NO: 256)

TABLE 9

Examples of antibody Fc region amino acid sequences.

Human IgG4 wild type
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESKYGPPCPSCPAPEFLGGPSVFLFPPKPKDTLMISRTPEVTCVVVDVS
QED PEVQFNWYVDGVEVHNAKTKPREEQFNSTYRVVSVLTVLHQDWL
NGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTV
DKSRWQEGNVFSCSVMHEALHNHYTQKSLSLSLGK
(SEQ ID NO: 239)

Human IgG4(S228P)
ASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRV
ESKYGPPCPPCPAPEFLGGPSVFLFPPKPKDTLMISRTPEVTCVVVDVS
QED PEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVD
KSRWQEGNVFSCSVMHEALHNHYTQKSLSLSLGK
(SEQ ID NO: 240)

Human IgG1 wild type
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPS<u>RDELT</u>KNQ
VSLTCLVKGFYPSDIAVEWESNGQPENNYKTTPPVLDSDGSFFLYSKLT
VDKSRWQQGNVFSCSVMHEALHNHYTQKSLSLSPGK
(SEQ ID NO: 241)

Human IgG1-3M
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPEAAGAPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPS<u>RDELT</u>KNQ
VSLTCLVKGFYPSDIAVEWESNGQPENNYKTTPPVLDSDGSFFLYSKLT
VDKSRWQQGNVFSCSVMHEALHNHYTQKSLSLSPGK
(SEQ ID NO: 242)

Human IgG2 wild type
ASTKGPSVFPLAPCSRSTSESTAALGCLVKDYFPEPVTVSWNSGALTSG
VHTFPAVLQSSGLYSLSSVVTVPSSNFGTQTYTCNVDHKPSNTKVDKTV
ERKCCVECPPCPAPPVAGPSVFLFPPKPKDTLMISRTPEVTCVVVDVSH
EDPEVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLT
CLVKGFYPSDISVEWESNGQPENNYKTTPPMLDSDGSFFLYSKLTVDKS
RWQQGNVFSCSVMHEALHNHYTQKSLSLSPGK (SEQ ID NO: 243)

Human IgG1 wild type "REEM" allotype
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPS<u>REEMT</u>KNQ
VSLTCLVKGFYPSDIAVEWESNGQPENNYKTTPPVLDSDGSFFLYSKLT
VDKSRWQQGNVFSCSVMHEALHNHYTQKSLSLSPGK
(SEQ ID NO: 244)

Human IgG1-3M "REEM" allotype
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPEAAGAPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPS<u>REEMK</u>NQV
SLTCLVKGFYPSDIAVEWESNGQPENNYKTTPPVLDSDGSFFLYSKLTV
DKSRWQQGNVFSCSVMHEALHNHYTQKSLSLSPGK
(SEQ ID NO: 245)

TABLE 10

Examples of ERBB3 protein amino acid sequences.

Human ERBB3 sequence
MRANDALQVLGLLFSLARGSEVGNSQAVCPGTLNGLSVTGDAENQYQTLY
KLYERCEVVMGNLEIVLIGHNADLSFLQWIREVTGYVLVAMNEFSTLPLP
NLRVVRGTQVYDGKFAIFVMLNYNTNSSHALRQLRLTQLTEILSGGVYIE
KNDKLCHMDTIDWRDIVRDRDAEIVVKDNGRSCPPCHEVCKGRCWGPGSE
DCQTLTKTICAPQCNGHCFGPNPNQCCHDECAGGCSGPQDTDCFACRHFN
DSGACVPRCPQPLVYNKLTFQLEPNPHTKYQYGGVCVASCPHNFVVDQTS
CVRACPPDKMEVDKNGLKMCEPCGGLCPKACEGTGSGSRFQTVDSSNIDG
FVNCTKILGNLDFLITGLNGDPWHKIPALDPEKLNVFRTVREITGYLNIQ
SWPPHMHNFSVFSNLTTIGGRSLYNRGFSLLIMKNLNVTSLGFRSLKEIS
AGRIYISANRQLCYHHSLNWTKVLRGPTEERLDIKHNRPRRDCVAEGKVC
DPLCSSGGCWGPGPGQCLSCRNYSRGGVCVTHCNFLNGEPREFAHEAECF
SCHPECQPMEGTATCNGSGSDTCAQCAHFRDGPHCVSSCPHGVLGAKGPI
YKYPDVQNECRPCHENCTQGCKGPELQDCLGQTLVLIGKTHLTMALTVIA
GLVVIFMMLGGTFLYWRGRRIQNKRAMRRYLERGESIEPLDPSEKANKVL
ARIFKETELRKLKVLGSGVFGTVHKGVWIPEGESIKIPVCIKVIEDKSGR
QSFQAVTDHMLAIGSLDHAHIVRLLGLCPGSSLQLVTQYLPLGSLLDHVR
QHRGALGPQLLLNWGVQIAKGMYYLEEHGMVHRNLAARNVLLKSPSQVQV
ADFGVADLLPPDDKQLLYSEAKTPIKWMALESIHFGKYTHQSDVWSYGVT
VWELMTFGAEPYAGLRLAEVPDLLEKGERLAQPQICTIDVYMVMVKCWMI
DENIRPTFKELANEFTRMARDPPRYLVIKRESGPGIAPGPEPHGLTNKKL
EEVELEPELDLDLDLEAEEDNLATTTLGSALSLPVGTLNRPRGSQSLLSP
SSGYMPMNQGNLGESCQESAVSGSSERCPRPVSLHPMPRGCLASESSEGH
VTGSEAELQEKVSMCRSRSRSRSPRPRGDSAYHSQRHSLLTPVTPLSPPG
LEEEDVNGYVMPDTHLKGTPSSREGTLSSVGLSSVLGTEEEDEDEEYEYM
NRRRRHSPPHPRPSSLEELGYEYMDVGSDLSASLGSTQSCPLHPVPIMP
TAGTTPDEDYEYMNRQRDGGGPGGDYAAMGACPASEQGYEEMRAFQGPGH
QAPHVHYARLKTLRSLEATDSAFDNPDYWHSRLFPKANAQRT
(SEQ ID NO: 246)

Rhesus monkey ERBB3 sequence
MRANGALQVLGLLFNLARGSEVGNSQAVCPGTLNGLSVTGDAENQYQTLY
KLYERCEVVMGNLEIVLTGHNADLSFLQWIREVTGYVLVAMNEFSTLPLP
NLRVVRGTQVYDGKFAIFVMLNYNTNSSHALRQLRLTQLTEILSGGVYIE
KNDKLCHMDTIDWKDIVRDQDAEIVVKDNGRSCPLCHEVCKGRCWGPGPE
DCQTLTKTICAPQCNGHCFGPNPNQCCHDECAGGCSGPQDTDCFACRHFN
DSGACVPRCPQPLVYNKLTFQLEPNPHTKYQYGGVCVASCPHNFVVDQTS
CVRACPPDKMEVDKNGLKMCEPCGGLCPKACEGTGSGSRFQTVDSSNIDG
FVNCTKILGNLDFLITGLNGDPWHKIPALDPEKLNVFRTVREITGYLNIQ
SWPPHMYNFSVFSNLTTIGGRSLYNRGFSLLIMKNLNVTSLGFRSLKEIS
AGRIYISANRQLCYHHSLNWTKVLRGPTEERLDIKHNRPRRDCVAEGKVC
DPLCSSGGCWGPGPGQCLSCRNYSRGGVCVTHCNFLNGEPREFAHEAECF
SCHPECQPMEGTATCNGSGSDTCAQCAHFRDGPHCVSSCPHGVLGAKGPI
YKYPDVQNECRPCHENCTQGCKGPELQDCLGQTLVLIGKTHLTMALTVIA
GLVVIFMMLGGTFLYWRGRRIQNKRAMRRYLERGESIEPLDPSEKANKVL
ARIFKETELRKLKVLGSGVFGTVHKGVWIPEGESIKIPVCIKIIEDKSGR
QSFQAVTDHMLAIGSLDHAHIVRLLGLCPGSSLQLVTQYLPLGSLLDHVR
QHRGALGPQLLLNWGVQIAKGMYYLEEHGMVHRNLAARNVLLKSPSQVQV
ADFGVADLLPPDDKQLLYSEAKTPIKWMALESIHFGKYTHQSDVWSYGVT
VWELMTFGAEPYAGLRLAEVPDLLEKGERLAQPQICTIDVYMVMVKCWMI
DENIRPTFKELANEFTRMARDPPRYLVIKRESGPGIAPGPEPHGLTNKKL
EEVELEPELDLDLDLEAEEDNLATTTLGSALSLPVGTLNRPRGSQSLLSP
SSGYMPMNQGNLGEACQESAVSGSSEWCPRPVSLHPMPRGCLASESSEGH
VTGSEAELQEKVSTCRSRSRSRSPRPRGDSAYHSQRHSLLTPVTPLSPPG
LEEEDVNGYVMPDTHLKGTPSSREGTLSSVGLSSVLGTEEEDEDEEYEYM
NRRRRHSPPRPPRPSSLEELGYEYMDVGSDLSASLGSTQSCPLHPVPVMP
TAGTTPDEDYEYMNRQRGGSGPGGDYAAMGACPASEQGYEEMRAFQGPGH
QAPHVHYAHLKTLRSLEATDSAFDNPDYWHSRLFPKANAQRT
(SEQ ID NO: 247)

The invention claimed is:

1. An anti-ERBB3 antibody or an antigen-binding portion thereof, wherein the antibody or antigen-binding portion thereof comprises a heavy chain variable (VH) region and a light chain variable (VL) region, wherein
   (a) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); and the VL region amino acid sequence comprises LCDR1 of RASQEISTYLS (SEQ ID NO: 261), LCDR2 of AASTLQS (SEQ ID NO:26) and LCDR3 of LQYDSSPLT (SEQ ID NO: 262); or
   (b) the VH region amino acid sequence comprises HCDR1 of GFTFSDYSMS (SEQ ID NO: 24), HCDR2 of VSTISDSGTYTYYPDSVKG (SEQ ID NO: 25) and HCDR3 of EWGDYDGFDF (SEQ ID NO: 15); and the VL region amino acid sequence comprises LCDR1 of RASQEISSYLS (SEQ ID NO: 21), LCDR2 of AASSLDT (SEQ ID NO: 263) and LCDR3 of amino acids 89-97 of SEQ ID NO: 224.

2. The antibody or antigen-binding portion of claim 1, wherein
   (a) the VH region amino acid sequence comprises SEQ ID NO:236 and the VL region amino acid sequence comprises SEQ ID NO:225; or
   (b) the VH region amino acid sequence comprises SEQ ID NO:235 and the VL region amino acid sequence comprises SEQ ID NO:224.

3. The antibody or antigen-binding portion of claim 1, the antibody is humanized or chimeric.

4. The antibody or antigen-binding portion of claim 1, wherein the VH region, the VL region, or both the VH and the VL region comprise one or more human framework region amino acid sequences.

5. The antibody or antigen-binding portion of claim 1, wherein the VH region, the VL region, or both the VH and the VL region comprise a human variable region framework scaffold amino acid sequence into which the CDRs have been inserted.

6. The antibody or antigen-binding portion of claim 1 wherein the VH region comprises an IGHV3-11 human germline scaffold amino acid sequence into which the HCDR1, HCDR2 and HCDR3 amino acid sequences have been inserted.

7. The antibody or antigen-binding portion of claim 1, wherein the VL region comprises an IGKV1-39 human germline scaffold amino acid sequence into which the LCDR1, LCDR2 and LCDR3 amino acid sequences have been inserted.

8. The antibody or antigen-binding portion of claim 1, wherein the antibody comprises an immunoglobulin constant region.

9. The antibody or antigen-binding portion of claim 8, wherein the immunoglobulin constant region is IgG, IgE, IgM, IgD, or IgA.

10. The antibody or antigen-binding portion of claim 9, wherein the immunoglobulin constant region is IgG1, IgG2, IgG3, IgG4, IgA1 or IgA2.

11. The antibody or antigen-binding portion of claim 8, wherein the immunoglobulin constant region is immunologically inert.

12. The antibody or antigen-binding portion of claim 8, wherein the immunoglobulin constant region is a wild-type human IgG4 constant region, a human IgG4 constant region comprising the amino acid substitution S228P, a wild-type human IgG1 constant region, a human IgG1 constant region comprising the amino acid substitutions L234A, L235A and G237A or a wild-type human IgG2 constant region, wherein numbering is according to the EU index as in Kabat.

13. The antibody or antigen-binding portion of claim 8, wherein the immunoglobulin constant region comprises any one of SEQ ID NOS:239-245.

14. The antigen-binding portion of claim 1, wherein the antigen-binding portion is an Fab, an Fab', an F(ab')2, an Fv, an scFv, a diabody, a triabody, a tetrabody, or a bis-scFv.

15. The antibody or antigen-binding portion of claim 1, wherein the antibody is monoclonal.

16. An immunoconjugate comprising the antibody or antigen-binding portion of claim 1 linked to a therapeutic agent.

17. The immunoconjugate of claim 16, wherein the therapeutic agent is a cytotoxin, a radioisotope, a chemotherapeutic agent, an immunomodulatory agent, an anti-angiogenic agent, an antiproliferative agent, or a therapeutic nucleic acid.

18. A pharmaceutical composition comprising the antibody or antigen-binding portion of claim 1, and a pharmaceutically acceptable carrier, diluent or excipient.

19. A pharmaceutical composition comprising the immunoconjugate of claim 16, and a pharmaceutically acceptable carrier, diluent or excipient.

* * * * *

SEQUENCE LISTING

<160> NUMBER OF SEQ ID NOS: 263

<210> SEQ ID NO 1
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1
<220> FEATURE:
<221> NAME/KEY: misc_feature
<222> LOCATION: (8)..(8)
<223> OTHER INFORMATION: Xaa is Gly or any other amino acid

<400> SEQUENCE: 1

Gly Phe Thr Phe Ser Asp Tyr Xaa Met Ser
1               5                   10

<210> SEQ ID NO 2
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2
<220> FEATURE:
<221> NAME/KEY: misc_feature
<222> LOCATION: (7)..(7)
<223> OTHER INFORMATION: Xaa is Gly or any other amino acid
<220> FEATURE:
<221> NAME/KEY: misc_feature
<222> LOCATION: (9)..(9)
<223> OTHER INFORMATION: Xaa is Thr or a conservative substitution of
      Thr
<220> FEATURE:
<221> NAME/KEY: misc_feature
<222> LOCATION: (10)..(10)
<223> OTHER INFORMATION: Xaa is Tyr or any other amino acid
<220> FEATURE:

```
<221> NAME/KEY: misc_feature
<222> LOCATION: (11)..(11)
<223> OTHER INFORMATION: Xaa is Thr or any other amino acid
<220> FEATURE:
<221> NAME/KEY: misc_feature
<222> LOCATION: (14)..(14)
<223> OTHER INFORMATION: Xaa is Pro or any other amino acid
<220> FEATURE:
<221> NAME/KEY: misc_feature
<222> LOCATION: (16)..(16)
<223> OTHER INFORMATION: Xaa is Asn or a conservative substitution of
      Asn

<400> SEQUENCE: 2

Val Ser Thr Ile Ser Asp Xaa Gly Xaa Xaa Xaa Tyr Tyr Xaa Asp Xaa
1               5                   10                  15

Val Lys Gly

<210> SEQ ID NO 3
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3
<220> FEATURE:
<221> NAME/KEY: misc_feature
<222> LOCATION: (1)..(1)
<223> OTHER INFORMATION: Xaa is Glu or any other amino acid
<220> FEATURE:
<221> NAME/KEY: misc_feature
<222> LOCATION: (2)..(2)
<223> OTHER INFORMATION: Xaa is Trp or any other amino acid
<220> FEATURE:
<221> NAME/KEY: misc_feature
<222> LOCATION: (5)..(5)
<223> OTHER INFORMATION: Xaa is Tyr or any other amino acid
<220> FEATURE:
<221> NAME/KEY: misc_feature
<222> LOCATION: (8)..(8)
<223> OTHER INFORMATION: Xaa is Phe or any other amino acid
<220> FEATURE:
<221> NAME/KEY: misc_feature
<222> LOCATION: (10)..(10)
<223> OTHER INFORMATION: Xaa is Tyr or any other amino acid

<400> SEQUENCE: 3

Xaa Xaa Gly Asp Xaa Asp Gly Xaa Asp Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: 24C05 murine/humanized antibody HCDR1

<400> SEQUENCE: 4

Gly Phe Thr Phe Ser Asp Tyr Ala Met Ser
1               5                   10

<210> SEQ ID NO 5
<211> LENGTH: 19
<212> TYPE: PRT
<213> ORGANISM: Artificial Sequence
<220> FEATURE:
<223> OTHER INFORMATION: 24C05 murine/humanized antibody HCDR2

<400> SEQUENCE: 5

Val Ser Thr Ile Ser Asp Gly Gly Thr Tyr Thr Tyr Tyr Pro Asp Asn
1               5                   10                  15
```

Val Lys Gly

<210> SEQ ID NO 6
<211> LENGTH: 10
<212> TYPE: PRT
<213> ORGANISM: Artificial Sequence
<220> FEATURE:
<223> OTHER INFORMATION: 24C05 murine/humanized antibody HCDR3

<400> SEQUENCE: 6

Glu Trp Gly Asp Tyr Asp Gly Phe Asp Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1
<220> FEATURE:
<221> NAME/KEY: misc_feature
<222> LOCATION: (5)..(5)
<223> OTHER INFORMATION: Xaa is Glu or any other amino acid
<220> FEATURE:
<221> NAME/KEY: misc_feature
<222> LOCATION: (8)..(8)
<223> OTHER INFORMATION: Xaa is Gly or a conservative substitution of
      Gly
<220> FEATURE:
<221> NAME/KEY: misc_feature
<222> LOCATION: (11)..(11)
<223> OTHER INFORMATION: Xaa is Ser or a conservative substitution of
      Ser

<400> SEQUENCE: 7

Arg Ala Ser Gln Xaa Ile Ser Xaa Tyr Leu Xaa
1               5                   10

<210> SEQ ID NO 8
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2
<220> FEATURE:
<221> NAME/KEY: misc_feature
<222> LOCATION: (1)..(1)
<223> OTHER INFORMATION: Xaa is Ala or any other amino acid
<220> FEATURE:
<221> NAME/KEY: misc_feature
<222> LOCATION: (4)..(4)
<223> OTHER INFORMATION: Xaa is Thr or a conservative substitution of
      Thr
<220> FEATURE:
<221> NAME/KEY: misc_feature
<222> LOCATION: (6)..(6)
<223> OTHER INFORMATION: Xaa is Asp any other amino acid

<400> SEQUENCE: 8

Xaa Ala Ser Xaa Leu Xaa Ser
1               5

<210> SEQ ID NO 9
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

```
<220> FEATURE:
<221> NAME/KEY: misc_feature
<222> LOCATION: (1)..(1)
<223> OTHER INFORMATION: Xaa is Leu or any other amino acid
<220> FEATURE:
<221> NAME/KEY: misc_feature
<222> LOCATION: (3)..(3)
<223> OTHER INFORMATION: Xaa is Tyr or any other amino acid
<220> FEATURE:
<221> NAME/KEY: misc_feature
<222> LOCATION: (4)..(4)
<223> OTHER INFORMATION: Xaa is Asp or any other amino acid
<220> FEATURE:
<221> NAME/KEY: misc_feature
<222> LOCATION: (6)..(6)
<223> OTHER INFORMATION: Xaa is Tyr or any other amino acid
<220> FEATURE:
<221> NAME/KEY: misc_feature
<222> LOCATION: (7)..(7)
<223> OTHER INFORMATION: Xaa is Pro or any other amino acid
<220> FEATURE:
<221> NAME/KEY: misc_feature
<222> LOCATION: (8)..(8)
<223> OTHER INFORMATION: Xaa is Tyr or any other amino acid

<400> SEQUENCE: 9

Xaa Gln Xaa Xaa Ser Xaa Xaa Xaa Thr
1               5

<210> SEQ ID NO 10
<211> LENGTH: 11
<212> TYPE: PRT
<213> ORGANISM: Artificial Sequence
<220> FEATURE:
<223> OTHER INFORMATION: 24C05 murine/humanized antibody LCDR1

<400> SEQUENCE: 10

Arg Ala Ser Gln Glu Ile Ser Gly Tyr Leu Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: 24C05 murine/humanized antibody LCDR2

<400> SEQUENCE: 11

Ala Ala Ser Thr Leu Asp Ser
1               5

<210> SEQ ID NO 12
<211> LENGTH: 9
<212> TYPE: PRT
<213> ORGANISM: Artificial Sequence
<220> FEATURE:
<223> OTHER INFORMATION: 24C05 murine/humanized antibody LCDR3

<400> SEQUENCE: 12

Leu Gln Tyr Asp Ser Tyr Pro Tyr Thr
1               5

<210> SEQ ID NO 13
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 13
```

```
Gly Phe Thr Phe Ser Asp Tyr Gly Met Ser
1               5                   10

<210> SEQ ID NO 14
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 14

Val Ser Thr Ile Ser Asp Ser Gly Ser Tyr Ile Tyr Tyr Ala Asp Ser
1               5                   10                  15

Val Lys Gly

<210> SEQ ID NO 15
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 15

Glu Trp Gly Asp Tyr Asp Gly Phe Asp Phe
1               5                   10

<210> SEQ ID NO 16
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 16

Arg Ala Ser Gln Ser Ile Ser Ser Tyr Leu Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 17

Ala Ala Ser Ser Leu Gln Ser
1               5

<210> SEQ ID NO 18
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 18

Leu Gln Tyr Asp Ser Thr Pro Leu Thr
1               5

<210> SEQ ID NO 19
<211> LENGTH: 19
```

```
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 19

Val Ser Thr Ile Ser Asp Ser Gly Ser Tyr Thr Tyr Tyr Pro Asp Ser
1               5                   10                  15

Val Lys Gly

<210> SEQ ID NO 20
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 20

Glu Leu Gly Asp Tyr Asp Gly Phe Asp Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 21

Arg Ala Ser Gln Glu Ile Ser Ser Tyr Leu Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 22

Ala Ala Ser Ser Leu Asp Ser
1               5

<210> SEQ ID NO 23
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 23

Leu Gln Tyr Asp Ser Thr Pro Tyr Thr
1               5

<210> SEQ ID NO 24
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 24
```

Gly Phe Thr Phe Ser Asp Tyr Ser Met Ser
1               5                   10

<210> SEQ ID NO 25
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 25

Val Ser Thr Ile Ser Asp Ser Gly Thr Tyr Thr Tyr Tyr Pro Asp Ser
1               5                   10                  15

Val Lys Gly

<210> SEQ ID NO 26
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 26

Ala Ala Ser Thr Leu Gln Ser
1               5

<210> SEQ ID NO 27
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 27

Glu Trp Gly Asp Tyr Asp Gly Phe Asp His
1               5                   10

<210> SEQ ID NO 28
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 28

Val Ser Thr Ile Ser Asp Gly Gly Ser Tyr Thr Tyr Tyr Ala Asp Ser
1               5                   10                  15

Val Lys Gly

<210> SEQ ID NO 29
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 29

Glu Trp Gly Asp Tyr Asp Gly Phe Asp Glu
1               5                   10

```
<210> SEQ ID NO 30
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 30

Arg Ala Ser Gln Ser Ile Ser Gly Tyr Leu Ser
1               5                   10

<210> SEQ ID NO 31
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 31

Val Ser Thr Ile Ser Asp Gly Gly Ser Tyr Thr Tyr Tyr Ala Asp Asn
1               5                   10                  15

Val Lys Gly

<210> SEQ ID NO 32
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion consensus
      LCDR1

<400> SEQUENCE: 32

Arg Ala Ser Gln Glu Ile Ser Gly Tyr Leu Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion consensus
      LCDR2

<400> SEQUENCE: 33

Ala Ala Ser Thr Leu Asp Ser
1               5

<210> SEQ ID NO 34
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion consensus
      LCDR3

<400> SEQUENCE: 34

Leu Gln Tyr Asp Ser Tyr Pro Tyr Thr
1               5

<210> SEQ ID NO 35
<211> LENGTH: 10
<212> TYPE: PRT
<213> ORGANISM: Artificial Sequence
```

```
<220> FEATURE:
<223> OTHER INFORMATION: anti-ERBB3 antibody molecule or antigen-binding
      portion consensus
      HCDR1

<400> SEQUENCE: 35

Gly Phe Thr Phe Ser Asp Tyr Ala Met Ser
1               5                   10

<210> SEQ ID NO 36
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion consensus
      HCDR2

<400> SEQUENCE: 36

Val Ser Thr Ile Ser Asp Gly Gly Thr Tyr Thr Tyr Tyr Pro Asp Asn
1               5                   10                  15

Val Lys Gly

<210> SEQ ID NO 37
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion consensus
      HCDR3

<400> SEQUENCE: 37

Glu Trp Gly Asp Tyr Asp Gly Phe Asp Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1
<220> FEATURE:
<221> NAME/KEY: misc_feature
<222> LOCATION: (8)..(8)
<223> OTHER INFORMATION: Xaa is Glu, Gly, His, Asn, Arg, Ser, Thr, Gln
      or Val

<400> SEQUENCE: 38

Gly Phe Thr Phe Ser Asp Tyr Xaa Met Ser
1               5                   10

<210> SEQ ID NO 39
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2
<220> FEATURE:
<221> NAME/KEY: misc_feature
<222> LOCATION: (7)..(7)
<223> OTHER INFORMATION: Xaa is Gly, Ser or Asp
<220> FEATURE:
<221> NAME/KEY: misc_feature
<222> LOCATION: (9)..(9)
<223> OTHER INFORMATION: Xaa is Thr or Ser
<220> FEATURE:
<221> NAME/KEY: misc_feature
```

```
<222> LOCATION: (10)..(10)
<223> OTHER INFORMATION: Xaa is Tyr or Thr
<220> FEATURE:
<221> NAME/KEY: misc_feature
<222> LOCATION: (11)..(11)
<223> OTHER INFORMATION: Xaa is Thr or Ile
<220> FEATURE:
<221> NAME/KEY: misc_feature
<222> LOCATION: (14)..(14)
<223> OTHER INFORMATION: Xaa is Pro or Ala
<220> FEATURE:
<221> NAME/KEY: misc_feature
<222> LOCATION: (16)..(16)
<223> OTHER INFORMATION: Xaa is Asn or Ser

<400> SEQUENCE: 39

Val Ser Thr Ile Ser Asp Xaa Gly Xaa Xaa Xaa Tyr Tyr Xaa Asp Xaa
1               5                   10                  15

Val Lys Gly

<210> SEQ ID NO 40
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3
<220> FEATURE:
<221> NAME/KEY: misc_feature
<222> LOCATION: (1)..(1)
<223> OTHER INFORMATION: Xaa is Glu or Met
<220> FEATURE:
<221> NAME/KEY: misc_feature
<222> LOCATION: (2)..(2)
<223> OTHER INFORMATION: Xaa is Trp, Phe, Leu, Met, Gln or Tyr
<220> FEATURE:
<221> NAME/KEY: misc_feature
<222> LOCATION: (5)..(5)
<223> OTHER INFORMATION: Xaa is Tyr, Ala, Asp, Glu, His, Leu, Met, Asn,
      Gln, Ser, Thr or
      Trp
<220> FEATURE:
<221> NAME/KEY: misc_feature
<222> LOCATION: (8)..(8)
<223> OTHER INFORMATION: Xaa is Phe, Ile, Leu, Trp or Tyr
<220> FEATURE:
<221> NAME/KEY: misc_feature
<222> LOCATION: (10)..(10)
<223> OTHER INFORMATION: Xaa is Tyr, Ala, Asp, Glu, Phe, His, Ile, Lys,
      Leu, Met, Asn,
      Gln, Arg, Ser, Val or Trp

<400> SEQUENCE: 40

Xaa Xaa Gly Asp Xaa Asp Gly Xaa Asp Xaa
1               5                   10

<210> SEQ ID NO 41
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1
<220> FEATURE:
<221> NAME/KEY: misc_feature
<222> LOCATION: (8)..(8)
<223> OTHER INFORMATION: Xaa is Gly or Ser

<400> SEQUENCE: 41

Gly Phe Thr Phe Ser Asp Tyr Xaa Met Ser
1               5                   10
```

```
<210> SEQ ID NO 42
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2
<220> FEATURE:
<221> NAME/KEY: misc_feature
<222> LOCATION: (7)..(7)
<223> OTHER INFORMATION: Xaa is Gly or Ser
<220> FEATURE:
<221> NAME/KEY: misc_feature
<222> LOCATION: (10)..(10)
<223> OTHER INFORMATION: Xaa is Tyr or Thr
<220> FEATURE:
<221> NAME/KEY: misc_feature
<222> LOCATION: (11)..(11)
<223> OTHER INFORMATION: Xaa is Thr or Ile
<220> FEATURE:
<221> NAME/KEY: misc_feature
<222> LOCATION: (14)..(14)
<223> OTHER INFORMATION: Xaa is Pro or Ala

<400> SEQUENCE: 42

Val Ser Thr Ile Ser Asp Xaa Gly Ser Xaa Xaa Tyr Tyr Xaa Asp Ser
1               5                   10                  15

Val Lys Gly

<210> SEQ ID NO 43
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3
<220> FEATURE:
<221> NAME/KEY: misc_feature
<222> LOCATION: (2)..(2)
<223> OTHER INFORMATION: Xaa is Trp, Leu or Tyr
<220> FEATURE:
<221> NAME/KEY: misc_feature
<222> LOCATION: (10)..(10)
<223> OTHER INFORMATION: Xaa is Tyr, Glu, Phe, His or Asn

<400> SEQUENCE: 43

Glu Xaa Gly Asp Tyr Asp Gly Phe Asp Xaa
1               5                   10

<210> SEQ ID NO 44
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1
<220> FEATURE:
<221> NAME/KEY: misc_feature
<222> LOCATION: (5)..(5)
<223> OTHER INFORMATION: Xaa is Glu, Ser, Ile or Asn
<220> FEATURE:
<221> NAME/KEY: misc_feature
<222> LOCATION: (8)..(8)
<223> OTHER INFORMATION: Xaa is Gly or Ser
<220> FEATURE:
<221> NAME/KEY: misc_feature
<222> LOCATION: (11)..(11)
<223> OTHER INFORMATION: Xaa is Ser or Asn

<400> SEQUENCE: 44

Arg Ala Ser Gln Xaa Ile Ser Xaa Tyr Leu Xaa
1               5                   10
```

```
<210> SEQ ID NO 45
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2
<220> FEATURE:
<221> NAME/KEY: misc_feature
<222> LOCATION: (1)..(1)
<223> OTHER INFORMATION: Xaa is Ala or Glu
<220> FEATURE:
<221> NAME/KEY: misc_feature
<222> LOCATION: (4)..(4)
<223> OTHER INFORMATION: Xaa is Thr, Ser or Asn
<220> FEATURE:
<221> NAME/KEY: misc_feature
<222> LOCATION: (6)..(6)
<223> OTHER INFORMATION: Xaa is Asp, His, Lys or Gln

<400> SEQUENCE: 45

Xaa Ala Ser Xaa Leu Xaa Ser
1               5

<210> SEQ ID NO 46
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3
<220> FEATURE:
<221> NAME/KEY: misc_feature
<222> LOCATION: (1)..(1)
<223> OTHER INFORMATION: Xaa is Leu or Gln
<220> FEATURE:
<221> NAME/KEY: misc_feature
<222> LOCATION: (3)..(3)
<223> OTHER INFORMATION: Xaa is Tyr or Ser
<220> FEATURE:
<221> NAME/KEY: misc_feature
<222> LOCATION: (4)..(4)
<223> OTHER INFORMATION: Xaa is Asp or Tyr
<220> FEATURE:
<221> NAME/KEY: misc_feature
<222> LOCATION: (6)..(6)
<223> OTHER INFORMATION: Xaa is Tyr or Thr
<220> FEATURE:
<221> NAME/KEY: misc_feature
<222> LOCATION: (7)..(7)
<223> OTHER INFORMATION: Xaa is Pro or His
<220> FEATURE:
<221> NAME/KEY: misc_feature
<222> LOCATION: (8)..(8)
<223> OTHER INFORMATION: Xaa is Tyr or Leu

<400> SEQUENCE: 46

Xaa Gln Xaa Xaa Ser Xaa Xaa Xaa Thr
1               5

<210> SEQ ID NO 47
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1
<220> FEATURE:
<221> NAME/KEY: misc_feature
<222> LOCATION: (5)..(5)
<223> OTHER INFORMATION: Xaa is Glu or Ser
<220> FEATURE:
<221> NAME/KEY: misc_feature
<222> LOCATION: (8)..(8)
```

<223> OTHER INFORMATION: Xaa is Gly or Ser
<220> FEATURE:
<221> NAME/KEY: misc_feature
<222> LOCATION: (11)..(11)
<223> OTHER INFORMATION: Xaa is Ser or Asn

<400> SEQUENCE: 47

Arg Ala Ser Gln Xaa Ile Ser Xaa Tyr Leu Xaa
1               5                   10

<210> SEQ ID NO 48
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2
<220> FEATURE:
<221> NAME/KEY: misc_feature
<222> LOCATION: (4)..(4)
<223> OTHER INFORMATION: Xaa is Thr or Ser
<220> FEATURE:
<221> NAME/KEY: misc_feature
<222> LOCATION: (6)..(6)
<223> OTHER INFORMATION: Xaa is Asp or Gln

<400> SEQUENCE: 48

Ala Ala Ser Xaa Leu Xaa Ser
1               5

<210> SEQ ID NO 49
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3
<220> FEATURE:
<221> NAME/KEY: misc_feature
<222> LOCATION: (4)..(4)
<223> OTHER INFORMATION: Xaa is Asp or Tyr
<220> FEATURE:
<221> NAME/KEY: misc_feature
<222> LOCATION: (8)..(8)
<223> OTHER INFORMATION: Xaa is Tyr or Leu

<400> SEQUENCE: 49

Leu Gln Tyr Xaa Ser Thr Pro Xaa Thr
1               5

<210> SEQ ID NO 50
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 50

Arg Ala Ser Gln Ser Ile Ser Ser Tyr Leu Asn
1               5                   10

<210> SEQ ID NO 51
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 51

```
Glu Tyr Gly Asp Tyr Asp Gly Phe Asp Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 52

Arg Ala Ser Gln Ile Ile Ser Ser Tyr Leu Ser
1               5                   10

<210> SEQ ID NO 53
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 53

Leu Gln Tyr Tyr Ser Thr Pro Leu Thr
1               5

<210> SEQ ID NO 54
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 54

Val Ser Thr Ile Ser Asp Ser Gly Ser Tyr Thr Tyr Tyr Ala Asp Ser
1               5                   10                  15

Val Lys Gly

<210> SEQ ID NO 55
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 55

Glu Trp Gly Asp Tyr Asp Gly Phe Asp Asn
1               5                   10

<210> SEQ ID NO 56
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 56

Val Ser Thr Ile Ser Asp Ser Gly Thr Thr Ile Tyr Tyr Ala Asp Asn
1               5                   10                  15

Val Lys Gly
```

```
<210> SEQ ID NO 57
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 57

Val Ser Thr Ile Ser Asp Gly Gly Ser Tyr Thr Tyr Tyr Pro Asp Ser
1               5                   10                  15

Val Lys Gly

<210> SEQ ID NO 58
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 58

Val Ser Thr Ile Ser Asp Ser Gly Ser Thr Ile Tyr Tyr Ala Asp Ser
1               5                   10                  15

Val Lys Gly

<210> SEQ ID NO 59
<211> LENGTH: 10
<212> TYPE: PRT
<213> ORGANISM: Mus musculus

<400> SEQUENCE: 59

Gly Phe Thr Phe Ser Asp Tyr Ala Met Ser
1               5                   10

<210> SEQ ID NO 60
<211> LENGTH: 5
<212> TYPE: PRT
<213> ORGANISM: Mus musculus

<400> SEQUENCE: 60

Asp Tyr Ala Met Ser
1               5

<210> SEQ ID NO 61
<211> LENGTH: 7
<212> TYPE: PRT
<213> ORGANISM: Mus musculus

<400> SEQUENCE: 61

Gly Phe Thr Phe Ser Asp Tyr
1               5

<210> SEQ ID NO 62
<211> LENGTH: 8
<212> TYPE: PRT
<213> ORGANISM: Mus musculus

<400> SEQUENCE: 62

Gly Phe Thr Phe Ser Asp Tyr Ala
1               5

<210> SEQ ID NO 63
<211> LENGTH: 12
<212> TYPE: PRT
```

<213> ORGANISM: Mus musculus

<400> SEQUENCE: 63

```
Ala Ser Gly Phe Thr Phe Ser Asp Tyr Ala Met Ser
1               5                   10
```

<210> SEQ ID NO 64
<211> LENGTH: 6
<212> TYPE: PRT
<213> ORGANISM: Mus musculus

<400> SEQUENCE: 64

```
Ser Asp Tyr Ala Met Ser
1               5
```

<210> SEQ ID NO 65
<211> LENGTH: 19
<212> TYPE: PRT
<213> ORGANISM: Mus musculus

<400> SEQUENCE: 65

```
Val Ser Thr Ile Ser Asp Gly Gly Thr Tyr Thr Tyr Tyr Pro Asp Asn
1               5                   10                  15

Val Lys Gly
```

<210> SEQ ID NO 66
<211> LENGTH: 17
<212> TYPE: PRT
<213> ORGANISM: Mus musculus

<400> SEQUENCE: 66

```
Thr Ile Ser Asp Gly Gly Thr Tyr Thr Tyr Tyr Pro Asp Asn Val Lys
1               5                   10                  15

Gly
```

<210> SEQ ID NO 67
<211> LENGTH: 6
<212> TYPE: PRT
<213> ORGANISM: Mus musculus

<400> SEQUENCE: 67

```
Ser Asp Gly Gly Thr Tyr
1               5
```

<210> SEQ ID NO 68
<211> LENGTH: 8
<212> TYPE: PRT
<213> ORGANISM: Mus musculus

<400> SEQUENCE: 68

```
Ile Ser Asp Gly Gly Thr Tyr Thr
1               5
```

<210> SEQ ID NO 69
<211> LENGTH: 16
<212> TYPE: PRT
<213> ORGANISM: Mus musculus

<400> SEQUENCE: 69

```
Ile Ser Asp Gly Gly Thr Tyr Thr Tyr Tyr Pro Asp Asn Val Lys Gly
1               5                   10                  15
```

<210> SEQ ID NO 70

<211> LENGTH: 10
<212> TYPE: PRT
<213> ORGANISM: Mus musculus

<400> SEQUENCE: 70

Thr Ile Ser Asp Gly Gly Thr Tyr Thr Tyr
1               5                   10

<210> SEQ ID NO 71
<211> LENGTH: 12
<212> TYPE: PRT
<213> ORGANISM: Mus musculus

<400> SEQUENCE: 71

Val Ser Thr Ile Ser Asp Gly Gly Thr Tyr Thr Tyr
1               5                   10

<210> SEQ ID NO 72
<211> LENGTH: 10
<212> TYPE: PRT
<213> ORGANISM: Mus musculus

<400> SEQUENCE: 72

Glu Trp Gly Asp Tyr Asp Gly Phe Asp Tyr
1               5                   10

<210> SEQ ID NO 73
<211> LENGTH: 12
<212> TYPE: PRT
<213> ORGANISM: Mus musculus

<400> SEQUENCE: 73

Ala Arg Glu Trp Gly Asp Tyr Asp Gly Phe Asp Tyr
1               5                   10

<210> SEQ ID NO 74
<211> LENGTH: 9
<212> TYPE: PRT
<213> ORGANISM: Mus musculus

<400> SEQUENCE: 74

Glu Trp Gly Asp Tyr Asp Gly Phe Asp
1               5

<210> SEQ ID NO 75
<211> LENGTH: 11
<212> TYPE: PRT
<213> ORGANISM: Mus musculus

<400> SEQUENCE: 75

Ala Arg Glu Trp Gly Asp Tyr Asp Gly Phe Asp
1               5                   10

<210> SEQ ID NO 76
<211> LENGTH: 11
<212> TYPE: PRT
<213> ORGANISM: Mus musculus

<400> SEQUENCE: 76

Arg Ala Ser Gln Glu Ile Ser Gly Tyr Leu Ser
1               5                   10

<210> SEQ ID NO 77
<211> LENGTH: 6
<212> TYPE: PRT

<213> ORGANISM: Mus musculus

<400> SEQUENCE: 77

Gln Glu Ile Ser Gly Tyr
1               5

<210> SEQ ID NO 78
<211> LENGTH: 8
<212> TYPE: PRT
<213> ORGANISM: Mus musculus

<400> SEQUENCE: 78

Ala Ser Gln Glu Ile Ser Gly Tyr
1               5

<210> SEQ ID NO 79
<211> LENGTH: 8
<212> TYPE: PRT
<213> ORGANISM: Mus musculus

<400> SEQUENCE: 79

Ile Ser Gly Tyr Leu Ser Trp Tyr
1               5

<210> SEQ ID NO 80
<211> LENGTH: 7
<212> TYPE: PRT
<213> ORGANISM: Mus musculus

<400> SEQUENCE: 80

Ala Ala Ser Thr Leu Asp Ser
1               5

<210> SEQ ID NO 81
<211> LENGTH: 10
<212> TYPE: PRT
<213> ORGANISM: Mus musculus

<400> SEQUENCE: 81

Leu Leu Ile Tyr Ala Ala Ser Thr Leu Asp
1               5                   10

<210> SEQ ID NO 82
<211> LENGTH: 9
<212> TYPE: PRT
<213> ORGANISM: Mus musculus

<400> SEQUENCE: 82

Leu Gln Tyr Asp Ser Tyr Pro Tyr Thr
1               5

<210> SEQ ID NO 83
<211> LENGTH: 6
<212> TYPE: PRT
<213> ORGANISM: Mus musculus

<400> SEQUENCE: 83

Tyr Asp Ser Tyr Pro Tyr
1               5

<210> SEQ ID NO 84
<211> LENGTH: 8
<212> TYPE: PRT
<213> ORGANISM: Mus musculus

<400> SEQUENCE: 84

Leu Gln Tyr Asp Ser Tyr Pro Tyr
1               5

<210> SEQ ID NO 85
<211> LENGTH: 119
<212> TYPE: PRT
<213> ORGANISM: Artificial Sequence
<220> FEATURE:
<223> OTHER INFORMATION: h24C05-VH IGHV3-11

<400> SEQUENCE: 85

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115

<210> SEQ ID NO 86
<211> LENGTH: 119
<212> TYPE: PRT
<213> ORGANISM: Artificial Sequence
<220> FEATURE:
<223> OTHER INFORMATION: VH graft IGHV3-11

<400> SEQUENCE: 86

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Thr Ile Ser Asp Gly Gly Thr Tyr Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Tyr Trp Gly Gln Gly
            100                 105                 110

Thr Leu Val Thr Val Ser Ser
        115

<210> SEQ ID NO 87
<211> LENGTH: 107
<212> TYPE: PRT
<213> ORGANISM: Artificial Sequence
<220> FEATURE:

<223> OTHER INFORMATION: h24C05-VL IGKV1-16

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Phe Gln Gln Lys Pro Gly Lys Ala Pro Lys Ser Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gly Gly Thr Lys Val Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: VL graft IGKV1-39

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Gly Tyr
            20                  25                  30

Leu Ser Trp Tyr Gln Gln Lys Pro Gly Lys Ala Pro Lys Leu Leu Ile
        35                  40                  45

Tyr Ala Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Tyr Pro Tyr
                85                  90                  95

Thr Phe Gly Gly Gly Thr Lys Val Glu Ile Lys
            100                 105

<210> SEQ ID NO 89
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 89

Arg Ala Ser Gln Ser Ile Ser Gly Tyr Leu Asn
1               5                   10

<210> SEQ ID NO 90
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

```
<400> SEQUENCE: 90

Arg Ala Ser Gln Glu Ile Ser Ser Tyr Leu Asn
1               5                   10

<210> SEQ ID NO 91
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 91

Arg Ala Ser Gln Glu Ile Ser Gly Tyr Leu Asn
1               5                   10

<210> SEQ ID NO 92
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 92

Arg Ala Ser Gln Asn Ile Ser Ser Tyr Leu Ser
1               5                   10

<210> SEQ ID NO 93
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 93

Ala Ala Ser Asn Leu Gln Ser
1               5

<210> SEQ ID NO 94
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 94

Ala Ala Ser Ser Leu His Ser
1               5

<210> SEQ ID NO 95
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 95

Glu Ala Ser Ser Leu Asp Ser
1               5

<210> SEQ ID NO 96
<211> LENGTH: 7
<212> TYPE: PRT
```

```
<213> ORGANISM: Artificial Sequence
<220> FEATURE:
<223> OTHER INFORMATION: anti-ERBB3 antibody molecule or antigen-binding
      portion LCDR2

<400> SEQUENCE: 96

Ala Ala Ser Ser Leu Lys Ser
1               5

<210> SEQ ID NO 97
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 97

Glu Ala Ser Ser Leu Gln Ser
1               5

<210> SEQ ID NO 98
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 98

Leu Gln Tyr Tyr Ser Tyr Pro Tyr Thr
1               5

<210> SEQ ID NO 99
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 99

Gln Gln Tyr Asp Ser Tyr Pro Tyr Thr
1               5

<210> SEQ ID NO 100
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 100

Leu Gln Tyr Asp Ser Tyr Pro Leu Thr
1               5

<210> SEQ ID NO 101
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 101

Gln Gln Tyr Asp Ser Thr Pro Tyr Thr
1               5
```

<210> SEQ ID NO 102
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 102

Leu Gln Ser Asp Ser Thr Pro Tyr Thr
1               5

<210> SEQ ID NO 103
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 103

Leu Gln Ser Asp Ser Thr Pro Leu Thr
1               5

<210> SEQ ID NO 104
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 104

Gln Gln Tyr Asp Ser Tyr Pro Leu Thr
1               5

<210> SEQ ID NO 105
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 105

Leu Gln Tyr Tyr Ser Tyr Pro Leu Thr
1               5

<210> SEQ ID NO 106
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 106

Leu Gln Tyr Tyr Ser Thr Pro Tyr Thr
1               5

<210> SEQ ID NO 107
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

-continued

```
<400> SEQUENCE: 107

Gln Gln Tyr Asp Ser Thr Pro Leu Thr
1               5

<210> SEQ ID NO 108
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 108

Leu Gln Tyr Asp Ser Tyr His Leu Thr
1               5

<210> SEQ ID NO 109
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 109

Gly Phe Thr Phe Ser Asp Tyr Ala Met Ser
1               5                   10

<210> SEQ ID NO 110
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 110

Gly Phe Thr Phe Ser Asp Tyr Glu Met Ser
1               5                   10

<210> SEQ ID NO 111
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 111

Gly Phe Thr Phe Ser Asp Tyr His Met Ser
1               5                   10

<210> SEQ ID NO 112
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 112

Gly Phe Thr Phe Ser Asp Tyr Asn Met Ser
1               5                   10

<210> SEQ ID NO 113
<211> LENGTH: 10
```

-continued

```
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 113

Gly Phe Thr Phe Ser Asp Tyr Gln Met Ser
1               5                   10

<210> SEQ ID NO 114
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 114

Gly Phe Thr Phe Ser Asp Tyr Arg Met Ser
1               5                   10

<210> SEQ ID NO 115
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 115

Gly Phe Thr Phe Ser Asp Tyr Thr Met Ser
1               5                   10

<210> SEQ ID NO 116
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR1

<400> SEQUENCE: 116

Gly Phe Thr Phe Ser Asp Tyr Val Met Ser
1               5                   10

<210> SEQ ID NO 117
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 117

Val Gly Thr Ile Ser Asp Gly Gly Thr Thr Ile Tyr Tyr Ala Asp Asn
1               5                   10                  15

Val Lys Gly

<210> SEQ ID NO 118
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 118
```

Val Ser Thr Ile Ser Asp Asp Gly Ser Thr Thr Tyr Tyr Ala Asp Ser
1               5                   10                  15

Val Lys Gly

<210> SEQ ID NO 119
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 119

Val Ser Thr Ile Ser Asp Gly Gly Ser Thr Ile Tyr Tyr Ala Asp Asn
1               5                   10                  15

Val Lys Gly

<210> SEQ ID NO 120
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 120

Val Ser Thr Ile Ser Asp Gly Gly Ser Thr Ile Tyr Tyr Ala Asp Ser
1               5                   10                  15

Val Lys Gly

<210> SEQ ID NO 121
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 121

Val Ser Thr Ile Ser Asp Gly Gly Ser Thr Ile Tyr Tyr Pro Asp Asn
1               5                   10                  15

Val Lys Gly

<210> SEQ ID NO 122
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 122

Val Ser Thr Ile Ser Asp Gly Gly Ser Thr Ile Tyr Tyr Pro Asp Ser
1               5                   10                  15

Val Lys Gly

<210> SEQ ID NO 123
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 123

Val Ser Thr Ile Ser Asp Gly Gly Ser Thr Thr Tyr Tyr Ala Asp Asn
1               5                   10                  15

Val Lys Gly

<210> SEQ ID NO 124
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 124

Val Ser Thr Ile Ser Asp Gly Gly Ser Thr Thr Tyr Tyr Ala Asp Ser
1               5                   10                  15

Val Lys Gly

<210> SEQ ID NO 125
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 125

Val Ser Thr Ile Ser Asp Gly Gly Ser Thr Thr Tyr Tyr Pro Asp Asn
1               5                   10                  15

Val Lys Gly

<210> SEQ ID NO 126
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 126

Val Ser Thr Ile Ser Asp Gly Gly Ser Thr Thr Tyr Tyr Pro Asp Ser
1               5                   10                  15

Val Lys Gly

<210> SEQ ID NO 127
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 127

Val Ser Thr Ile Ser Asp Gly Gly Ser Tyr Ile Tyr Tyr Ala Asp Asn
1               5                   10                  15

Val Lys Gly

<210> SEQ ID NO 128
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 128

Val Ser Thr Ile Ser Asp Gly Gly Ser Tyr Ile Tyr Tyr Ala Asp Ser
1               5                   10                  15

Val Lys Gly

<210> SEQ ID NO 129
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 129

Val Ser Thr Ile Ser Asp Gly Gly Ser Tyr Ile Tyr Tyr Pro Asp Asn
1               5                   10                  15

Val Lys Gly

<210> SEQ ID NO 130
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 130

Val Ser Thr Ile Ser Asp Gly Gly Ser Tyr Ile Tyr Tyr Pro Asp Ser
1               5                   10                  15

Val Lys Gly

<210> SEQ ID NO 131
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 131

Val Ser Thr Ile Ser Asp Gly Gly Ser Tyr Thr Tyr Tyr Pro Asp Asn
1               5                   10                  15

Val Lys Gly

<210> SEQ ID NO 132
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 132

Val Ser Thr Ile Ser Asp Gly Gly Thr Thr Ile Tyr Tyr Ala Asp Asn
1               5                   10                  15

Val Lys Gly

<210> SEQ ID NO 133
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding portion HCDR2

<400> SEQUENCE: 133

Val Ser Thr Ile Ser Asp Gly Gly Thr Thr Ile Tyr Tyr Ala Asp Ser
1               5                   10                  15

Val Lys Gly

<210> SEQ ID NO 134
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 134

Val Ser Thr Ile Ser Asp Gly Gly Thr Thr Ile Tyr Tyr Pro Asp Ser
1               5                   10                  15

Val Lys Gly

<210> SEQ ID NO 135
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 135

Val Ser Thr Ile Ser Asp Gly Gly Thr Thr Tyr Tyr Ala Asp Asn
1               5                   10                  15

Val Lys Gly

<210> SEQ ID NO 136
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 136

Val Ser Thr Ile Ser Asp Gly Gly Thr Thr Tyr Tyr Ala Asp Ser
1               5                   10                  15

Val Lys Gly

<210> SEQ ID NO 137
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 137

Val Ser Thr Ile Ser Asp Gly Gly Thr Thr Tyr Tyr Pro Asp Asn
1               5                   10                  15

Val Lys Gly

<210> SEQ ID NO 138
<211> LENGTH: 19
<212> TYPE: PRT
<213> ORGANISM: Artificial Sequence
<220> FEATURE:

```
<223> OTHER INFORMATION: anti-ERBB3 antibody molecule or antigen-binding
      portion HCDR2

<400> SEQUENCE: 138

Val Ser Thr Ile Ser Asp Gly Gly Thr Thr Thr Tyr Tyr Pro Asp Ser
1               5                   10                  15

Val Lys Gly

<210> SEQ ID NO 139
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 139

Val Ser Thr Ile Ser Asp Gly Gly Thr Tyr Ile Tyr Tyr Ala Asp Asn
1               5                   10                  15

Val Lys Gly

<210> SEQ ID NO 140
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 140

Val Ser Thr Ile Ser Asp Gly Gly Thr Tyr Ile Tyr Tyr Ala Asp Ser
1               5                   10                  15

Val Lys Gly

<210> SEQ ID NO 141
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 141

Val Ser Thr Ile Ser Asp Gly Gly Thr Tyr Ile Tyr Tyr Pro Asp Asn
1               5                   10                  15

Val Lys Gly

<210> SEQ ID NO 142
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 142

Val Ser Thr Ile Ser Asp Gly Gly Thr Tyr Ile Tyr Tyr Pro Asp Ser
1               5                   10                  15

Val Lys Gly

<210> SEQ ID NO 143
<211> LENGTH: 19
<212> TYPE: PRT
<213> ORGANISM: Artificial Sequence
```

```
<220> FEATURE:
<223> OTHER INFORMATION: anti-ERBB3 antibody molecule or antigen-binding
      portion HCDR2

<400> SEQUENCE: 143

Val Ser Thr Ile Ser Asp Gly Gly Thr Tyr Thr Tyr Tyr Ala Asp Asn
1               5                   10                  15

Val Lys Gly

<210> SEQ ID NO 144
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 144

Val Ser Thr Ile Ser Asp Gly Gly Thr Tyr Thr Tyr Tyr Ala Asp Ser
1               5                   10                  15

Val Lys Gly

<210> SEQ ID NO 145
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 145

Val Ser Thr Ile Ser Asp Gly Gly Thr Tyr Thr Tyr Tyr Pro Asp Asn
1               5                   10                  15

Val Lys Gly

<210> SEQ ID NO 146
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 146

Val Ser Thr Ile Ser Asp Gly Gly Thr Tyr Thr Tyr Tyr Pro Asp Ser
1               5                   10                  15

Val Lys Gly

<210> SEQ ID NO 147
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 147

Val Ser Thr Ile Ser Asp Ser Gly Ser Thr Ile Tyr Tyr Ala Asp Asn
1               5                   10                  15

Val Lys Gly

<210> SEQ ID NO 148
<211> LENGTH: 19
<212> TYPE: PRT
```

-continued

```
<213> ORGANISM: Artificial Sequence
<220> FEATURE:
<223> OTHER INFORMATION: anti-ERBB3 antibody molecule or antigen-binding
      portion HCDR2

<400> SEQUENCE: 148

Val Ser Thr Ile Ser Asp Ser Gly Ser Thr Ile Tyr Tyr Pro Asp Asn
1               5                   10                  15

Val Lys Gly

<210> SEQ ID NO 149
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 149

Val Ser Thr Ile Ser Asp Ser Gly Ser Thr Ile Tyr Tyr Pro Asp Ser
1               5                   10                  15

Val Lys Gly

<210> SEQ ID NO 150
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 150

Val Ser Thr Ile Ser Asp Ser Gly Ser Thr Thr Tyr Tyr Ala Asp Asn
1               5                   10                  15

Val Lys Gly

<210> SEQ ID NO 151
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 151

Val Ser Thr Ile Ser Asp Ser Gly Ser Thr Thr Tyr Tyr Ala Asp Ser
1               5                   10                  15

Val Lys Gly

<210> SEQ ID NO 152
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 152

Val Ser Thr Ile Ser Asp Ser Gly Ser Thr Thr Tyr Tyr Pro Asp Asn
1               5                   10                  15

Val Lys Gly

<210> SEQ ID NO 153
<211> LENGTH: 19
```

```
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 153

Val Ser Thr Ile Ser Asp Ser Gly Ser Thr Thr Tyr Tyr Pro Asp Ser
1               5                   10                  15

Val Lys Gly

<210> SEQ ID NO 154
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 154

Val Ser Thr Ile Ser Asp Ser Gly Ser Tyr Ile Tyr Tyr Ala Asp Asn
1               5                   10                  15

Val Lys Gly

<210> SEQ ID NO 155
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 155

Val Ser Thr Ile Ser Asp Ser Gly Ser Tyr Ile Tyr Tyr Pro Asp Asn
1               5                   10                  15

Val Lys Gly

<210> SEQ ID NO 156
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 156

Val Ser Thr Ile Ser Asp Ser Gly Ser Tyr Ile Tyr Tyr Pro Asp Ser
1               5                   10                  15

Val Lys Gly

<210> SEQ ID NO 157
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 157

Val Ser Thr Ile Ser Asp Ser Gly Ser Tyr Thr Tyr Tyr Ala Asp Asn
1               5                   10                  15

Val Lys Gly

<210> SEQ ID NO 158
```

```
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 158

Val Ser Thr Ile Ser Asp Ser Gly Ser Tyr Thr Tyr Tyr Pro Asp Asn
1               5                   10                  15

Val Lys Gly

<210> SEQ ID NO 159
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 159

Val Ser Thr Ile Ser Asp Ser Gly Thr Thr Ile Tyr Tyr Ala Asp Ser
1               5                   10                  15

Val Lys Gly

<210> SEQ ID NO 160
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 160

Val Ser Thr Ile Ser Asp Ser Gly Thr Thr Tyr Tyr Ala Asp Asn
1               5                   10                  15

Val Lys Gly

<210> SEQ ID NO 161
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 161

Val Ser Thr Ile Ser Asp Ser Gly Thr Thr Tyr Tyr Ala Asp Ser
1               5                   10                  15

Val Lys Gly

<210> SEQ ID NO 162
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 162

Val Ser Thr Ile Ser Asp Ser Gly Thr Thr Tyr Tyr Pro Asp Asn
1               5                   10                  15

Val Lys Gly
```

```
<210> SEQ ID NO 163
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 163

Val Ser Thr Ile Ser Asp Ser Gly Thr Thr Tyr Tyr Pro Asp Ser
1               5                   10                  15

Val Lys Gly

<210> SEQ ID NO 164
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 164

Val Ser Thr Ile Ser Asp Ser Gly Thr Tyr Ile Tyr Tyr Ala Asp Asn
1               5                   10                  15

Val Lys Gly

<210> SEQ ID NO 165
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 165

Val Ser Thr Ile Ser Asp Ser Gly Thr Tyr Ile Tyr Tyr Ala Asp Ser
1               5                   10                  15

Val Lys Gly

<210> SEQ ID NO 166
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 166

Val Ser Thr Ile Ser Asp Ser Gly Thr Tyr Ile Tyr Tyr Pro Asp Asn
1               5                   10                  15

Val Lys Gly

<210> SEQ ID NO 167
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 167

Val Ser Thr Ile Ser Asp Ser Gly Thr Tyr Ile Tyr Tyr Pro Asp Ser
1               5                   10                  15

Val Lys Gly
```

<210> SEQ ID NO 168
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 168

Val Ser Thr Ile Ser Asp Ser Gly Thr Tyr Thr Tyr Tyr Ala Asp Asn
1               5                   10                  15

Val Lys Gly

<210> SEQ ID NO 169
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 169

Val Ser Thr Ile Ser Asp Ser Gly Thr Tyr Thr Tyr Tyr Ala Asp Ser
1               5                   10                  15

Val Lys Gly

<210> SEQ ID NO 170
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 170

Val Ser Thr Ile Ser Asp Ser Gly Thr Tyr Thr Tyr Tyr Pro Asp Asn
1               5                   10                  15

Val Lys Gly

<210> SEQ ID NO 171
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 171

Val Ser Thr Ile Ser Asn Ser Gly Thr Tyr Thr Tyr Tyr Ala Asp Ser
1               5                   10                  15

Val Lys Gly

<210> SEQ ID NO 172
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 172

Val Ser Thr Ile Ser Ser Gly Gly Ser Tyr Ile Tyr Tyr Pro Asp Ser
1               5                   10                  15

Val Lys Gly

```
<210> SEQ ID NO 173
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 173

Val Ser Thr Ile Ser Ser Gly Gly Ser Tyr Thr Tyr Tyr Pro Asp Ser
1               5                   10                  15

Val Lys Gly

<210> SEQ ID NO 174
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 174

Val Ser Thr Ile Ser Ser Ser Gly Ser Tyr Thr Tyr Tyr Ala Asp Asn
1               5                   10                  15

Val Lys Gly

<210> SEQ ID NO 175
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 175

Val Ser Thr Ile Ser Ser Ser Gly Thr Thr Thr Tyr Tyr Ala Asp Ser
1               5                   10                  15

Val Lys Gly

<210> SEQ ID NO 176
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 176

Val Ser Thr Ile Ser Ser Ser Gly Thr Tyr Ile Tyr Tyr Ala Asp Asn
1               5                   10                  15

Val Lys Gly

<210> SEQ ID NO 177
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 177

Val Ser Tyr Ile Ser Asp Gly Gly Ser Tyr Ile Tyr Tyr Ala Asp Ser
1               5                   10                  15
```

Val Lys Gly

<210> SEQ ID NO 178
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 178

Val Ser Tyr Ile Ser Asp Gly Gly Ser Tyr Thr Tyr Tyr Ala Asp Asn
1               5                   10                  15

Val Lys Gly

<210> SEQ ID NO 179
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 179

Val Ser Tyr Ile Ser Asp Gly Gly Thr Thr Ile Tyr Tyr Ala Asp Ser
1               5                   10                  15

Val Lys Gly

<210> SEQ ID NO 180
<211> LENGTH: 19
<212> TYPE: PRT
<213> ORGANISM: Artificial Sequence
<220> FEATURE:
<223> OTHER INFORMATION: anti-ERBB3 antibody molecule or antigen-binding
      portion HCDR2

<400> SEQUENCE: 180

Val Ser Tyr Ile Ser Asp Ser Gly Thr Tyr Thr Tyr Tyr Pro Asp Ser
1               5                   10                  15

Val Lys Gly

<210> SEQ ID NO 181
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 181

Glu Phe Gly Asp Tyr Asp Gly Phe Asp Phe
1               5                   10

<210> SEQ ID NO 182
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 182

Glu Phe Gly Asp Tyr Asp Gly Phe Asp Tyr
1               5                   10

```
<210> SEQ ID NO 183
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 183

Glu Leu Gly Asp Tyr Asp Gly Trp Asp Tyr
1               5                   10

<210> SEQ ID NO 184
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 184

Glu Met Gly Asp Tyr Asp Gly Phe Asp Tyr
1               5                   10

<210> SEQ ID NO 185
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 185

Glu Gln Gly Asp Tyr Asp Gly Phe Asp Ile
1               5                   10

<210> SEQ ID NO 186
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 186

Glu Trp Gly Asp Ala Asp Gly Phe Asp Tyr
1               5                   10

<210> SEQ ID NO 187
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 187

Glu Trp Gly Asp Asp Asp Gly Phe Asp Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 188
```

```
Glu Trp Gly Asp Glu Asp Gly Phe Asp Tyr
1               5                   10

<210> SEQ ID NO 189
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 189

Glu Trp Gly Asp His Asp Gly Phe Asp Tyr
1               5                   10

<210> SEQ ID NO 190
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 190

Glu Trp Gly Asp Leu Asp Gly Phe Asp Tyr
1               5                   10

<210> SEQ ID NO 191
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 191

Glu Trp Gly Asp Met Asp Gly Phe Asp Arg
1               5                   10

<210> SEQ ID NO 192
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 192

Glu Trp Gly Asp Met Asp Gly Phe Asp Tyr
1               5                   10

<210> SEQ ID NO 193
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 193

Glu Trp Gly Asp Asn Asp Gly Phe Asp Tyr
1               5                   10

<210> SEQ ID NO 194
<211> LENGTH: 10
<212> TYPE: PRT
<213> ORGANISM: Artificial Sequence
```

```
<220> FEATURE:
<223> OTHER INFORMATION: anti-ERBB3 antibody molecule or antigen-binding
      portion HCDR3

<400> SEQUENCE: 194

Glu Trp Gly Asp Gln Asp Gly Phe Asp Tyr
1               5                   10

<210> SEQ ID NO 195
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 195

Glu Trp Gly Asp Ser Asp Gly Phe Asp Tyr
1               5                   10

<210> SEQ ID NO 196
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 196

Glu Trp Gly Asp Thr Asp Gly Phe Asp Tyr
1               5                   10

<210> SEQ ID NO 197
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 197

Glu Trp Gly Asp Trp Asp Gly Phe Asp Tyr
1               5                   10

<210> SEQ ID NO 198
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 198

Glu Trp Gly Asp Tyr Asp Gly Cys Asp Tyr
1               5                   10

<210> SEQ ID NO 199
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 199

Glu Trp Gly Asp Tyr Asp Gly Phe Asp Ala
1               5                   10
```

<210> SEQ ID NO 200
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 200

Glu Trp Gly Asp Tyr Asp Gly Phe Asp Asp
1               5                   10

<210> SEQ ID NO 201
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 201

Glu Trp Gly Asp Tyr Asp Gly Phe Asp Ile
1               5                   10

<210> SEQ ID NO 202
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 202

Glu Trp Gly Asp Tyr Asp Gly Phe Asp Lys
1               5                   10

<210> SEQ ID NO 203
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 203

Glu Trp Gly Asp Tyr Asp Gly Phe Asp Leu
1               5                   10

<210> SEQ ID NO 204
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 204

Glu Trp Gly Asp Tyr Asp Gly Phe Asp Met
1               5                   10

<210> SEQ ID NO 205
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

```
<400> SEQUENCE: 205

Glu Trp Gly Asp Tyr Asp Gly Phe Asp Gln
1               5                   10

<210> SEQ ID NO 206
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 206

Glu Trp Gly Asp Tyr Asp Gly Phe Asp Arg
1               5                   10

<210> SEQ ID NO 207
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 207

Glu Trp Gly Asp Tyr Asp Gly Phe Asp Ser
1               5                   10

<210> SEQ ID NO 208
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 208

Glu Trp Gly Asp Tyr Asp Gly Phe Asp Val
1               5                   10

<210> SEQ ID NO 209
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 209

Glu Trp Gly Asp Tyr Asp Gly Phe Asp Trp
1               5                   10

<210> SEQ ID NO 210
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 210

Glu Trp Gly Asp Tyr Asp Gly Phe Asp Tyr
1               5                   10

<210> SEQ ID NO 211
<211> LENGTH: 10
<212> TYPE: PRT
```

```
<213> ORGANISM: Artificial Sequence
<220> FEATURE:
<223> OTHER INFORMATION: anti-ERBB3 antibody molecule or antigen-binding
      portion HCDR3

<400> SEQUENCE: 211

Glu Trp Gly Asp Tyr Asp Gly Phe His Tyr
1               5                   10

<210> SEQ ID NO 212
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 212

Glu Trp Gly Asp Tyr Asp Gly Ile Asp Tyr
1               5                   10

<210> SEQ ID NO 213
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 213

Glu Trp Gly Asp Tyr Asp Gly Leu Asp Tyr
1               5                   10

<210> SEQ ID NO 214
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 214

Glu Trp Gly Asp Tyr Asp Gly Trp Asp Tyr
1               5                   10

<210> SEQ ID NO 215
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 215

Glu Trp Gly Asp Tyr Asp Gly Tyr Asp Tyr
1               5                   10

<210> SEQ ID NO 216
<211> LENGTH: 10
<212> TYPE: PRT
<213> ORGANISM: Artificial Sequence
<220> FEATURE:
<223> OTHER INFORMATION: anti-ERBB3 antibody molecule or antigen-binding
      portion HCDR3

<400> SEQUENCE: 216

Met Trp Gly Asp Tyr Asp Gly Phe Asp Tyr
1               5                   10
```

<210> SEQ ID NO 217
<211> LENGTH: 107
<212> TYPE: PRT
<213> ORGANISM: Artificial Sequence
<220> FEATURE:
<223> OTHER INFORMATION: 15G11-DI1 VL

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Ser Tyr
            20                  25                  30

Leu Ser Trp Tyr Gln Gln Lys Pro Gly Lys Ala Pro Lys Leu Leu Ile
        35                  40                  45

Tyr Ala Ala Ser Ser Leu Asp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Thr Pro Tyr
                85                  90                  95

Thr Phe Gly Gly Gly Thr Lys Val Glu Ile Lys
            100                 105

<210> SEQ ID NO 218
<211> LENGTH: 107
<212> TYPE: PRT
<213> ORGANISM: Artificial Sequence
<220> FEATURE:
<223> OTHER INFORMATION: 15G11-DI2 VL

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Thr Tyr
            20                  25                  30

Leu Ser Trp Tyr Gln Gln Lys Pro Gly Lys Ala Pro Lys Leu Leu Ile
        35                  40                  45

Tyr Ala Ala Ser Ser Leu Asp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Thr Pro Tyr
                85                  90                  95

Thr Phe Gly Gly Gly Thr Lys Val Glu Ile Lys
            100                 105

<210> SEQ ID NO 219
<211> LENGTH: 107
<212> TYPE: PRT
<213> ORGANISM: Artificial Sequence
<220> FEATURE:
<223> OTHER INFORMATION: 15G11-DI3 VL

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Ser Tyr
            20                  25                  30

-continued

Leu Ser Trp Tyr Gln Gln Lys Pro Gly Lys Ala Pro Lys Leu Leu Ile
            35                  40                  45

Tyr Ala Ala Ser Ser Leu Asp Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Ser Ser Pro Tyr
                 85                  90                  95

Thr Phe Gly Gly Gly Thr Lys Val Glu Ile Lys
            100                 105

<210> SEQ ID NO 220
<211> LENGTH: 107
<212> TYPE: PRT
<213> ORGANISM: Artificial Sequence
<220> FEATURE:
<223> OTHER INFORMATION: 15G11-DI4 VL

<400> SEQUENCE: 220

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Thr Tyr
            20                  25                  30

Leu Ser Trp Tyr Gln Gln Lys Pro Gly Lys Ala Pro Lys Leu Leu Ile
            35                  40                  45

Tyr Ala Ala Ser Ser Leu Asp Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Ser Ser Pro Tyr
                 85                  90                  95

Thr Phe Gly Gly Gly Thr Lys Val Glu Ile Lys
            100                 105

<210> SEQ ID NO 221
<211> LENGTH: 107
<212> TYPE: PRT
<213> ORGANISM: Artificial Sequence
<220> FEATURE:
<223> OTHER INFORMATION: 15G11-DI5 VL

<400> SEQUENCE: 221

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Glu Ile Ser Ser Tyr
            20                  25                  30

Leu Ser Trp Tyr Gln Gln Lys Pro Gly Lys Ala Pro Lys Leu Leu Ile
            35                  40                  45

Tyr Ala Ala Ser Ser Leu Asp Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Ser Thr Pro Tyr
                 85                  90                  95

Thr Phe Gly Gly Gly Thr Lys Val Glu Ile Lys
            100                 105

<210> SEQ ID NO 222

```
<211> LENGTH: 107
<212> TYPE: PRT
<213> ORGANISM: Artificial Sequence
<220> FEATURE:
<223> OTHER INFORMATION: 15G11-DI6 VL

<400> SEQUENCE: 222

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Thr Tyr
            20                  25                  30

Leu Ser Trp Tyr Gln Gln Lys Pro Gly Lys Ala Pro Lys Leu Leu Ile
        35                  40                  45

Tyr Ala Ala Ser Ser Leu Asp Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Thr Pro Tyr
                85                  90                  95

Thr Phe Gly Gly Gly Thr Lys Val Glu Ile Lys
            100                 105

<210> SEQ ID NO 223
<211> LENGTH: 107
<212> TYPE: PRT
<213> ORGANISM: Artificial Sequence
<220> FEATURE:
<223> OTHER INFORMATION: 15G11-DI7 VL

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Ser Tyr
            20                  25                  30

Leu Ser Trp Tyr Gln Gln Lys Pro Gly Lys Ala Pro Lys Leu Leu Ile
        35                  40                  45

Tyr Ala Ala Ser Ser Leu Asp Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Ser Pro Tyr
                85                  90                  95

Thr Phe Gly Gly Gly Thr Lys Val Glu Ile Lys
            100                 105

<210> SEQ ID NO 224
<211> LENGTH: 107
<212> TYPE: PRT
<213> ORGANISM: Artificial Sequence
<220> FEATURE:
<223> OTHER INFORMATION: 15G11-DI8 VL

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Thr Tyr
            20                  25                  30

Leu Ser Trp Tyr Gln Gln Lys Pro Gly Lys Ala Pro Lys Leu Leu Ile
        35                  40                  45
```

```
Tyr Ala Ala Ser Ser Leu Asp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Ser Pro Tyr
                85                  90                  95

Thr Phe Gly Gly Gly Thr Lys Val Glu Ile Lys
                100                 105
```

<210> SEQ ID NO 225
<211> LENGTH: 107
<212> TYPE: PRT
<213> ORGANISM: Artificial Sequence
<220> FEATURE:
<223> OTHER INFORMATION: 15G11-DI9 VL

<400> SEQUENCE: 225

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Thr Tyr
                20                  25                  30

Leu Ser Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Ser Pro Leu
                85                  90                  95

Thr Phe Gly Gly Gly Thr Lys Val Glu Ile Lys
                100                 105
```

<210> SEQ ID NO 226
<211> LENGTH: 107
<212> TYPE: PRT
<213> ORGANISM: Artificial Sequence
<220> FEATURE:
<223> OTHER INFORMATION: 15G11-DI10 VL

<400> SEQUENCE: 226

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Ser Tyr
                20                  25                  30

Leu Ser Trp Tyr Gln Gln Lys Pro Gly Lys Ala Pro Lys Leu Leu Ala
            35                  40                  45

Tyr Ala Ala Ser Ser Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Thr Pro Tyr
                85                  90                  95

Thr Phe Gly Gly Gly Thr Lys Val Glu Ile Lys
                100                 105
```

<210> SEQ ID NO 227
<211> LENGTH: 107
<212> TYPE: PRT
<213> ORGANISM: Artificial Sequence

```
<220> FEATURE:
<223> OTHER INFORMATION: 15G11-DI11 VL

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ala Ser Ser Tyr
            20                  25                  30

Leu Ser Trp Tyr Gln Gln Lys Pro Gly Lys Ala Pro Lys Leu Leu Ala
        35                  40                  45

Tyr Ala Ala Ser Ser Leu Asp Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Ser Pro Tyr
                85                  90                  95

Thr Phe Gly Gly Gly Thr Lys Val Glu Ile Lys
            100                 105

<210> SEQ ID NO 228
<211> LENGTH: 119
<212> TYPE: PRT
<213> ORGANISM: Artificial Sequence
<220> FEATURE:
<223> OTHER INFORMATION: 15G11-DI1 VH

<400> SEQUENCE: 228

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45

Ser Thr Ile Ser Asp Ser Gly Ser Tyr Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Gly Asp Tyr Asp Gly Phe Asp Tyr Trp Gly Gln Gly
            100                 105                 110

Thr Leu Val Thr Val Ser Ser
        115

<210> SEQ ID NO 229
<211> LENGTH: 119
<212> TYPE: PRT
<213> ORGANISM: Artificial Sequence
<220> FEATURE:
<223> OTHER INFORMATION: 15G11-DI2 VH

<400> SEQUENCE: 229

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Gly Met Ser Trp Val Arg Gln Ala Pro Gly Lys Gly Leu Glu Trp Val
        35                  40                  45
```

```
Ser Thr Ile Ser Asp Ser Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Gly Asp Tyr Asp Gly Phe Asp Tyr Trp Gly Gln Gly
                100                 105                 110

Thr Leu Val Thr Val Ser Ser
        115

<210> SEQ ID NO 230
<211> LENGTH: 119
<212> TYPE: PRT
<213> ORGANISM: Artificial Sequence
<220> FEATURE:
<223> OTHER INFORMATION: 15G11-DI3 VH

<400> SEQUENCE: 230

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Gly Met Ser Trp Val Arg Gln Ala Pro Gly Lys Gly Leu Glu Trp Val
             35                  40                  45

Ser Thr Ile Ser Asp Ser Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Gly Asp Tyr Asp Gly Phe Asp Tyr Trp Gly Gln Gly
                100                 105                 110

Thr Leu Val Thr Val Ser Ser
        115

<210> SEQ ID NO 231
<211> LENGTH: 119
<212> TYPE: PRT
<213> ORGANISM: Artificial Sequence
<220> FEATURE:
<223> OTHER INFORMATION: 15G11-DI4 VH

<400> SEQUENCE: 231

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Gly Met Ser Trp Val Arg Gln Ala Pro Gly Lys Gly Leu Glu Trp Val
             35                  40                  45

Ser Thr Ile Ser Asp Ser Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Gly Asp Tyr Asp Gly Phe Asp Tyr Trp Gly Gln Gly
                100                 105                 110
```

Thr Leu Val Thr Val Ser Ser
        115

<210> SEQ ID NO 232
<211> LENGTH: 119
<212> TYPE: PRT
<213> ORGANISM: Artificial Sequence
<220> FEATURE:
<223> OTHER INFORMATION: 15G11-DI5 VH

<400> SEQUENCE: 232

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Ile Arg Gln Ala Pro Gly Lys Gly Leu Glu Trp Val
        35                  40                  45

Ser Thr Ile Ser Asp Ser Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Phe Trp Gly Gln Gly
            100                 105                 110

Thr Leu Val Thr Val Ser Ser
        115

<210> SEQ ID NO 233
<211> LENGTH: 119
<212> TYPE: PRT
<213> ORGANISM: Artificial Sequence
<220> FEATURE:
<223> OTHER INFORMATION: 15G11-DI6 VH

<400> SEQUENCE: 233

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Ile Arg Gln Ala Pro Gly Lys Gly Leu Glu Trp Val
        35                  40                  45

Ser Thr Ile Ser Asp Ser Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Phe Trp Gly Gln Gly
            100                 105                 110

Thr Leu Val Thr Val Ser Ser
        115

<210> SEQ ID NO 234
<211> LENGTH: 119
<212> TYPE: PRT
<213> ORGANISM: Artificial Sequence
<220> FEATURE:
<223> OTHER INFORMATION: 15G11-DI7 VH

<400> SEQUENCE: 234

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Ile Arg Gln Ala Pro Gly Lys Gly Leu Glu Trp Val
        35                  40                  45

Ser Thr Ile Ser Asp Ser Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Phe Trp Gly Gln Gly
            100                 105                 110

Thr Leu Val Thr Val Ser Ser
        115
```

<210> SEQ ID NO 235
<211> LENGTH: 119
<212> TYPE: PRT
<213> ORGANISM: Artificial Sequence
<220> FEATURE:
<223> OTHER INFORMATION: 15G11-DI8 VH

<400> SEQUENCE: 235

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Ile Arg Gln Ala Pro Gly Lys Gly Leu Glu Trp Val
        35                  40                  45

Ser Thr Ile Ser Asp Ser Gly Thr Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Asp Tyr Asp Gly Phe Asp Phe Trp Gly Gln Gly
            100                 105                 110

Thr Leu Val Thr Val Ser Ser
        115
```

<210> SEQ ID NO 236
<211> LENGTH: 119
<212> TYPE: PRT
<213> ORGANISM: Artificial Sequence
<220> FEATURE:
<223> OTHER INFORMATION: 15G11-DI9 VH

<400> SEQUENCE: 236

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Ile Arg Gln Ala Pro Gly Lys Gly Leu Glu Trp Val
        35                  40                  45
```

Ser Thr Ile Ser Asp Ser Gly Thr Tyr Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Trp Gly Asp Tyr Asp Gly Phe Asp Phe Trp Gly Gln Gly
                100                 105                 110

Thr Leu Val Thr Val Ser Ser
        115

<210> SEQ ID NO 237
<211> LENGTH: 119
<212> TYPE: PRT
<213> ORGANISM: Artificial Sequence
<220> FEATURE:
<223> OTHER INFORMATION: 15G11-DI10 VH

<400> SEQUENCE: 237

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Gly Met Ser Trp Val Arg Gln Ala Pro Gly Lys Gly Leu Glu Trp Val
             35                  40                  45

Ser Thr Ile Ser Asp Ser Gly Ser Tyr Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Gly Asp Tyr Asp Gly Phe Asp Tyr Trp Gly Gln Gly
                100                 105                 110

Thr Leu Val Thr Val Ser Ser
        115

<210> SEQ ID NO 238
<211> LENGTH: 119
<212> TYPE: PRT
<213> ORGANISM: Artificial Sequence
<220> FEATURE:
<223> OTHER INFORMATION: 15G11-DI11 VH

<400> SEQUENCE: 238

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Gly Met Ser Trp Val Arg Gln Ala Pro Gly Lys Gly Leu Glu Trp Val
             35                  40                  45

Ser Thr Ile Ser Asp Ser Gly Ser Tyr Thr Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Gly Asp Tyr Asp Gly Phe Asp Tyr Trp Gly Gln Gly

```
                  100                 105                 110

Thr Leu Val Thr Val Ser Ser
            115

<210> SEQ ID NO 239
<211> LENGTH: 327
<212> TYPE: PRT
<213> ORGANISM: Homo sapiens

<400> SEQUENCE: 239

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 240
<211> LENGTH: 327
```

```
<212> TYPE: PRT
<213> ORGANISM: Homo sapiens

<400> SEQUENCE: 240

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 241
<211> LENGTH: 330
<212> TYPE: PRT
<213> ORGANISM: Homo sapiens

<400> SEQUENCE: 241

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 242
<211> LENGTH: 330
<212> TYPE: PRT
<213> ORGANISM: Homo sapiens

<400> SEQUENCE: 242

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 243
<211> LENGTH: 326
<212> TYPE: PRT
<213> ORGANISM: Homo sapiens

<400> SEQUENCE: 243

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro

-continued

```
                100                 105                 110
Pro Val Ala Gly Pro Ser Val Phe Leu Phe Pro Lys Pro Lys Asp
            115                 120                 125

Thr Leu Met Ile Ser Arg Thr Pro Glu Val Thr Cys Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 244
<211> LENGTH: 330
<212> TYPE: PRT
<213> ORGANISM: Homo sapiens

<400> SEQUENCE: 244

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

-continued

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 245
<211> LENGTH: 329
<212> TYPE: PRT
<213> ORGANISM: Homo sapiens

<400> SEQUENCE: 245

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 246
<211> LENGTH: 1342
<212> TYPE: PRT
<213> ORGANISM: Homo sapiens

<400> SEQUENCE: 246

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
```

-continued

```
            225                 230                 235                 240
        Thr Asp Cys Phe Ala Cys Arg His Phe Asn Asp Ser Gly Ala Cys Val
                        245                 250                 255
        Pro Arg Cys Pro Gln Pro Leu Val Tyr Asn Lys Leu Thr Phe Gln Leu
                        260                 265                 270
        Glu Pro Asn Pro His Thr Lys Tyr Gln Tyr Gly Val Cys Val Ala
                        275                 280                 285
        Ser Cys Pro His Asn Phe Val Val Asp Gln Thr Ser Cys Val Arg Ala
                        290                 295                 300
        Cys Pro Pro Asp Lys Met Glu Val Asp Lys Asn Gly Leu Lys Met Cys
        305                 310                 315                 320
        Glu Pro Cys Gly Gly Leu Cys Pro Lys Ala Cys Glu Gly Thr Gly Ser
                        325                 330                 335
        Gly Ser Arg Phe Gln Thr Val Asp Ser Ser Asn Ile Asp Gly Phe Val
                        340                 345                 350
        Asn Cys Thr Lys Ile Leu Gly Asn Leu Asp Phe Leu Ile Thr Gly Leu
                        355                 360                 365
        Asn Gly Asp Pro Trp His Lys Ile Pro Ala Leu Asp Pro Glu Lys Leu
                        370                 375                 380
        Asn Val Phe Arg Thr Val Arg Glu Ile Thr Gly Tyr Leu Asn Ile Gln
        385                 390                 395                 400
        Ser Trp Pro Pro His Met His Asn Phe Ser Val Phe Ser Asn Leu Thr
                        405                 410                 415
        Thr Ile Gly Gly Arg Ser Leu Tyr Asn Arg Gly Phe Ser Leu Leu Ile
                        420                 425                 430
        Met Lys Asn Leu Asn Val Thr Ser Leu Gly Phe Arg Ser Leu Lys Glu
                        435                 440                 445
        Ile Ser Ala Gly Arg Ile Tyr Ile Ser Ala Asn Arg Gln Leu Cys Tyr
                        450                 455                 460
        His His Ser Leu Asn Trp Thr Lys Val Leu Arg Gly Pro Thr Glu Glu
        465                 470                 475                 480
        Arg Leu Asp Ile Lys His Asn Arg Pro Arg Arg Asp Cys Val Ala Glu
                        485                 490                 495
        Gly Lys Val Cys Asp Pro Leu Cys Ser Ser Gly Gly Cys Trp Gly Pro
                        500                 505                 510
        Gly Pro Gly Gln Cys Leu Ser Cys Arg Asn Tyr Ser Arg Gly Gly Val
                        515                 520                 525
        Cys Val Thr His Cys Asn Phe Leu Asn Gly Glu Pro Arg Glu Phe Ala
                        530                 535                 540
        His Glu Ala Glu Cys Phe Ser Cys His Pro Glu Cys Gln Pro Met Glu
        545                 550                 555                 560
        Gly Thr Ala Thr Cys Asn Gly Ser Gly Ser Asp Thr Cys Ala Gln Cys
                        565                 570                 575
        Ala His Phe Arg Asp Gly Pro His Cys Val Ser Ser Cys Pro His Gly
                        580                 585                 590
        Val Leu Gly Ala Lys Gly Pro Ile Tyr Lys Tyr Pro Asp Val Gln Asn
                        595                 600                 605
        Glu Cys Arg Pro Cys His Glu Asn Cys Thr Gln Gly Cys Lys Gly Pro
                        610                 615                 620
        Glu Leu Gln Asp Cys Leu Gly Gln Thr Leu Val Leu Ile Gly Lys Thr
        625                 630                 635                 640
        His Leu Thr Met Ala Leu Thr Val Ile Ala Gly Leu Val Val Ile Phe
                        645                 650                 655
```

-continued

Met Met Leu Gly Gly Thr Phe Leu Tyr Trp Arg Gly Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
        995                 1000                1005

Leu Asp Leu Asp Leu Asp Leu Glu Ala Glu Glu Asp Asn Leu Ala
    1010                1015                1020

Thr Thr Thr Leu Gly Ser Ala Leu Ser Leu Pro Val Gly Thr Leu
    1025                1030                1035

Asn Arg Pro Arg Gly Ser Gln Ser Leu Leu Ser Pro Ser Ser Gly
    1040                1045                1050

Tyr Met Pro Met Asn Gln Gly Asn Leu Gly Glu Ser Cys Gln Glu
    1055                1060                1065

```
Ser Ala Val Ser Gly Ser Ser Glu Arg Cys Pro Arg Pro Val Ser
    1070                1075                1080

Leu His Pro Met Pro Arg Gly Cys Leu Ala Ser Glu Ser Ser Glu
    1085                1090                1095

Gly His Val Thr Gly Ser Glu Ala Glu Leu Gln Glu Lys Val Ser
    1100                1105                1110

Met Cys Arg Ser Arg Ser Arg Ser Arg Ser Pro Arg Pro Arg Gly
    1115                1120                1125

Asp Ser Ala Tyr His Ser Gln Arg His Ser Leu Leu Thr Pro Val
    1130                1135                1140

Thr Pro Leu Ser Pro Pro Gly Leu Glu Glu Asp Val Asn Gly
    1145                1150                1155

Tyr Val Met Pro Asp Thr His Leu Lys Gly Thr Pro Ser Ser Arg
    1160                1165                1170

Glu Gly Thr Leu Ser Ser Val Gly Leu Ser Ser Val Leu Gly Thr
    1175                1180                1185

Glu Glu Glu Asp Glu Asp Glu Tyr Glu Tyr Met Asn Arg Arg
    1190                1195                1200

Arg Arg His Ser Pro Pro His Pro Pro Arg Pro Ser Ser Leu Glu
    1205                1210                1215

Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 247
<211> LENGTH: 1342
<212> TYPE: PRT
<213> ORGANISM: Macaca mulatta

<400> SEQUENCE: 247

Met Arg Ala Asn Gly Ala Leu Gln Val Leu Gly Leu Leu Phe Asn Leu
1               5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
        50                  55                  60

Ile Val Leu Thr Gly His Asn Ala Asp Leu Ser Phe Leu Gln Trp Ile
65                  70                  75                  80
```

```
Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Lys Asp Ile Val Arg Asp Gln Asp Ala Glu Ile Val Val
                165                 170                 175

Lys Asp Asn Gly Arg Ser Cys Pro Leu Cys His Glu Val Cys Lys Gly
            180                 185                 190

Arg Cys Trp Gly Pro Gly Pro Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
        275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
    370                 375                 380

Asn Val Phe Arg Thr Val Arg Glu Ile Thr Gly Tyr Leu Asn Ile Gln
385                 390                 395                 400

Ser Trp Pro Pro His Met Tyr Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495
```

Gly Lys Val Cys Asp Pro Leu Cys Ser Ser Gly Cys Trp Gly Pro
                500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
        530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Ile Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
        835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu

```
                915                 920                 925
Arg Leu Ala Gln Pro Gln Ile Cys Thr Ile Asp Val Tyr Met Val Met
        930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Pro Arg Tyr Leu
                965                 970                 975
Val Ile Lys Arg Glu Ser Gly Pro Gly Ile Ala Pro Gly Pro Glu Pro
        980                 985                 990
His Gly Leu Thr Asn Lys Lys Leu Glu Glu Val Glu Leu Glu Pro Glu
            995                1000                1005
Leu Asp Leu Asp Leu Asp Leu Glu Ala Glu Glu Asp Asn Leu Ala
    1010                1015                1020
Thr Thr Thr Leu Gly Ser Ala Leu Ser Leu Pro Val Gly Thr Leu
    1025                1030                1035
Asn Arg Pro Arg Gly Ser Gln Ser Leu Leu Ser Pro Ser Ser Gly
    1040                1045                1050
Tyr Met Pro Met Asn Gln Gly Asn Leu Gly Glu Ala Cys Gln Glu
    1055                1060                1065
Ser Ala Val Ser Gly Ser Ser Glu Trp Cys Pro Arg Pro Val Ser
    1070                1075                1080
Leu His Pro Met Pro Arg Gly Cys Leu Ala Ser Glu Ser Ser Glu
    1085                1090                1095
Gly His Val Thr Gly Ser Glu Ala Glu Leu Gln Glu Lys Val Ser
    1100                1105                1110
Thr Cys Arg Ser Arg Ser Arg Ser Arg Ser Pro Arg Pro Arg Gly
    1115                1120                1125
Asp Ser Ala Tyr His Ser Gln Arg His Ser Leu Leu Thr Pro Val
    1130                1135                1140
Thr Pro Leu Ser Pro Pro Gly Leu Glu Glu Glu Asp Val Asn Gly
    1145                1150                1155
Tyr Val Met Pro Asp Thr His Leu Lys Gly Thr Pro Ser Ser Arg
    1160                1165                1170
Glu Gly Thr Leu Ser Ser Val Gly Leu Ser Ser Val Leu Gly Thr
    1175                1180                1185
Glu Glu Glu Asp Glu Asp Glu Glu Tyr Glu Tyr Met Asn Arg Arg
    1190                1195                1200
Arg Arg His Ser Pro Pro Arg Pro Pro Arg Pro Ser Ser Leu Glu
    1205                1210                1215
Glu Leu Gly Tyr Glu Tyr Met Asp Val Gly Ser Asp Leu Ser Ala
    1220                1225                1230
Ser Leu Gly Ser Thr Gln Ser Cys Pro Leu His Pro Val Pro Val
    1235                1240                1245
Met Pro Thr Ala Gly Thr Thr Pro Asp Glu Asp Tyr Glu Tyr Met
    1250                1255                1260
Asn Arg Gln Arg Gly Gly Ser Gly Pro Gly Gly Asp Tyr Ala Ala
    1265                1270                1275
Met Gly Ala Cys Pro Ala Ser Glu Gln Gly Tyr Glu Glu Met Arg
    1280                1285                1290
Ala Phe Gln Gly Pro Gly His Gln Ala Pro His Val His Tyr Ala
    1295                1300                1305
His Leu Lys Thr Leu Arg Ser Leu Glu Ala Thr Asp Ser Ala Phe
    1310                1315                1320
```

Asp Asn Pro Asp Tyr Trp His Ser Arg Leu Phe Pro Lys Ala Asn
    1325                1330                1335

Ala Gln Arg Thr
    1340

<210> SEQ ID NO 248
<211> LENGTH: 5
<212> TYPE: PRT
<213> ORGANISM: Homo sapiens

<400> SEQUENCE: 248

Arg Asp Glu Leu Thr
1               5

<210> SEQ ID NO 249
<211> LENGTH: 4
<212> TYPE: PRT
<213> ORGANISM: Homo sapiens

<400> SEQUENCE: 249

Arg Glu Glu Met
1

<210> SEQ ID NO 250
<211> LENGTH: 9
<212> TYPE: PRT
<213> ORGANISM: Artificial Sequence
<220> FEATURE:
<223> OTHER INFORMATION: epitope-ablating variant peptide

<400> SEQUENCE: 250

Tyr Ser Met Ser Trp Ile Arg Gln Ala
1               5

<210> SEQ ID NO 251
<211> LENGTH: 9
<212> TYPE: PRT
<213> ORGANISM: Artificial Sequence
<220> FEATURE:
<223> OTHER INFORMATION: epitope-ablating variant peptide

<400

-continued

```
                1               5                   10                  15
            Ser Leu Arg Leu Ser Cys Ala Ala Ser Gly Phe Thr Phe Ser Asp Tyr
                        20                  25                  30

Gly Met Ser Trp Ile Arg Gln Ala Pro Gly Lys Gly Leu Glu Trp Val
                        35                  40                  45

Ser Thr Ile Ser Asp Ser Gly Ser Tyr Thr Tyr Tyr Pro Asp Ser Val
                        50                  55                  60

Lys Gly Arg Phe Thr Ile Ser Arg Asp Asn Ala Lys Asn Ser Leu Tyr
             65                  70                  75                  80

Leu Gln Met Asn Ser Leu Arg Ala Glu Asp Thr Ala Val Tyr Tyr Cys
                        85                  90                  95

Ala Arg Glu Leu Gly Asp Tyr Asp Gly Phe Asp Tyr Trp Gly Gln Gly
                        100                 105                 110

Thr Leu Val Thr Val Ser Ser
                        115

<210> SEQ ID NO 254
<211> LENGTH: 107
<212> TYPE: PRT
<213> ORGANISM: Artificial Sequence
<220> FEATURE:
<223> OTHER INFORMATION: Antibody 15G11 light chain variable (VL) region

<400> SEQUENCE: 254

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Glu Ile Ser Ser Tyr
            20                  25                  30

Leu Ser Trp Tyr Gln Gln Lys Pro Gly Lys Ala Pro Lys Leu Leu Ile
            35                  40                  45

Tyr Ala Ala Ser Ser Leu Asp Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Ser Thr Pro Tyr
            85                  90                  95

Thr Phe Gly Gly Gly Thr Lys Val Glu Ile Lys
            100                 105

<210> SEQ ID NO 255
<211> LENGTH: 119
<212> TYPE: PRT
<213> ORGANISM: Artificial Sequence
<220> FEATURE:
<223> OTHER INFORMATION: Antibody 16B09 heavy chain variable (VH) region

<400> SEQUENCE: 255

Gln Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asp Tyr
            20                  25                  30

Ser Met Ser Trp Ile Arg Gln Ala Pro Gly Lys Gly Leu Glu Trp Val
            35                  40                  45

Ser Thr Ile Ser Asp Ser Gly Thr Tyr Thr Tyr Tyr Pro Asp Ser Val
            50                  55                  60

Lys Gly Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
            85                  90                  95

Ala Arg Glu Trp Gly Asp Tyr Asp Gly Phe Asp Phe Trp Gly Gln Gly
        100                 105                 110

Thr Leu Val Thr Val Ser Ser
        115

<210> SEQ ID NO 256
<211> LENGTH: 107
<212> TYPE: PRT
<213> ORGANISM: Artificial Sequence
<220> FEATURE:
<223> OTHER INFORMATION: Antibody 16B09 light chain variable (VL) region

<400> SEQUENCE: 256

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Ser Ser Tyr
            20                  25                  30

Leu Ser Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Thr Pro Leu
                85                  90                  95

Thr Phe Gly Gly Gly Thr Lys Val Glu Ile Lys
            100                 105

<210> SEQ ID NO 257
<211> LENGTH: 16
<212> TYPE: PRT
<213> ORGANISM: Artificial Sequence
<220> FEATURE:
<223> OTHER INFORMATION: portion of anti-ERBB3 15G11 antibody VH region
<220> FEATURE:
<221> NAME/KEY: misc_feature
<222> LOCATION: (4)..(4)
<223> OTHER INFORMATION: Xaa is Tyr, Ala, Gly, His, Ser or any non-
      hydrophobic amino acid
<220> FEATURE:
<221> NAME/KEY: misc_feature
<222> LOCATION: (5)..(5)
<223> OTHER INFORMATION: Xaa is Gly, Ala, Ser, Trp or Tyr
<220> FEATURE:
<221> NAME/KEY: misc_feature
<222> LOCATION: (6)..(6)
<223> OTHER INFORMATION: Xaa is Met, Ala, Phe, Ser, Val, Trp or Tyr
<220> FEATURE:
<221> NAME/KEY: misc_feature
<222> LOCATION: (7)..(7)
<223> OTHER INFORMATION: Xaa is Ser, Gly, Asn or Tyr
<220> FEATURE:
<221> NAME/KEY: misc_feature
<222> LOCATION: (9)..(9)
<223> OTHER INFORMATION: Xaa is Ile or Val
<220> FEATURE:
<221> NAME/KEY: misc_feature
<222> LOCATION: (12)..(12)
<223> OTHER INFORMATION: Xaa is Ala, Pro or Thr

<400> SEQUENCE: 257

Phe Ser Asp Xaa Xaa Xaa Xaa Trp Xaa Arg Gln Xaa Pro Gly Lys Gly
1               5                   10                  15
```

```
<210> SEQ ID NO 258
<211> LENGTH: 16
<212> TYPE: PRT
<213> ORGANISM: Artificial Sequence
<220> FEATURE:
<223> OTHER INFORMATION: portion of anti-ERBB3 15G11 antibody VL region
<220> FEATURE:
<221> NAME/KEY: misc_feature
<222> LOCATION: (4)..(4)
<223> OTHER INFORMATION: Xaa is Ile, Ala, Gly, Ser or any non-
      hydrophobic amino acid
<220> FEATURE:
<221> NAME/KEY: misc_feature
<222> LOCATION: (5)..(5)
<223> OTHER INFORMATION: Xaa is Ser or Asp
<220> FEATURE:
<221> NAME/KEY: misc_feature
<222> LOCATION: (6)..(6)
<223> OTHER INFORMATION: Xaa is Ser, Asp, Lys or Thr
<220> FEATURE:
<221> NAME/KEY: misc_feature
<222> LOCATION: (7)..(7)
<223> OTHER INFORMATION: Xaa is Tyr, Ala, Arg, Ser or Trp
<220> FEATURE:
<221> NAME/KEY: misc_feature
<222> LOCATION: (9)..(9)
<223> OTHER INFORMATION: Xaa is Ser, Ala, Gly, His, Asn or Tyr
<220> FEATURE:
<221> NAME/KEY: misc_feature
<222> LOCATION: (12)..(12)
<223> OTHER INFORMATION: Xaa is Gln or Arg

<400> SEQUENCE: 258

Ser Gln Glu Xaa Xaa Xaa Xaa Leu Xaa Trp Tyr Xaa Gln Lys Pro Gly
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: portion of anti-ERBB3 15G11 antibody VL region
<220> FEATURE:
<221> NAME/KEY: misc_feature
<222> LOCATION: (6)..(6)
<223> OTHER INFORMATION: Xaa is Ala or Asp
<220> FEATURE:
<221> NAME/KEY: misc_feature
<222> LOCATION: (7)..(7)
<223> OTHER INFORMATION: Xaa is Ala or Asp
<220> FEATURE:
<221> NAME/KEY: misc_feature
<222> LOCATION: (12)..(12)
<223> OTHER INFORMATION: Xaa is Ser, Asp, Pro or Thr

<400> SEQUENCE: 259

Lys Leu Leu Ile Tyr Xaa Xaa Ser Ser Leu Asp Xaa Gly Val Pro
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: portion of anti-ERBB3 15G11 antibody VL region
<220> FEATURE:
<221> NAME/KEY: misc_feature
<222> LOCATION: (4)..(4)
<223> OTHER INFORMATION: Xaa is Leu, Ala, Gly, His, Gln, Ser or any non-
      hydrophobic amino acid
<220> FEATURE:
<221> NAME/KEY: misc_feature
<222> LOCATION: (5)..(5)
<223> OTHER INFORMATION: Xaa is Gln, Ala, His, Ser or Thr
<220> FEATURE:
```

```
<221> NAME/KEY: misc_feature
<222> LOCATION: (6)..(6)
<223> OTHER INFORMATION: Xaa is Tyr, Ala, Gly, His, Ser or Trp
<220> FEATURE:
<221> NAME/KEY: misc_feature
<222> LOCATION: (9)..(9)
<223> OTHER INFORMATION: Xaa is Thr, Ala, Gly, Asn, Ser or Tyr
<220> FEATURE:
<221> NAME/KEY: misc_feature
<222> LOCATION: (10)..(10)
<223> OTHER INFORMATION: Xaa is Pro, Asp, Ser or Thr

<400> SEQUENCE: 260

Tyr Tyr Cys Xaa Xaa Xaa Asp Ser Xaa Xaa Tyr Thr Phe Gly Gly
1               5                   10                  15

<210> SEQ ID NO 261
<211> LENGTH: 11
<212> TYPE: PRT
<213> ORGANISM: Artificial Sequence
<220> FEATURE:
<223> OTHER INFORMATION: anti-ERBB3 antibody molecule or antigen-binding
      portion LCDR1

<400> SEQUENCE: 261

Arg Ala Ser Gln Glu Ile Ser Thr Tyr Leu Ser
1               5                   10

<210> SEQ ID NO 262
<211> LENGTH: 9
<212> TYPE: PRT
<213> ORGANISM: Artificial Sequence
<220> FEATURE:
<223> OTHER INFORMATION: anti-ERBB3 antibody molecule or antigen-binding
      portion LCDR3

<400> SEQUENCE: 262

Leu Gln Tyr Asp Ser Ser Pro Leu Thr
1               5

<210> SEQ ID NO 263
<211> LENGTH: 7
<212> TYPE: PRT
<213> ORGANISM: Artificial Sequence
<220> FEATURE:
<223> OTHER INFORMATION: anti-ERBB3 antibody molecule or antigen-binding
      portion LCDR2

<400> SEQUENCE: 263

Ala Ala Ser Ser Leu Asp Thr
1               5
```